(12) United States Patent
Yin et al.

(10) Patent No.: US 9,650,647 B2
(45) Date of Patent: May 16, 2017

(54) MOLECULAR INTERACTION BETWEEN XA10 AND AVRXA10

(75) Inventors: Zhong Chao Yin, Singapore (SG); Ke Yu Gu, Singapore (SG); Dong Sheng Tian, Singapore (SG)

(73) Assignee: Temasek Life Sciences Laboratory Limited, Singapore (SG)

( * ) Notice: Subject to any disclaimer, the term of this patent is extended or adjusted under 35 U.S.C. 154(b) by 469 days.

(21) Appl. No.: 13/820,860

(22) PCT Filed: Sep. 6, 2010

(86) PCT No.: PCT/SG2010/000324
§ 371 (c)(1),
(2), (4) Date: Mar. 5, 2013

(87) PCT Pub. No.: WO2012/033462
PCT Pub. Date: Mar. 15, 2012

(65) Prior Publication Data
US 2013/0227744 A1    Aug. 29, 2013

(51) Int. Cl.
*C12N 15/29* (2006.01)
*C12N 15/82* (2006.01)
*C07K 14/415* (2006.01)

(52) U.S. Cl.
CPC ........ *C12N 15/8281* (2013.01); *C07K 14/415* (2013.01); *C12N 15/8239* (2013.01)

(58) Field of Classification Search
None
See application file for complete search history.

(56) References Cited

U.S. PATENT DOCUMENTS 5,859,339 A * 1/1999 Ronald et al. ................. 800/279
7,435,874 B2 * 10/2008 Gebhardt et al. ............ 800/279

2004/0241651 A1    12/2004    Olek et al.
2007/0083945 A1    4/2007    Byrum et al.
2008/0184386 A1    7/2008    Cao et al.

OTHER PUBLICATIONS

Buell et al, BMC Biology (2005) vol. 3 pp. 1-18.*
Gu et al (2008). High-resolution genetic mapping of bacterial blight resistance geneXa10. Theor Appl Genet 116: 155-163.*
Guo et al (2004), Proc. Natl. Acad. Sci. USA vol. 101 pp. 9205-9210.*
Ngo et al. in the Protein Folding Problem and Tertiary Structure Prediction, 1994, Merz et al. (ed.), Birkhauser, Boston, MA, pp. 491-495.*
Ge et al (Plant Cell Reports (2006) 25:392-402).*
Oña et al (Plant Disease (1998) 82:1337-1340).*
Gu, K. et al., "R Gene Expression Induced by a Type-III Effector Triggers Disease Resistance in Rice," Nature, Jun. 23, 2005, vol. 435, pp. 1122-1125.
Boch, J. et al., "Breaking the Code of DNA Binding Specificity of TAL-Type III Effectors," Science, Dec. 11, 2009, vol. 326, pp. 1509-1512.
Gu, K. et al., "Transcription Activator-Like Type III Effector AvrXa27 Depends on OsTFIIAg5 for the Activation of Xa27 Transcription in Rice that Triggers Disease Resistance to Xamthomonas oryzae pv. oryzae," Molecular Plant Pathology, vol. 10, No. 6, Dec. 31, 2009, pp. 829-835.
First Chinese Office Action with English Text and Search Report, Chinese Patent Application No. 201080069968.X; Jan. 6, 2014, 13 pages.
Hopkins, C.M., "Identification of a Family of Avirulence Genes From Xanthomonas Oryzae pv. Oryzae," Molecular Plant-Microbe Interactions, vol. 5, No. 6, pp. 451-459, 1992.

* cited by examiner

*Primary Examiner* — Shubo Joe Zhou
*Assistant Examiner* — Charles Logsdon
(74) *Attorney, Agent, or Firm* — Rothwell, Figg, Ernst & Manbeck, P.C.

(57) ABSTRACT

The present invention provides nucleic acids and methods for conferring resistance to bacterial disease in plants. The present invention also provides promoters and promoter sequences useful for controlling expression in transgenic plants.

32 Claims, 15 Drawing Sheets

MOLECULAR INTERACTION BETWEEN XA10 AND AVRXA10

CROSS-REFERENCE OF THE RELATED APPLICATION

The present application is a 35 U.S.C. §371 National Phase Entry Application of PCT/SG2010/000324, filed 6 Sep. 2010, and designating the United States, which is incorporated herein by reference.

SEQUENCE LISTING SUBMISSION

The present application is being filed along with a Sequence Listing in electronic format. The Sequence Listing is entitled 2577-204 Sequence ListingRev.txt, created on 3 May 2013 and is 73 kb in size. The information in the electronic format of the Sequence Listing is incorporated herein by reference in its entirety.

BACKGROUND OF THE INVENTION

The present invention relates generally to plant molecular biology and genetics and to nucleic acids and methods for conferring resistance to bacterial disease in plants. The present invention also relates to promoters and promoter sequences useful for controlling expression in transgenic plants.

The publications and other materials used herein to illuminate the background of the invention or provide additional details respecting the practice, are incorporated by reference, and for convenience are respectively grouped in the Bibliography.

Gram-negative phypathogenic bacteria employ a type III secretion system (TTSS) to translocate effector proteins into plant cells where they modulate host cell functions for the benefit of the invasion process (He et al., 2004). Pathovars of Xanthomonas and Ralstonia solanacearum harbor members of the large AvrBs3 effector family (Schornack et al., 2006; Heuer et al., 2007). AvrBs3-like effectors, also referred as transcription activator-like (TAL) type III effectors (Yang et al., 2006), are remarkably similar. Each possesses a central near-perfect repeats of a 34-amino acid sequence that vary in repeat number, imperfect heptad leucine zipper (LZ) repeats, three highly conserved C-terminal nuclear localization signals (NLS), and C-terminal acidic transcription activator-like domains (AAD). Several studies indicated that the TAL effectors from Xanthomonas oryzae pv. oryzae (Xoo) and Xanthomonas campestris pv. vesicatoria (Xcv) specifically activate the cognate host genes for promoting disease susceptibility (Yang et al., 2006; Sugio et al., 2007; Kay et al., 2007) or triggering disease resistance (Gu et al., 2005; Romer et al., 2007). The code of DNA binding specificity of TAL effectors was broken recently based on the detailed characterization of the conserved AvrBs3 binding sites in the promoters of the cognate Bs3 and upa genes from pepper (Capsicum annuum) as well as several other TAL effector binding sites (Kay et al., 2009; Romer et al., 2009a; Boch et al., 2009). According to the proposed model, each TAL effector repeat including the most C-terminal half repeat, which shows hypervariable amino acids at position 12 and 13, specifically recognizes a nucleotide in the DNA binding site of host gene promoter with a conserved T at the 5' end (Boch et al., 2009).

Bacterial blight of rice, caused by Xoo, is one of the most destructive bacterial diseases of rice, prevalently in irrigated and rainfed lowland rice growing areas throughout Asia (Mew, 1987). The utilization of host genetic resistance is the most economic and effective way to control this disease. Over 30 resistance (R) genes or loci with race-specific resistance to Xoo were identified in cultivated and wild rice (Nino-Liu et al., 2006). Six of them have been cloned and their gene products show great diversity (Chu et al. 2006; Gu et al. 2005; Iyer and McCouch, 2004; Song et al., 1995; Sun et al., 2004; Yoshimura et al., 1998). R gene Xa27 (Gu et al., 2005) and disease-susceptibility gene Os8N3 or the susceptible allele of the recessive R gene xa13 (Yang et al., 2006) were found to be specifically induced by TAL effectors AvrXa27 and PthXo1, respectively. The binding sites of the two TAL effectors in the promoters of their cognate host genes were identified recently (Romer et al., 2009b; Boch et al., 2009). A recent genetic study indicated that the general transcription factor OsTFIIAγ5 is required for AvrXa27 to fully activate Xa27 transcription in rice and Xa27-mediated disease resistance to bacterial blight (Gu et al. 2009).

The bacterial blight R gene Xa10 was originally identified from rice cultivar Cas 209 (Mew et al., 1982; Yoshimura et al., 1983) and was later introgressed into susceptible rice variety IR24 (Ogawa et al., 1988). The cognate avrXa10 gene from Xoo strain PXO86 encodes a member of TAL type-III effectors (Hopkins et al., 1992). The Xa10 locus was initially mapped to the long arm of chromosome 11 (11L) in the region between proximal RAPD marker O07$_{2000}$ (5.3 cM) and distal RFLP marker CDO365 (16.2 cM) (Yoshimura et al., 1995). It was recently mapped at genetic distance of 0.28 cM between proximal marker M491 and distal marker M419 and co-segregated with markers S723 and M604 (Gu et al., 2008).

Thus, it is desired to develop nucleic acids and methods for conferring resistance to bacterial disease in rice and other plants. It is also desired to develop isolated promoters or promoter sequences that can be used in genetic engineering of rice and other plant species.

SUMMARY OF THE INVENTION

The present invention relates generally to plant molecular biology and genetics and to nucleic acids and methods for conferring resistance to bacterial disease in plants. The present invention also relates to promoters and promoter sequences useful for controlling expression in transgenic plants. In accordance with the present invention, the cloning and characterization of a gene encoding the resistance gene Xa10, which confers resistance to bacterial blight disease is described. In one embodiment, the resistance is to bacterial blight disease caused by Xanthomonas species. In another embodiment, the plant is rice. In a further embodiment, the plant is barley, oats, wheat, corn, cabbage, broccoli, potato, tomato, pepper, chili, soybean or rapeseed.

Thus in a first aspect, the present invention provides an isolated nucleic acid encoding (i) the Xa10 polypeptide having the amino acid sequence set forth in SEQ ID NO:37 or (ii) a polypeptide having at least 50% identity to the Xa10 polypeptide in which the polypeptide of (ii) provides a plant with resistance to Xanthomonas when transfected into the plant. In one embodiment, the polypeptide of (ii) has at least 60% identity. In another embodiment, the polypeptide of (ii) has at least 70% identity. In an additional embodiment, the polypeptide of (ii) has at least 80% identity. In a further embodiment, the polypeptide of (ii) has at least 90% identity. In another embodiment, the polypeptide of (ii) has at least 95% identity. In an additional embodiment, the polypeptide of (ii) has at least 98% identity. In a further embodiment, the polypeptide of (ii) has at least 99% identity. In one embodiment, nucleic acid encoding the Xa10 polypeptide has the nucleotide sequence set forth in SEQ ID NO:35. In another embodiment, the nucleic acid encoding the Xa10 polypeptide has the nucleotide sequence set forth in SEQ ID NO:36. In an additional embodiment, the nucleic acid encoding the Xa10 polypeptide has the nucleotide sequence set forth in nucleotides 54-437 of SEQ ID NO:36. In a further embodiment, the nucleic acid encoding the Xa10 polypeptide has the nucleotide sequence set forth in nucleotides 2423-3234 of SEQ ID NO:35. In another embodiment, the isolated nucleic acid encoding (i) or (ii) may be operatively linked to a nucleic acid encoding a heterologous polypeptide, such as described herein. The present invention also provides Xa10 polypeptide described herein. In addition, the present invention provides a plant cell comprising the isolated nucleic acid and a transgenic plant resistant to *Xanthomonas* comprising the plant cell.

In a second aspect, the present invention provides a vector comprising an isolated nucleic acid encoding (i) the Xa10 polypeptide having the amino acid sequence set forth in SEQ ID NO:37 or (ii) a polypeptide having at least 50% identity to the Xa10 polypeptide in which the polypeptide of (ii) provides a plant with resistance to *Xanthomonas* when transfected into the plant described herein. In one embodiment, the vector further comprises a plant promoter operably linked to the isolated nucleic acid. In another embodiment, the promoter is selected from the group consisting of a tissue-specific promoter, a constitutive promoter and an inducible promoter. In an additional embodiment, promoter is selected from the group consisting of the Xa10 promoter having the nucleotide sequence set forth in SEQ ID NO:38, the Xa10 promoter having the nucleotide sequence set forth in nucleotides 1 through 2422 of SEQ ID NO:38 and the Xa10 promoter having the nucleotide sequence set forth in SEQ ID NO:39. In a further embodiment, promoter is selected from the group consisting of a promoter containing the AvrXa10 box having the nucleotide sequence set forth in SEQ ID NO:23 and promoters containing derivatives of the AvrXa10 box, wherein the derivatives of the AvrXa10 box are selected from the group consisting of a derivative having the nucleotide sequence set forth in SEQ ID NO:26, a derivative having the nucleotide sequence set forth in SEQ ID NO:28, a derivative having the nucleotide sequence set forth in SEQ ID NO:30, a derivative having the nucleotide sequence set forth in SEQ ID NO:31, a derivative having the nucleotide sequence set forth in SEQ ID NO:68, a derivative having the nucleotide sequence set forth in SEQ ID NO:72, a derivative having the nucleotide sequence set forth in SEQ ID NO:73, a derivative having the nucleotide sequence set forth in SEQ ID NO:74, a derivative having the nucleotide sequence set forth in SEQ ID NO:82, a derivative having the nucleotide sequence set forth in SEQ ID NO:83, a derivative having the nucleotide sequence set forth in SEQ ID NO:84 and a derivative having the nucleotide sequence set forth in SEQ ID NO:85. The present invention also provides a plant cell comprising the vector and a transgenic plant resistant to *Xanthomonas* comprising the plant cell. In another embodiment, the isolated nucleic acid encoding (i) or (ii) in the vector may be operatively linked to a nucleic acid encoding a heterologous polypeptide, such as described herein.

In a third aspect, the present invention provides methods of (i) making a plant resistant to *Xanthomonas*, (b) enhancing resistance to *Xanthomonas* in a plant and (c) conferring resistance to *Xanthomonas* disease to a plant. Each of these methods comprises transfecting the isolated nucleic acid described herein or the vector described herein into a plant cell or plant cells and growing a plant from the transfected plant cell or transfected plant cells, wherein the isolated nucleic acid is expressed in the plant. Transfecting the nucleic acid or vector into a plant cell or cells is also sometimes referred to herein as transforming a plant cell or cells with the nucleic acid or vector.

In a fourth aspect, the present invention provides an isolated nucleic acid having promoter activity in a plant. In one embodiment, the nucleic acid has the nucleotide sequence set forth in SEQ ID NO:38 or the nucleotide sequence set forth in nucleotides 1 to 2422 of SEQ ID NO:38. In another embodiment, the nucleic acid has the nucleotide sequence set forth in SEQ ID NO:39. In a runner embodiment, the nucleic acid comprising a plant operable promoter containing the nucleotide sequence set forth in SEQ ID NO:23. In another embodiment, the nucleic acid comprising a plant operable promoter containing the nucleotide sequence set forth in SEQ ID NO:26. In an additional embodiment, the nucleic acid comprising a plant operable promoter containing the nucleotide sequence set forth in SEQ ID NO:28. In a further embodiment, the nucleic acid comprising a plant operable promoter containing the nucleotide sequence set forth in SEQ ID NO:30. In another embodiment, the nucleic acid comprising a plant operable promoter containing the nucleotide sequence set forth in SEQ ID NO:31. In an additional embodiment, the nucleic acid comprising a plant operable promoter containing the nucleotide sequence set forth in SEQ ID NO:68. In a further embodiment, the nucleic acid comprising a plant operable promoter containing the nucleotide sequence set forth in SEQ ID NO:72. In another embodiment, the nucleic acid comprising a plant operable promoter containing the nucleotide sequence set forth in SEQ ID NO:73. In a further embodiment, the nucleic acid comprising a plant operable promoter containing the nucleotide sequence set forth in SEQ ID NO:74. In another embodiment, the nucleic acid comprising a plant operable promoter containing the nucleotide sequence set forth in SEQ ID NO:82. In an additional embodiment, the nucleic acid comprising a plant operable promoter containing the nucleotide sequence set forth in SEQ ID NO:83. In a further embodiment, the nucleic acid comprising a plant operable promoter containing the nucleotide sequence set forth in SEQ ID NO:84. In another embodiment, the nucleic acid comprising a plant operable promoter containing the nucleotide sequence set forth in SEQ ID NO:85. The present invention also provides a nucleic acid construct comprising the nucleic acid having promoter activity operably linked to a second nucleic acid encoding a nucleic acid of interest. In addition, the present invention provides a transgenic plant cell or a transgenic plant containing the nucleic acid construct in its genome. The present invention further provides a method of producing the transgenic plant cell or transgenic plant. The transgenic plant cell is produced by transfecting the nucleic acid construct into a plant cell or cells. The transgenic plant is produced by regenerating a plant from the transfected plant cell or cells.

In a fifth aspect, the present invention provides uses and methods to control gene expression in transgenic plants. In one embodiment, the isolated nucleic acid having promoter activity described herein is used to control gene expression in a transgenic plant. In another embodiment, a nucleic acid encoding the AvrXa10 polypeptide having the amino acid sequence set forth in SEQ ID NO:54 is used to control gene expression in a transgenic plant containing the isolated nucleic acid having promoter activity described herein. In a further embodiment, the AvrXa10 polypeptide having the amino acid sequence set forth in SEQ ID NO:54 is used to control gene expression in a transgenic plant containing the isolated nucleic acid having promoter activity described herein. In one embodiment, the nucleic acid encoding the AvrXa10 polypeptide has the nucleotide sequence set forth in SEQ ID NO:57. In another embodiment, the nucleic acid encoding the AvrXa10 polypeptide has the nucleotide sequence set forth in GenBank Accession No. U50552.

BRIEF DESCRIPTION OF THE FIGURES

FIG. 1A: Genetic and physical maps at the Xa10 locus. The upper part is the genetic map of the Xa10 locus resolved using molecular markers M491, S723 and M419 as presented previously by Gu et al. (2008). 44M10 is the BAC clone that was identified by markers M491 and S723. Subclones of 44M10 in binary vector pC1300 used for complementation test are shown below. Vertical lines link the genetic locations of M491 and the Xa10 locus to their positions at the physical map. Subclones that produced bacterial blight (BB)-resistant transgenic plants are indicated with "+", otherwise, they are marked with "–". The position of the Xa10 gene is indicated with short bold line with arrowhead standing for the direction of transcription. FIG. 1B: Phenotypes of wild-type and transgenic plants at two weeks after inoculation with *Xanthomonas oryzae* pv *oryzae* (Xoo) strains. L1, IR24 inoculated with PXO99; L2, IR24 inoculated with PXO99(pHM1avrXa10); L3, IRBB10A inoculated with PXO99; L4, IRBB10A inoculated with PXO99(pHM1avrXa10); L5, Nipponbare inoculated with PXO99; L6, Nipponbare inoculated with PXO99 (pHM1avrXa10); L7, Xa10 transgenic line L198 inoculated with PXO99; L8, L198 inoculated with PXO99 (pHM1avrXa10). FIG. 1C: Gene structure of the Xa10 gene. The coding region (black bar), the position of 5' and 3' UTR (hatched box), translation start codon (ATG), translation stop codon (TGA), 5' and 3' splice junctions (ga and cg) are indicated. The numbers indicate the base pairs of each substructure. FIG. 1D: Predicted amino acid sequence of the Xa10 gene (SEQ ID NO:37). The predicted signal peptide is underlined.

FIG. 2 shows detection of the Xa10 gene in different rice cultivars. About 5 μg of rice genomic DNA was digested with HindIII and used for Southern blot analysis in each lane. The Southern filter was detected with a probe from Xa10 coding region using primers SP1F and SP1R. M, DNA marker of Lambda DNA digested with HindIII.

FIGS. 3A and 3B show ectopic expression of Xa10 provided enhanced resistance to compatible *Xanthomonas oryzae* pv *oryzae* strains. FIG. 3A: Phenotypes of IRBB10A and transgenic plants at two weeks after inoculation with Xoo strains. L1, IRBB10A inoculated with PXO99; L2, IRBB10A inoculated with PXO99(pHM1avrXa10); L3, Nipponbare inoculated with PXO99; L4, Nipponbare inoculated with PXO99(pHM1avrXa10); L5, Transgenic line L198 inoculated with PXO99; L6, Transgenic line L198 inoculated with PXO99(pHM1avrXa10); L7, Transgenic line L162 inoculated with PXO99; L8, Transgenic line L162 inoculated with PXO99(pHM1avrXa10). FIG. 3B: Real-time PCR analysis of Xa10 in uninoculated and inoculated plants. The expression of rice Ubiquitin 1 gene was used as an internal control. Results are shown as the relative values normalized to IRBB10A inoculated with PXO99 (pHM1avrXa10) at 12 hours after inoculation (HAI). The primers for Xa10 were 10RT F2 and 10RT R2, and the primers for rice Ubiquitin 1 gene were RBQ3 and RBQ4. UI, uninoculated plants; "–", plants infiltrated with PXO99 at 12 HAI; "+", plants infiltrated with PXO99(pHM1avrXa10) at 12 HAI.

FIGS. 4A and 4B show the prediction of transmembrane helices in XA10. FIG. 4A: Output of prediction of transmembrane regions in XA10 from "DAS"—Transmembrane Prediction server (http colon//www dot sbc dot su dot se~miklos/DAS/). FIG. 4B: Output of prediction of transmembrane helices in XA10 from TMHMM Server v. 2.0 (http colon//www dot cbs dot dtu dot dk/services/TMHMM/).

FIGS. 5A and 5B show the prediction of signal peptide at N-terminal region of XA10. Signal peptide in amino acid sequences of XA10 was predicted by both SignalP-NN prediction (FIG. 5A) and SignalP-HMM prediction (FIG. 5B). The cleavage site of signal peptide is located at position between 29 and 30. The full length amino acid sequence of XA10 was submitted to the SignalP 3.0 server (http colon//www dot cbs dot dtu dot dk/services/SignalP/) for the prediction of signal peptides of eukaryotes. Methods of both neural networks and hidden Markov models were used for prediction. Standard output format was selected. The amino acid sequence in FIGS. 5A and 5B consists of amino acids 1-70 of SEQ ID NO:37.

FIGS. 6A-6C show specific induction of Xa10 by AvrXa10 from *Xanthomonas oryzae* pv. *oryzae*. FIG. 6A: Induction of Xa10 in IRBB10A at different hours after inoculation (HAI) with Xoo strain PXO99(pHM1avrXa10). The expression of rice Ubiquitin 1 gene in leaves was used as an internal control. FIG. 6B: Real-time PCR analysis of Xa10 transcripts in IRBB10A measured at different HAI after inoculation with Xoo strain PXO99(pHM1avrXa10). The expression of rice Ubiquitin 1 gene in leaves was used as an internal control. Results are shown as the relative values of expression of Xa10 over that of rice Ubiquitin 1 gene. The primers for Xa10 were 10RT F2 and 10RT R2, and the primers for rice Ubiquitin 1 gene were RBQ3 and RBQ4. FIG. 6C: Induction of Xa10 in IRBB10A at 12 HAI with Xoo strain PXO99 expressing AvrXa10 or its mutants. UI, uninoculated IRBB10A; PXO99, IRBB10A inoculated with PXO99; PXO99/AvrXa10, IRBB10A inoculated with PXO99(pHM1avrXa10); PXO99/AvrXa10NLS, IRBB10A inoculated with PXO99 (pHM1avrXa10NLS); PXO99/AvrXa10AD, IRBB10A inoculated with PXO99 (pHM1avrXa10AD).

FIGS. 7A-7D show that induction of Xa10 by AvrXa10 requires rice transcriptional factor OsTFIIAγ5. FIG. 7A: Phenotype of bacterial blight disease of rice lines at two weeks after inoculation with Xoo strain PXO99 (pHM1avrXa10). L1, IRBB5; L2, IRBB10A; L3, double homozygote (Xa10Xa10xa5xa5) of IRBB5×IRBB10A. FIG. 7B: Bacterial population in leaves of IRBB5, IRBB10A and double homozygote over 14 days by leaf-clipped inoculation with PXO99(pHM1avrXa10). FIG. 7C: Expression of Xa10 in IRBB5, IRBB10A and double homozygote. mRNA for northern blot analysis was isolated from uninoculated plants (0 hour after inoculation or 0 HAI) or plants infiltrated with PXO99(pHM1avrXa10) at 12 HAI (12 HAI). FIG. 7D: Transcript levels of Xa10 in IRBB5, IRBB10A and double homozygote. Transcript levels were measured by real-time PCR. Total RNA was isolated from uninoculated plants (0 HAI) or plants infiltrated with PXO99 (pHM1avrXa10) at 12 HAI (12 HAI). The expression of rice Ubiquitin 1 gene was used as an internal control. Results are shown as the relative values of expression of Xa10 over that of rice Ubiquitin 1 gene. The primers for Xa10 were 10RT F2 and 10RT R2, and the primers for rice Ubiquitin 1 gene were RBQ3 and RBQ4.

FIG. 8A: AvrXa10 contain central tandem repeats, nuclear localization signals (NLSs), and an acidic transcriptional activation domain (AD). FIG. 8B: Hypervariable amino acids at position 12 and 13 of the 15.5 AvrXa10 repeats are shown. "–" indicates that amino acid 13 is missing in this repeat. FIG. 8C: Nucleotide sequences of Xa10 promoter (−220 to ATG) (SEQ ID NO:41) and AvrXa10 box candidates. AvrXa10 box candidates (Box 1 to Box 12) were predicted based on the model for DNA-target specificity of TAL effectors (Boch et al., 2009). In each candidate, nucleotides that match the model are indicated with capital letters; otherwise, they are displayed in lower letters. Transcriptional initiation site of Xa10 is marked with "+1". The 5' untranslated region (5'UTR) is shown in italics and the start codon of Xa10 is underlined. The Xa10 promoter sequence (−220 to ATG) shown in the lines marked −220, −215, −177, −139, −110, −72, −36, +1 and +39 is SEQ ID NO:41. The remaining sequences are as follows: Box 1: SEQ ID NO:16; Box 4: SEQ ID NO:19; Box 7: SEQ ID NO:22; Box 10: SEQ ID NO:25; Box 2: SEQ ID NO:17; Box 5: SEQ ID NO:20; Box 8: SEQ ID NO:23; Box 11: SEQ ID NO:26; Box 3: SEQ ID NO:18; Box 6: SEQ ID NO:21; Box 9: SEQ ID NO:24; and Box 12: SEQ ID NO:27.

FIG. 9A: Schematic map of GUS reporter constructs. FIG. 9B: DNA sequence between GATEWAY recombination sites in the GUS reporter constructs. AvrXa10 box candidates were inserted in the "TAL effector box" position at the 5' of the minimal tomato Bs4 promoter (pBs4; −50 to +25) sequence (Boch et al., 2009) and transferred by GATEWAY recombination into the *A. tumefaciens* T-DNA vector pCGWGUS-int constructing a fusion to a promoterless intron-containing β-glucuronidase (GUSPlus) gene. attB1 and attB2, GATEWAY recombination sites; promoterless GUSPlus-Tnos, coding sequence of GUSPlus (including intron) and terminator of nopaline synthase (nos) gene from pC1305.1; LB, left border; RB, right border. Upstream pENTER/D-TOPO sequence between "attB1" and "TAL effector-box" is SEQ ID NO:42. The sequence between "TAL effector-box" and "attB2" is SEQ ID NO:43.

FIG. 10A: AvrXa10 box and its derivatives. FIG. 10B: Specific inducibility of the AvrXa10 boxes by AvrXa10. GUS reporter constructs codelivered via *A. tumefaciens* into *N. benthamiana* leaf cells with 35S-driven avrXa10 (+), and empty T-DNA vector (−), respectively (error bars indicate SD; n=3 samples). 35S::GUSPlus in pC1305.1 (p35S) served as control. For qualitative assays, leaf discs were stained with X-Gluc (5-bromo-4-chloro-3-indolyl-β-D-glucuronide). For quantitative assay, the GUS activity was detected using MUG (4-methyl-umbelliferyl-β-D-glucuronide) as substrate. 4-MU, 4-methyl-umbelliferone. The sequences are as follows: pXa10-220: SEQ ID NO:39; AvrXa10 box (Box 8): SEQ ID NO:23; Box 8 0dT: SEQ ID NO:40; Box 5: SEQ ID NO:20; Box 11: SEQ ID NO:26; Box 8 d15: SEQ ID NO:28; Box 8 d14: SEQ ID NO:30; Box 8 d13: SEQ ID NO:31; Box 8 d12: SEQ ID NO:32; and Box 8 d11: SEQ ID NO:33.

FIG. 11A: Hypervariable amino acids 12 and 13 of AvrXa10 and AvrXa27 and their target DNA specificities. AvrXa10 box (SEQ ID NO:23) and AvrXa27 box (Boch et al., 2009; Romer et al., 2009a) (SEQ ID NO:44) were cloned in front of the minimal Bs4 promoter into a intron-containing GUS (GUSPlus) reporter vector. FIG. 11B: Specific inducibility of the AvrXa10 box and AvrXa27 box by AvrXa10 and AvrXa27. GUS reporter constructs codelivered via *A. tumefaciens* into *N. benthamiana* leaf cells with 35S-driven avrXa10 (AvrXa10), avrXa27 (AvrXa27), and empty T-DNA vector (−), respectively (error bars indicate SD; n=3 samples). 35S::GUSPlus served as control. For qualitative assays, leaf discs were stained with X-Gluc (5-bromo-4-chloro-3-indolyl-β-D-glucuronide). For quantitative assay, the GUS activity was detected using MUG (4-methyl-umbelliferyl-β-D-glucuronide) as substrate. 4-MU, 4-methyl-umbelliferone.

FIG. 12A: Yeast growth on selective medium for yeast one-hybrid assay. Four tandem copies of the AvrXa10 box and AvrXa27 box in sense (4× AvrXa10 box and 4× AvrXa27 box) were used as baits, respectively. AvrXa10 and AvrXa27 fused to SV40 NLS-GAL4 AD were used as prey, respectively. The GAL4-AD fusion of murine p53 protein and a bait containing its target sequence (p53DBS) served as controls. 50 µl of serial dilutions of single transformants in SD liquid medium ($10^{-2}$, $10^{3}$, $10^{-4}$, $10^{-5}$) were dropped on SD medium containing either leucine (L) or 200 ng/ml aureobasidin A (AbA200). Two transformants per experiment were analyzed. The experiment was repeated twice with similar results. FIG. 12B: Yeast colony PCR using oligonucleotides pAbAi F2 and pAbAi R2 to verify the inserts of bait plasmids (AvrXa10 box: 1418 bp; AvrXa27 box: 1422 bp; p53 DBS: 1400 bp). FIG. 12C: Western blot showing GAL4-AD fusion prey proteins using an α-GAL4 AD antibody. SV40 NLS-GAL4 AD-HA fusions to AvrXa10 (135 kDa), AvrXa27 (139 kDa) and p53 (61 kDa).

FIG. 14A: DNA sequences of AvrXa10 box probe (SEQ ID NO:34) and AvrXa27 box probe (SEQ ID NO:45) used in EMSA. The AvrXa10 box and AvrXa27 box in the probes are in bold letters. FIG. 14B: AvrXa10 binds with high affinity to the AvrXa10 box probe, whereas AvrXa27 binds with high affinity to both AvrXa10 box and AvrXa27 box probes. EMSA with AvrXa10 or AvrXa27 and biotin-labeled AvrXa10 box or AvrXa27 box probes was separated in a 6% nondenaturing polyacrylamide gel. FIG. 14C: Binding of AvrXa10 to AvrXa10 box probe can be out-competed by cold AvrXa10 box probe but not by cold AvrXa27 box probe. Competition experiment between biotin-labeled AvrXa10 box probe and different amounts (in fmol) of nonlabeled competitor probes was separated in 6% nondenaturing polyacrylamide gel. FIG. 14D: Binding of AvrXa27 to AvrXa10 box or AvrXa27 box probes was highly out-competed by cold AvrXa27 box probe. Competition experiment between biotin-labeled AvrXa10 box or AvrXa27 box probes and different amounts (in finol) of nonlabeled competitor probes was separated in a 6% nondenaturing polyacrylamide gel. Positions of the bound and free probes are indicated on the left.

FIG. 15A: DNA sequences of probes of AvrXa10 box and its deletion mutants used in EMSA. FIG. 15B: Specific inducibility of AvrXa10 box and its deletion mutants by AvrXa10. GUS reporter constructs codelivered via *A. tumefaciens* into *N. benthamiana* leaf cells with 35S-driven avrXa10 (+), and empty T-DNA vector (−), respectively (error bars indicate SD; n=3 samples). 35S::GUSPlus in pC1305.1 (p35S) served as control. The quantitative GUS activity was detected using MUG (4-methyl-umbelliferyl-β-D-glucuronide) as substrate. 4-MU, 4-methyl-umbelliferone. FIG. 15C: AvrXa10 binds with high affinity to some probes of the AvrXa10 box deletion mutants. EMSA with AvrXa10 and biotin-labeled probes of AvrXa10 box or its deletion mutants was separated in a 6% nondenaturing polyacrylamide gel. About 200 ng of AvrXa10 was used for EMSA. Positions of the bound (indicated with a dart) and free probes are shown on the left. The sequences are as follows: AvrXa10 box: SEQ ID NO:34; Box 8 0dT: SEQ ID NO:46; Box 8 1dA: SEQ ID NO:47; Box 8 2dT: SEQ ID NO:48; Box 8 3dA: SEQ ID NO:49; Box 8 4dT: SEQ ID NO:50; Box 8 5dA: SEQ ID NO:51; Box 8 6dC: SEQ ID NO:52; Box 8 7dA: SEQ ID NO:53; Box 8 8dC: SEQ ID NO:58; Box 8 9dA: SEQ ID NO:59; Box 8 10dC: SEQ ID NO:60; Box 8 11dG: SEQ ID NO:61; Box 8 12dT: SEQ ID NO:62; Box 8 13dT: SEQ ID NO:63; Box 8 14dC: SEQ ID NO:64; Box 8 15dA: SEQ ID NO:65; and Box 8 16dC: SEQ ID NO:66.

FIG. 16A: DNA sequences of probes of AvrXa10 box, Box 7 and their mutants used in EMSA. The mutated bases are in bold letters. FIG. 16B: Specific inducibility of AvrXa10 box, Box 7 and their mutants by AvrXa10. GUS reporter constructs codelivered via *A. tumefaciens* into *N. benthamiana* leaf cells with 35S-driven avrXa10 (+) and empty T-DNA vector (−), respectively (error bars indicate SD; n=3 samples). 35S::GUSPlus served as control. For qualitative assays, leaf discs were stained with X-Gluc (5-bromo-4-chloro-3-indolyl-β-D-glucuronide). The quantitative GUS activity was detected using MUG (4-methyl-umbelliferyl-β-D-glucuronide) as substrate. 4-MU, 4-methyl-umbelliferone. The sequences are as follows: AvrXa10 box: SEQ ID NO:23; Box 8M1: SEQ ID NO:67; Box 7: SEQ ID NO:22; Box 7M: SEQ ID NO:68; Box 7M1: SEQ ID NO:69; Box 7M2: SEQ ID NO:70; Box 7M3: SEQ ID NO:71; Box 7M4: SEQ ID NO:72; Box 7M5: SEQ ID NO:73; and Box 7M6: SEQ ID NO:74.

FIG. 17A: DNA sequences of probes of AvrXa10 box, Box 7 and their mutants used in EMSA. FIG. 17B: AvrXa10 binds with high affinity to the probes of AvrXa10 box, Box 7 and their mutants. EMSA with AvrXa10 and biotin-labeled AvrXa10 box, Box 7 or their mutant probes was separated in a 6% nondenaturing polyacrylamide gel. FIG. 17C: Binding of AvrXa10 to AvrXa10 box probe is out-competed by cold probes of AvrXa10 box, Box 8M1, Box 7 or Box 7M. Competition experiment between AvrXa10 box and different amounts (in fmol) of nonlabeled competitor probes was separated in a 6% nondenaturing polyacrylamide gel. FIG. 17D: Binding of AvrXa10 to probes of Box 8M1, Box 7 or Box 7M is out-competed by cold AvrXa10 box probe. Competition experiment between Box 8M1, Box 7 or Box 7M and different amounts (in fmol) of nonlabeled competitor probes was separated in a 6% nondenaturing polyacrylamide gel. Positions of the bound and free probes are indicated on the left. The sequences are as follows: AvrXa10 box: SEQ ID NO:34; Box 8M1: SEQ ID NO:75; Box 7: SEQ ID NO:76; and Box 7M: SEQ ID NO:77.

FIG. 18A: Yeast growth on selective medium for yeast one-hybrid assay. Four tandem copies of Box 7, AvrXa10 box or their mutants in sense (4× Box 7, 4× Box 7M, 4× AvrXa10 box and 4× Box 8M1) were used as baits. AvrXa10 fused to SV40 NLS-GAL4 AD was used as prey. The GAL4-AD fusion of murine p53 protein and a bait containing its target sequence (p53 DBS) served as controls. 50 μl of serial dilutions of single transformants in SD liquid medium ($10^{-2}$, $10^{-3}$, $10^{-4}$, $10^{-5}$) were dropped on SD medium containing either leucine (+L) or 200 ng/ml aureobasidin A (+AbA200). Two transformants per experiment were analyzed. The experiment was repeated twice with similar results. FIG. 18B: Yeast colony PCR using primers pAbAi F2 and pAbAi R2 to verify the inserts of bait plasmids (Box 7: 1418 bp; Box 7M: 1418 bp; AvrXa10 box: 1418 bp; Box 8M1: 1422 bp; p53 DBS: 1400 bp). FIG. 18C: Western blot showing GAL4-AD fusion prey proteins using an anti-GAL4 AD antibody. SV40 NLS-GAL4 AD-HA fusions to AvrXa10 (135 kDa) and p53 (61 kDa).

DETAILED DESCRIPTION OF THE INVENTION

Figure 1:
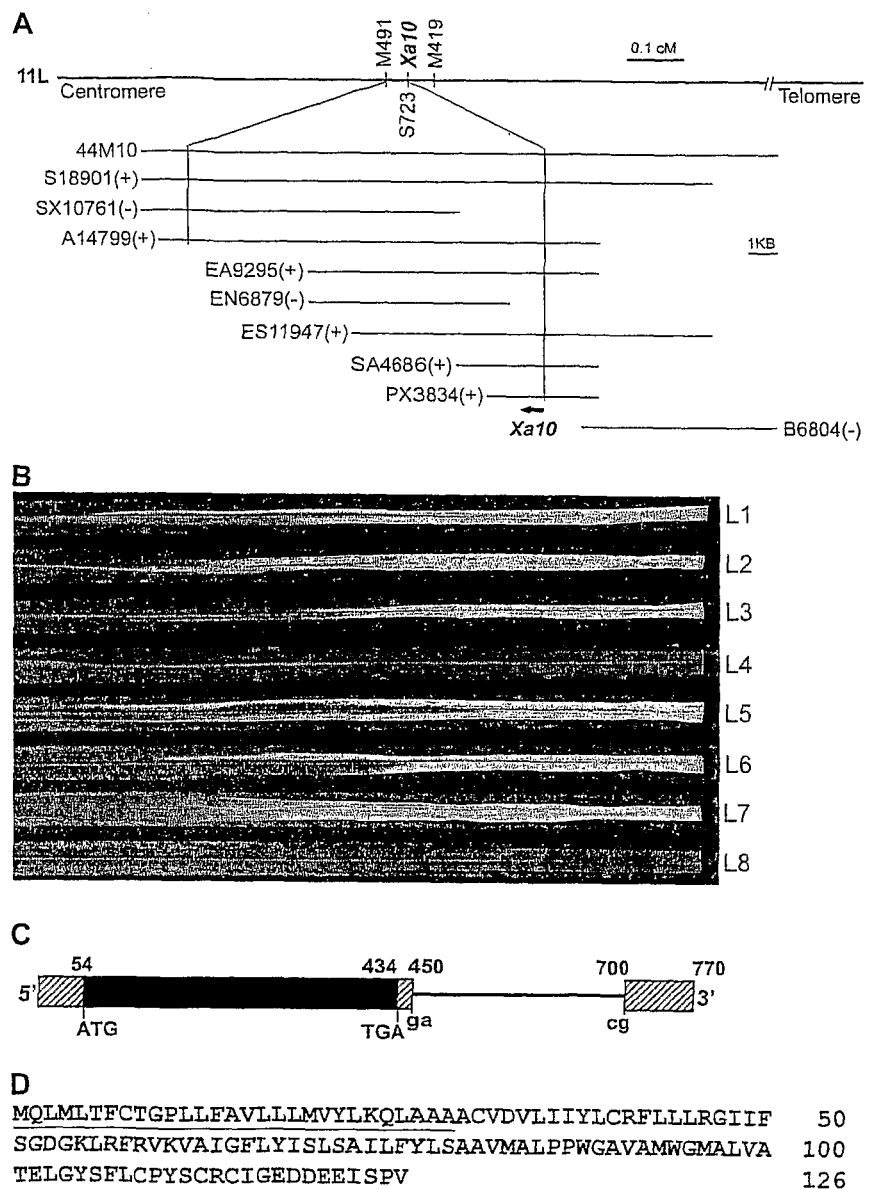
FIGS. 1A-1D show map-based cloning of the Xa10 gene.

The present invention relates generally to plant molecular biology and genetics and to nucleic acids and methods for conferring resistance to bacterial disease in plants. The present invention also relates to promoters and promoter sequences useful for controlling expression in transgenic plants. In accordance with the present invention, the cloning and characterization of a gene encoding the resistance gene Xa10, which confers resistance to bacterial blight disease is described. In one embodiment, the resistance is to bacterial blight disease caused by *Xanthomonas* species. In another embodiment, the plant is rice. In a further embodiment, the plant is barley, oats, wheat, corn, cabbage, broccoli, potato, tomato, pepper, chili, soybean or rapeseed.

Transcription activator-like (TAL) type III effectors of *Xanthomonas* spp contribute to pathogenesis by targeting to host gene promoters and activating host gene expression. In accordance with the present invention, the isolation of rice bacterial blight resistance gene Xa10 and the characterization of the molecular recognition between Xa10 and TAL type III effector AvrXa10 from *Xanthomonas oryzae* pv. *oiyzae* (Xoo) is described. As described herein the Xa10 gene was isolated from Xa10-containing rice line by positional cloning strategy and genetic transformation. The Xa10 gene encodes an unknown transmembrane protein. Xa10 was specifically induced by Xoo strains that harbor the AvrXa10 gene. Mutation of the nuclear localization signal (NLS) motifs in AvrXa10 or deletion of the transcription activation domain (AD) at its C-terminal region abolished its function for Xa10 activation. The activation of Xa10 expression by AvrXa10 requires rice transcriptional factor OsTFIIAγ5. A 17-bp AvrXa10 box was identified in the Xa10 promoter by candidate approach. The AvrXa10 box was specifically recognized by AvrXa10 in *Nicotiana benthamiana* in transient assay and this recognition activated reporter gene expression. The specific interaction of AvrXa10 box and AvrXa10 was further confirmed in yeast by yeast-one-hybrid assay and in vitro by electromobility shift assay (EMSA). Deletion of any one of the nucleotides at the positions 0 to 11 impaired AvrXa10 box activity. Deletion of any one of the first four nucleotides (TATA) in the AvrXa10 box also abolished the binding of AvrXa10 to the mutant probes in EMSA, indicating that the first four nucleotides in the AvrXa10 box are essential for the binding of AvrXa10 to the Xa10 promoter. Deletion of any one of the nucleotides at positions 13 to 17 did not affect the AvrXa10 box activity, nor did the binding of AvrXa10 to the mutant probes in EMSA. Deletion of the last four nucleotides at positions 13 to 17 in AvrXa10 box also did not significantly affect AvrXa10 box activity for induction of reporter gene by AvrXa10. The nucleotides "CAC" at the positions from 9 to 11 in AvrXa10 box was essential for activation of transcription by AvrXa10. Mutation of the "CAC" to "TCA" completely abolished AvrXa10 box activity, whereas change of "TCA" in Box 7 to "CAC" gained AvrXa10 box activity for the mutated Box 7 (Box 7M). These results indicated that AvrXa10 box may have two functional centers: the first four nucleotides (TATA) as the AvrXa10 binding center and the transcription activation center at positions 9 to 11 (CAC). The identification of molecular interaction between Xa10 and AvrXa10, together with other host genes identified to be targeted by TAL type III effectors, enables the engineering of broad-spectrum and durable resistance to bacterial diseases caused by *Xanthomonas* spp.

As used herein, the term "plant cell" is intended to encompass any cell derived from a plant including undifferentiated tissues such as callus and suspension cultures, as well as plant seeds, pollen or plant embryos. Plant tissues suitable transformation include leaf tissues, root tissues, meristems, protoplasts, hypocotyls, cotyledons, scutellum, shoot apex, root, immature embryo, pollen, and anther. Some non-limiting examples of methods that can be employed in transforming plants and plant cells are described herein. Examples of plants contemplated for the present invention include rice, barley, oats, wheat, corn, cabbage, broccoli, potato, tomato, pepper, chili, soybean, rapeseed and any other plant that is susceptible to *Xanthomonas*.

A polynucleotide or nucleic acid is said to "encode" a polypeptide if, in its native state or when manipulated by methods well known to those skilled in the art, it can be transcribed and/or translated to produce the mRNA for and/or the polypeptide or a fragment thereof.

An "isolated" or "substantially pure" nucleic acid (e.g., an RNA, DNA or a mixed polymer) or polypeptide is one which is substantially separated from other cellular components which naturally accompany a native human sequence or protein, e.g., ribosomes, polymerases, many other human genome sequences and proteins. The term embraces a nucleic acid sequence or protein that has been removed from its naturally occurring environment, and includes recombinant or cloned DNA isolates and chemically synthesized analogs or analogs biologically synthesized by heterologous systems.

The polynucleotide compositions of this invention include RNA, cDNA, genomic DNA, synthetic forms, and may be chemically or biochemically modified or may contain non-natural or derivatized nucleotide bases, as will be readily appreciated by those skilled in the art. Such modifications include, for example, labels, methylation, substitution of one or more of the naturally occurring nucleotides with an analog, internucleotide modifications such as uncharged linkages (e.g., methyl phosphonates, phosphotri- esters, phosphoramidates, carbamates, etc.), charged linkages (e.g., phosphorothioates, phosphorodithioates, etc.), pendent moieties (e.g., polypeptides), intercalators (e.g., acridine, psoralen, etc.), chelators, alkylators, and modified linkages (e.g., alpha anomeric nucleic acids, etc.). Also included are synthetic molecules that mimic polynucleotides in their ability to bind to a designated sequence via hydrogen bonding and other chemical interactions. Such molecules are known in the art and include, for example, those in which peptide linkages substitute for phosphate linkages in the backbone of the molecule. The polynucleotides of the invention may be isolated or substantially pure.

The present invention provides recombinant nucleic acids. The recombinant construct may be capable of replicating autonomously in a host cell. Alternatively, the recombinant construct may become integrated into the chromosomal DNA of the host cell. Such a recombinant polynucleotide comprises a polynucleotide of genomic, cDNA, semi-synthetic, or synthetic origin which, by virtue of its origin or manipulation, 1) is not associated with all or a portion of a polynucleotide with which it is associated in nature; 2) is linked to a polynucleotide other than that to which it is linked in nature; or 3) does not occur in nature. Therefore, recombinant nucleic acids comprising sequences otherwise not naturally occurring are provided by this invention. Although the described sequences may be employed, it will often be altered, e.g., by deletion, substitution or insertion.

"Protein modifications or fragments" are provided by the present invention for wildtype and mutant polypeptides described herein or fragments thereof which are substantially homologous to primary structural sequence but which include, e.g., in vivo or in vitro chemical and biochemical modifications or which incorporate unusual amino acids. Such modifications include, for example, acetylation, carboxylation, phosphorylation, glycosylation, ubiquitination, labeling, e.g., with radionuclides, and various enzymatic modifications, as will be readily appreciated by persons of ordinary skill in the art. A variety of methods for labeling polypeptides and of substituents or labels useful for such purposes are well known by persons of ordinary skill in the art, and include radioactive isotopes such as $^{32}$P, ligands which bind to labeled antiligands (e.g., antibodies), fluorophores, chemiluminescent agents, enzymes, and antiligands which can serve as specific binding pair members for a labeled ligand. The choice of label depends on the sensitivity required, ease of conjugation with the primer, stability requirements, and available instrumentation.

Besides substantially full-length proteins, the present invention provides for biologically active fragments of the polypeptides. Significant biological activities include ligand-binding, immunological activity and other biological activities characteristic of proteins. The term "polypeptide" as used herein refers to both a full length protein and a portion of the protein as a polypeptide fragment. A polypeptide "fragment," "portion" or "segment" is a stretch of amino acid residues eat least about five to seven contiguous amino acids, often at least about seven to nine contiguous amino acids, typically at least about nine to 13 contiguous amino acids and, most preferably, at least about 20 to 30 or more contiguous amino acids.

The present invention also provides for fusion polypeptides, comprising the polypeptides described herein and fragments thereof and polypeptides or fragments of other proteins as known in the art. Homologous polypeptides may be fusions between two or more polypeptide sequences or between the sequences described herein and a related protein. Likewise, heterologous fusions may be constructed which would exhibit a combination of properties or activities of the derivative proteins. For example, ligand-binding or other domains may be "swapped" between different new fusion polypeptides or fragments. Such homologous or heterologous fusion polypeptides may display, for example, altered strength or specificity of binding and may include for example partners such as immunoglobulins, bacterial β-galactosidase, trpE, protein A, β-lactamase, alpha amylase, alcohol dehydrogenase and yeast alpha mating factor. Fusion proteins will typically be made by either recombinant nucleic acid methods, as described below, or may be chemically synthesized. Techniques for the synthesis of polypeptides are well known by persons of ordinary skill in the art.

Other protein modifications include amino acid substitution. Substitutional variants typically contain the exchange of one amino acid for another at one or more sites within the protein, and may be designed to modulate one or more properties of the polypeptide, such as stability against proteolytic cleavage, without the loss of other functions or properties. Amino acid substitutions may be made on the basis of similarity in polarity, charge, solubility, hydrophobicity, hydrophilicity, and/or the amphipathic nature of the residues involved. Preferred substitutions are ones which are conservative, that is, one amino acid is replaced with one of similar shape and charge. Conservative substitutions are well known to persons of ordinary skill in the art and typically include, though not exclusively, substitutions within the following groups: glycine, alanine; valine, isoleucine, leucine; aspartic acid, glutamic acid; asparagine, glutamine; serine, threonine; lysine, arginine; and tyrosine, phenylalanine.

Certain amino acids may be substituted for other amino acids in a protein structure without appreciable loss of interactive binding capacity with structures such as, for example, antigen-binding regions of antibodies or binding sites on substrate molecules or binding sites on proteins interacting with a polypeptide. Since it is the interactive capacity and nature of a protein which defines that protein's biological functional activity, certain amino acid substitutions can be made in a protein sequence, and its underlying DNA coding sequence, and nevertheless obtain a protein with like properties. In making such changes, the hydropathic index of amino acids may be considered. The importance of the hydrophobic amino acid index in conferring interactive biological function on a protein is generally understood in the art. Alternatively, the substitution of like amino acids can be made effectively on the basis of hydrophilicity. The importance of hydrophilicity in conferring interactive biological function of a protein is generally understood in the art (See e.g. U.S. Pat. No. 4,554,101). The use of the hydrophobic index or hydrophilicity in designing polypeptides is further discussed in U.S. Pat. No. 5,691,198.

"Recombinant nucleic acid" is a nucleic acid which is not naturally occurring, or which is made by the artificial combination of two otherwise separated segments of sequence. This artificial combination is often accomplished by either chemical, synthesis means, or by the artificial manipulation of isolated segments of nucleic acids, e.g., by genetic engineering techniques. This phrase is also meant to encompass a gene which is removed from its normal regulatory expression constraints, as in the case where a gene product is overexpressed due to the presence of multiple copies of the gene or up regulated promoter or enhancer signals, increased mRNA or protein half life and the like.

Large amounts of the polynucleotides of the present invention may be produced by a suitable host cell transformed with a nucleotide sequence encoding mutant or wildtype proteins described herein. Natural or synthetic polynucleotide fragments coding for the peptide or a desired fragment can be incorporated into recombinant polynucleotide constructs (vectors), usually DNA constructs, capable of introduction into and replication in a prokaryotic or eukaryotic cell. Usually the vectors will be suitable for replication in a unicellular host, such as yeast or bacteria, but may also be intended for introduction to (with and without integration within the genome) cultured mammalian or plant or other eukaryotic cell lines. The most commonly used prokaryotic hosts are strains of *Escherichia coli*, although other prokaryotes, such as *Bacillus subtilis* or *Pseudomonas* may also be used. Mammalian or other eukaryotic host cells, such as those of yeast, filamentous fungi, plant, insect, or amphibian or avian species, may also be useful for production of the proteins of the present invention. As is well known in the relevant art, regulating polynucleotide expression can result in regulation of polypeptides encoded by the polynucleotide.

Vectors, such as cloning and expression vectors, will include an appropriate promoter and other necessary vector sequences that are functional in the selected host, such as those described herein. There may include, when appropriate, those naturally associated with the nucleic acids described herein and protein expression and may include alternative or additional regulatory sequences operably linked to the nucleic acid in order to control expression of the nucleic acid, as well known in the art. Many useful vectors are known in the art and may be obtained from vendors. "Operably linked" refers to a juxtaposition wherein the components so described are in a relationship permitting them to function in their intended manner. For instance, a promoter is operably linked to a coding sequence if the promoter affects its transcription or expression. The vectors may also include a selectable marker gene such as described herein.

In a first aspect, the present invention provides an isolated nucleic acid encoding (i) the Xa10 polypeptide having the amino acid sequence set forth in SEQ ID NO:37 or (ii) a polypeptide having at least 50% identity to the Xa10 polypeptide in which the polypeptide of (ii) provides a plant with resistance to *Xanthomonas* when transfected into the plant. As described herein, the Xa10 polypeptide provides a plant expressing this protein with resistance to *Xanthomonas*. In one embodiment, the polypeptide of (ii) has at least 60% identity. In another embodiment, the polypeptide of (ii) has at least 70% identity. In an additional embodiment, the polypeptide of (ii) has at least 80% identity. In a further embodiment, the polypeptide of (ii) has at least 90% identity. In another embodiment, the polypeptide of (ii) has at least 95% identity. In an additional embodiment, the polypeptide of (ii) has at least 98% identity. In a further embodiment, the polypeptide of (ii) has at least 99% identity. In one embodiment, nucleic acid encoding the Xa10 polypeptide has the nucleotide sequence set forth in SEQ ID NO:35. In another embodiment, the nucleic acid encoding the Xa10 polypeptide has the nucleotide sequence set forth in SEQ ID NO:36. In an additional embodiment, the nucleic acid encoding the Xa10 polypeptide has the nucleotide sequence set forth in nucleotides 54-437 of SEQ ID NO:36. In a further embodiment, the nucleic acid encoding the Xa10 polypeptide has the nucleotide sequence set forth in nucleotides 2423-3234 of SEQ ID NO:35.

In another embodiment, the isolated nucleic acid encoding (i) or (ii) may be operatively linked to a nucleic acid encoding a heterologous polypeptide. Heterologous polypeptides can include proteins of R genes or proteins of defense genes from rice or other plants as known to those of ordinary skill in the art. Non-limiting examples can include rice bacterial blight R proteins Xa1, Xa2, Xa5, Xa13, Xa21, Xa26, Xa27 or defense proteins such as, e.g., PR1 from rice.

The present invention also provides Xa10 polypeptide described herein. In addition, the present invention provides a plant cell comprising the isolated nucleic acid and a transgenic plant resistant to *Xanthomonas* comprising the plant cell.

In a second aspect, the present invention provides a vector comprising an isolated nucleic acid encoding (i) the Xa10 polypeptide having the amino acid sequence set forth in SEQ ID NO:37 or (ii) a polypeptide having at least 50% identity to the Xa10 polypeptide in which the polypeptide of (ii) provides a plant with resistance to *Xanthomonas* when transfected into the plant described herein. In one embodiment, the vector further comprises a plant promoter operably linked to the isolated nucleic acid. In another embodiment, the promoter is selected from the group consisting of a tissue-specific promoter, a constitutive promoter and an inducible promoter. In a further embodiment, the promoter is an Xa10 promoter or one derived from the Xa10 promoter or contains a part of the Xa10 promoter, including promoters described herein. In one embodiment, the vectors may also include other regulatory sequences such as described herein. In another embodiment, the isolated nucleic acid encoding (i) or (ii) in the vector may be operatively linked to a nucleic acid encoding a heterologous polypeptide, such as described herein.

A number of promoters can be used in the practice of the invention. The promoters can be selected based on the desired outcome. That is, the nucleic acids can be combined with constitutive, tissue-preferred, or other promoters for expression in the host cell of interest. Such constitutive promoters include, for example, the core promoter of the Rsyn7 (WO 99/48338 and U.S. Pat. No. 6,072,050); the core CaMV35S promoter (Odell et al., 1985); rice actin (McElroy et al., 1990); ubiquitin (Christensen and Quail, 1989 and Christensen et al., 1992); pEMU (Last et al., 1991); MAS (Velten et al., 1984); ALS promoter (U.S. Pat. No. 5,659,026), and the like. Other constitutive promoters include, for example, those disclosed in U.S. Pat. Nos. 5,608,149; 5,608,144; 5,604,121; 5,569,597; 5,466,785; 5,399,680; 5,268,463; and 5,608,142.

Other promoters include inducible promoters, particularly from a pathogen-inducible promoter. Such promoters include those from pathogenesis-related proteins (PR proteins), which are induced following infection by a pathogen; e.g., PR proteins, SAR proteins, beta-1,3-glucanase, chitinase, etc. Other promoters include those that are expressed locally at or near the site of pathogen infection. In further embodiments, the promoter may be a wound-inducible promoter. In other embodiments, chemical-regulated promoters can be used to modulate the expression of a gene in a plant through the application of an exogenous chemical regulator. The promoter may be a chemical-inducible promoter, where application of the chemical induces gene expression, or a chemical-repressible promoter, where application of the chemical represses gene expression. In addition, tissue-preferred promoters can be utilized to target enhanced expression of a polynucleotide of interest within a particular plant tissue. Each of these promoters are described in U.S. Pat. Nos. 6,506,962, 6,575,814, 6,972,349 and 7,301,069 and in U.S. Patent Application Publication Nos. 2007/0061917 and 2007/0143880.

In an additional embodiment, promoter is selected from the group consisting of the Xa10 promoter having the nucleotide sequence set forth in SEQ ID NO:38, the Xa10 promoter having the nucleotide sequence set forth in nucleotides 1 through 2422 of SEQ ID NO:38 and the Xa10 promoter having the nucleotide sequence set forth in SEQ ID NO:39. In a further embodiment, promoter is selected from the group consisting of a promoter containing the AvrXa10 box having the nucleotide sequence set forth in SEQ ID NO:23 and promoters containing derivatives of the AvrXa10 box, wherein the derivatives of the AvrXa10 box are selected from the group consisting of a derivative having the nucleotide sequence set forth in SEQ ID NO:26, a derivative having the nucleotide sequence set forth in SEQ ID NO:28, a derivative having the nucleotide sequence set forth in SEQ ID NO:30, a derivative having the nucleotide sequence set forth in SEQ ID NO:31, a derivative having the nucleotide sequence set forth in SEQ ID NO:68, a derivative having the nucleotide sequence set forth in SEQ ID NO:72, a derivative having the nucleotide sequence set forth in SEQ ID NO:73, a derivative having the nucleotide sequence set forth in SEQ ID NO:74, a derivative having the nucleotide sequence set forth in SEQ ID NO:82, a derivative having the nucleotide sequence set forth in SEQ ID NO:83, a derivative having the nucleotide sequence set forth in SEQ ID NO:84 and a derivative having the nucleotide sequence set forth in SEQ ID NO:85. The present invention also provides a plant cell comprising the vector and a transgenic plant resistant to *Xanthomonas* comprising the plant cell. In a preferred embodiment, the nucleic acid of the present invention is stably integrated in the genome of the transgenic plant cell or transgenic plant.

In a third aspect, the present invention provides methods of (i) making a plant resistant to *Xanthomonas*, (b) enhancing resistance to *Xanthomonas* in a plant and (c) conferring resistance to *Xanthomonas* disease to a plant. Each of these methods comprises transfecting the isolated nucleic acid described herein or the vector described herein into a plant cell or plant cells and growing a plant from the transfected plant cell or transfected plant cells such that the isolated nucleic acid is expressed in the plant. Transfecting the nucleic acid or vector into a plant cell or cells is also sometimes referred to herein as transforming a plant cell or cells with the nucleic acid or vector. In a preferred embodiment, the nucleic acid of the present invention is stably integrated in the genome of the transgenic plant cell or transgenic plant.

In a fourth aspect, the present invention provides an isolated nucleic acid having promoter activity in a plant. In one embodiment, the nucleic acid has the nucleotide sequence set forth in SEQ ID NO:38 or the nucleotide sequence set forth in nucleotides 1 to 2422 of SEQ ID NO:38. In another embodiment, the nucleic acid has the nucleotide sequence set forth in SEQ ID NO:39. In a further embodiment, the nucleic acid comprising a plant operable promoter containing the nucleotide sequence set forth in SEQ ID NO:23. Suitable plant operable promoters for this embodiment and the following embodiments include those described herein and those well known to the skilled artisan. In another embodiment, the nucleic acid comprising a plant operable promoter containing the nucleotide sequence set forth in SEQ ID NO:26. In an additional embodiment, the nucleic acid comprising a plant operable promoter containing the nucleotide sequence set forth in SEQ ID NO:28. In a further embodiment, the nucleic acid comprising a plant operable promoter containing the nucleotide sequence set forth in SEQ ID NO:30. In another embodiment, the nucleic acid comprising a plant operable promoter containing the nucleotide sequence set forth in SEQ ID NO:31. In an additional embodiment, the nucleic acid comprising a plant operable promoter containing the nucleotide sequence set forth in SEQ ID NO:68. In a further embodiment, the nucleic acid comprising a plant operable promoter containing the nucleotide sequence set forth in SEQ ID NO:72. In another embodiment, the nucleic acid comprising a plant operable promoter containing the nucleotide sequence set forth in SEQ ID NO:73. In a further embodiment, the nucleic acid comprising a plant operable promoter containing the nucleotide sequence set forth in SEQ ID NO:74. In another embodiment, the nucleic acid comprising a plant operable promoter containing the nucleotide sequence set forth in SEQ ID NO:82. In an additional embodiment, the nucleic acid comprising a plant operable promoter containing the nucleotide sequence set forth in SEQ ID NO:83. In a further embodiment, the nucleic acid comprising a plant operable promoter containing the nucleotide sequence set forth in SEQ ID NO:84. In another embodiment, the nucleic acid comprising a plant operable promoter containing the nucleotide sequence set forth in SEQ ID NO:85. The present invention also provides a nucleic acid construct comprising the nucleic acid having promoter activity operably linked to a second nucleic acid encoding a nucleic acid of interest. In addition, the present invention provides a transgenic plant cell or a transgenic plant containing the nucleic acid construct in its genome. The present invention further provides a method of producing the transgenic plant cell or transgenic plant. The transgenic plant cell is produced by transfecting the nucleic acid construct into a plant cell or cells. The transgenic plant is produced by regenerating a plant from the transfected plant cell or cells.

The promoters of the present invention are particularly useful for preparing transgenic plants, including those described herein, to contain a nucleic acid or DNA of interest. The nucleic acid or DNA that is inserted (the nucleic acid or DNA of interest) into plants is not critical to the transformation process. Generally the DNA that is introduced into a plant is part of a construct. The DNA may be a gene of interest, e.g., a coding sequence for a protein, or it may be a sequence that is capable of regulating expression of a gene, such as an antisense sequence, a sense suppression sequence, a post-transcriptional gene silencing sequence (an RNAi sequence such as an siRNA, shRNA or dsRNA) or a micro-RNA (miRNA) sequence. The construct typically includes regulatory regions operatively linked to the 5' side of the DNA of interest and/or to the 3' side of the DNA of interest. A cassette containing all of these elements is also referred to herein as an expression cassette. The expression cassettes may additionally contain 5' leader sequences in the expression cassette construct. The regulatory regions (i.e., promoters, transcriptional regulatory regions, and translational termination regions) and/or the polynucleotide encoding a signal anchor may be native/analogous to the host cell or to each other. The promoters identified herein are particularly useful for preparing constructions for the transformation of plant species described herein. Alternatively, the regulatory regions and/or the polynucleotide encoding a signal anchor may be heterologous to the host cell or to each other. See, U.S. Pat. No. 7,205,453 and U.S. Patent Application Publication Nos. 2006/0218670, 2006/0248616 and 20090100536, and the references cited therein. The expression cassettes may additionally contain 5' leader sequences in the expression cassette construct. Such leader sequences can act to enhance translation. Translation leaders are known in the art and include those described in International Publication No. WO 2008/094127 and the references cited therein.

The DNA of interest that is under control of a promoter, such as a promoter described herein, may be any DNA as described herein and may be used to alter any characteristic or trait of a plant species into which it is introduced. In one embodiment, the DNA of interest is introduced into a plant in order to enhance a trait of the plant. In another embodiment, an enhanced agronomic trait may be characterized by enhanced plant morphology, physiology, growth and development, yield, nutritional enhancement, disease or pest resistance, or environmental or chemical tolerance. In some aspects, the enhanced trait is selected from group of enhanced traits consisting of enhanced water use efficiency, enhanced temperature tolerance, increased yield, enhanced nitrogen use efficiency, enhanced seed protein enhanced seed oil and enhanced biomass. Increase yield may include increased yield under non-stress conditions and increased yield under environmental stress conditions. Stress conditions may include, for example, drought, shade, fungal disease, viral disease, bacterial disease, insect infestation, nematode infestation, extreme temperature exposure (cold or hot), osmotic stress, reduced nitrogen nutrient availability, reduced phosphorus nutrient availability and high plant density. In some embodiments, the DNA of interest may be used to modify metabolic pathways, such as fatty acid biosynthesis or lipid biosynthesis pathways in seeds, or to modify resistance to pathogens, especially *Xanthomonas*, in plant species. The promoters of the present invention can be induced or activated by the AvrXa10 protein described herein or a nucleic acid encoding this protein as described herein.

Generally, the expression cassette may additionally comprise a selectable marker gene for the selection of transformed cells. Selectable marker genes are utilized for the selection of transformed cells or tissues. Usually, the plant selectable marker gene will encode antibiotic resistance, with suitable genes including at least one set of genes coding for resistance to the antibiotic spectinomycin, the streptomycin phosphotransferase (spt) gene coding for streptomycin resistance, the neomycin phosphotransferase (nptII) gene encoding kanamycin or geneticin resistance, the hygromycin phosphotransferase (hpt or aphiv) gene encoding resistance to hygromycin, acetolactate synthase (als) genes. Alternatively, the plant selectable marker gene will encode herbicide resistance such as resistance to the sulfonylurea-type herbicides, glufosinate, glyphosate, ammonium, bromoxynil, imidazolinones, and 2,4-dichlorophenoxyacetate (2,4-D), including genes coding for resistance to herbicides which act to inhibit the action of glutamine synthase such as phosphinothricin or basta (e.g., the bar gene). See generally, International Publication No. WO 02/36782, U.S. Pat. No. 7,205,453 and U.S. Patent Application Publication Nos. 2006/0218670, 2006/0248616, 2007/0143880 and 20090100536, and the references cited therein. This list of selectable marker genes is not meant to be limiting. Any selectable marker gene can be used. The selectable marker gene is also under control of a promoter operable in the plant species to be transformed. Such promoters include those described in International Publication No. WO 2008/094127 and the references cited therein.

Where appropriate, the DNA of interest may be optimized for increased expression in the transformed plant. That is, the coding sequences can be synthesized using plant-preferred codons for improved expression. Methods are available in the art for synthesizing plant-preferred genes. See, for example, U.S. Pat. Nos. 5,380,831, 5,436,391, and 7,205,453 and U.S. Patent Application Publication Nos. 2006/0218670 and 2006/0248616.

In preparing the expression cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g. transitions and transversions may be involved.

Once a nucleic acid has been cloned into an expression vector, it may be introduced into a plant cell using conventional transformation procedures. The term "plant cell" is intended to encompass any cell derived from a plant including undifferentiated tissues such as callus and suspension cultures, as well as plant seeds, pollen or plant embryos. Plant tissues suitable for transformation include leaf tissues, root tissues, meristems, protoplasts, hypocotyls, cotyledons, scutellum, shoot apex, root, immature embryo, pollen, and anther. "Transformation" means the directed modification of the genome of a cell by the external application of recombinant DNA from another cell of different genotype, leading to its uptake and integration into the subject cell's genome. In this manner, genetically modified plants, plant cells, plant tissue, seed, and the like can be obtained.

DNA constructs containing the promoters of the present invention can be used to transform any plant, including those described herein. The constructs may be introduced into the genome of the desired plant host by a variety of conventional techniques. Techniques for transforming a wide variety of higher plant species are well known and described in the technical and scientific literature. Transformation protocols may vary depending on the type of plant or plant cell, i.e., monocot or dicot, targeted for transformation, as is well known to the skilled artisan. For example, the DNA construct may be introduced directly into the genomic DNA of the plant cell using techniques such as electroporation and microinjection of plant cell protoplasts, or the DNA constructs can be introduced directly to plant tissue using ballistic methods, such as DNA particle bombardment. Alternatively, the DNA constructs may be combined with suitable T-DNA flanking regions and introduced into a conventional *Agrobacterium tumefaciens* host vector. The virulence functions of the *Agrobacterium tumefaciens* host will direct the insertion of the construct and adjacent marker into the plant cell DNA when the cell is infected by the bacteria. Thus, any method, which provides for effective transformation/transfection may be employed. See, for example, U.S. Pat. Nos. 7,241,937, 7,273,966 and 7,291,765 and U.S. Patent Application Publication Nos. 2007/0231905 and 2008/0010704 and references cited therein. See also, International Published Application Nos. WO 2005/103271 and WO 2008/094127 and references cited therein.

In one embodiment, the explant tissue can be co-cultured with an *Agrobacterium* strain harboring a DNA construct containing a gene or nucleic acid of interest using techniques well known in the art. Transformed tissue can be selected using conventional techniques well known in the art. In another embodiment, the embryogenic liquid suspension cultures can be co-cultured with an *Agrobacterium* strain harboring a DNA construct containing a gene or nucleic acid of interest using techniques well known in the art. Transformed tissue can be selected using conventional techniques well known in the art. In a further embodiment, the DNA can be introduced into the explant tissue or cells of the embryogenic liquid suspension culture using conventional techniques, such as particle bombardment. Transformed tissue can be selected using conventional techniques well known in the art. Transformed or transgenic plants can be regenerated using the methods well known in the art Transformed plant cells which are derived by any of the above transformation techniques can be cultured to regenerate a whole plant which possesses the transformed genotype and thus the desired phenotype, e.g., a transgenic plant. A "transgenic plant" is a plant into which foreign DNA has been introduced. A "transgenic plant" encompasses all descendants, hybrids, and crosses thereof, whether reproduced sexually or asexually, and which continue to harbor the foreign DNA. Regeneration techniques rely on manipulation of certain phytohormones in a tissue culture growth medium, typically relying on a biocide and/or herbicide marker which has been introduced together with the desired nucleotide sequences. See for example, International Published Application No. WO 2008/094127 and references cited therein.

The foregoing methods for transformation are typically used for producing a transgenic variety in which the expression cassette is stably incorporated. After the expression cassette is stably incorporated in transgenic plants, it can be transferred to other plants by sexual crossing. In one embodiment, the transgenic variety could then be crossed, with another (non-transformed or transformed) variety, in order to produce a new transgenic variety. Alternatively, a genetic trait which has been engineered into a particular cotton line using the foregoing transformation techniques could be moved into another line using traditional backcrossing techniques that are well known in the plant breeding arts. For example, a backcrossing approach could be used to move an engineered trait from a public, non-elite variety into an elite variety, or from a variety containing a foreign gene in its genome into a variety or varieties which do not contain that gene. As used herein, "crossing" can refer to a simple X by Y cross, or the process of backcrossing, depending on the context. Any of a number of standard breeding techniques can be used, depending upon the species to be crossed.

Once transgenic plants of this type are produced, the plants themselves can be cultivated in accordance with conventional procedures. Transgenic seeds can, of course, be recovered from the transgenic plants. These seeds can then be planted in the soil and cultivated using conventional procedures to produce transgenic plants.

In a fifth aspect, the present invention provides uses and methods to control gene expression in transgenic plants. In one embodiment, the isolated nucleic acid having promoter activity described herein is used to control gene expression in a transgenic plant. In another embodiment, a nucleic acid encoding the AvrXa10 polypeptide having the amino acid sequence set forth in SEQ ID NO:54 is used to control gene expression in a transgenic plant containing the isolated nucleic acid having promoter activity described herein. In a further embodiment, the AvrXa10 polypeptide having the amino acid sequence set forth in SEQ ID NO:54 is used to control gene expression in a transgenic plant containing the isolated nucleic acid having promoter activity described herein. In one embodiment, the nucleic acid encoding the AvrXa10 polypeptide has the nucleotide sequence set forth in SEQ ID NO:57. In another embodiment, the nucleic acid encoding the AvrXa10 polypeptide has the nucleotide sequence set forth in GenBank Accession No. U50552. The present invention further provides a method of producing transgenic plant cell or transgenic plant having a promoter of the present invention and having a nucleic acid encoding the AvrXa10 polypeptide. The transgenic plant cell is produced by transfecting a nucleic acid construct containing the promoter into a plant cell or cells. In one embodiment a nucleic acid encoding the AvrXa10 polypeptide operably linked to a promoter, such as described herein, is also transfected into the plant cell or cells. The transgenic plant is produced by regenerating a plant from the transfected plant cell or cells. In a second embodiment, first transgenic plants are produced containing a nucleic acid construct containing the promoter into a plant cell or cells and second transgenic plants are produced containing a nucleic acid encoding the AvrXa10 polypeptide operably linked to a promoter. The first and second transgenic plants are then crossed to produce transgenic plants containing both the nucleic acid construct containing the promoter and the nucleic acid encoding the AvrXa10 polypeptide operably linked to a promoter.

The practice of the present invention employs, unless otherwise indicated, conventional techniques of chemistry, molecular biology, microbiology, recombinant DNA, genetics, immunology, cell biology, cell culture and transgenic biology, which are within the skill of the art. See, e.g., Maniatis et al., 1982, *Molecular Cloning* (Cold Spring Harbor Laboratory Press, Cold Spring Harbor, N.Y.); Sambrook et al., 1989, *Molecular Cloning*, 2nd Ed. (Cold Spring Harbor Laboratory Press, Cold Spring Harbor, N.Y.); Sambrook and Russell, 2001, *Molecular Cloning*, 3rd Ed. (Cold Spring Harbor Laboratory Press, Cold Spring Harbor, N.Y.); Ausubel et al., 1992), *Current Protocols in Molecular Biology* (John Wiley & Sons, including periodic updates); Glover, 1985, *DNA Cloning* (IRL Press, Oxford); Russell, 1984, *Molecular biology of plants: a laboratory course manual* (Cold Spring Harbor Laboratory Press, Cold Spring Harbor, N.Y.); Anand, *Techniques for the Analysis of Complex Genomes*, (Academic Press, New York, 1992); Guthrie and Fink, *Guide to Yeast Genetics and Molecular Biology* (Academic Press, New York, 1991); Harlow and Lane, 1988, *Antibodies*, (Cold Spring Harbor Laboratory Press, Cold Spring Harbor, N.Y.); *Nucleic Acid Hybridization* (B. D. Hames & S. J. Higgins eds. 1984); *Transcription And Translation* (B. D. Hames & S. J. Higgins eds. 1984); *Culture Of Animal Cells* (R. I. Freshney, Alan R. Liss, Inc., 1987); *Immobilized Cells And Enzymes* (IRL Press, 1986); B. Perbal, *A Practical Guide To Molecular Cloning* (1984); the treatise, *Methods In Enzymology* (Academic Press, Inc., N.Y.); *Methods In Enzymology*, Vols. 154 and 155 (Wu et al. eds.), *Immunochemical Methods In Cell And Molecular Biology* (Mayer and Walker, eds., Academic Press, London, 1987); *Handbook Of Experimental Immunology*, Volumes I-IV (D. M. Weir and C. C. Blackwell, eds., 1986); Riott, *Essential Immunology*, 6th Edition, Blackwell Scientific Publications, Oxford, 1988; Fire et al., *RNA Interference Technology: From Basic Science to Drug Development*, Cambridge University Press, Cambridge, 2005; Schepers, *RNA Interference in Practice*, Wiley-VCH, 2005; Engelke, *RNA Interference (RNAi): The Nuts & Bolts of siRNA Technology*, DNA Press, 2003; Gott, *RNA Interference, Editing, and Modification: Methods and Protocols (Methods in Molecular Biology)*, Human Press, Totowa, N.J., 2004; Sohail, *Gene Silencing by RNA Interference: Technology and Application*, CRC, 2004.

EXAMPLES

The present invention is described by reference to the following Examples, which is offered by way of illustration and is not intended to limit the invention in any manner. Standard techniques well known in the art or the techniques specifically described below were utilized.

Example 1

Materials and Methods

Rice lines and growth conditions: IRBB10 harbors bacterial blight resistance gene Xa10 in IR24 genetic background (Ogawa et al., 1988). IRBB10A is an improved near-isogenic line of Xa10 in IR24 genetic background (Gu et al., 2008). Nipponbare is a japonica rice variety, which is susceptible to most of the Xoo strains. IRBB5 harbors recessive bacterial blight resistance gene xa5 in the IR24 background (Ogawa et al., 1988). Rice plants were grown in greenhouse at a temperature of 32° for 12.5 h (light) and 25° for 11.5 h (dark).

Bacterial blight inoculation: *Xanthomonas oryzae* pv *oryzae* strains were cultivated at 28° C. on peptone sucrose agar (PSA) plates supplemented with appropriate antibiotics. Bacterial blight inoculation was carried out according to leaf-clipping method (Kauffman et al., 1973; Gu et al., 2008). Disease scoring was measured as described previously (Gu et al., 2004; 2008).

Rice transformation: Subclones of the Xa10 gene were cloned into binary vector pC1300 (CAMBIA, Can berra, Australia) and the binary constructs were transferred into *Agrobacterium tumefaciens* AGL1. *Agrobacterium*-mediated transformation of Nipponbare was carried out according to the method described as Yin et al. (2000).

BAC library construction: Bacterial Artificial Chromosome (BAC) library of Xa10 was constructed according to the protocols described in details by D. G. Peterson et al. (http colon//www dot ncgr dot org/research/jag/paper300/indexpage300 dot html). Briefly, IRBB10 plants were grown in greenhouse for 7-10 days. High-molecular weight (HMW) nuclear DNA was isolated and embedded into low melting agarose plug for partial digestion by HindIII. Partially digested HMW DNA was then size-fractionated using a Pulse-Field Gel Electrophoresis (PFGE) device (CHEF Mapper II, Bio-Rad). Size-fractionated DNA (100-300 kb) was recovered by electroelution (Strong et al., 1997) from low-melting-point agarose gel and ligated to. HindII digested and dephosphorylated BAC vector pIndigoBAC-5 (EPICENTRE, Madison, Wis. 53713, USA). The ligation mix was electroporated into *E. coli* DH10B cells using the Cell-Porator system (GIBCO-BRL). BAC clones were picked up manually and arrayed in 384-well plates with 60 μl freezing media in each well. BAC clones were cultured at 37° C. for 14-16 hours and stored at −80° C. The BAC library consisted of about 50,000 clones with inserts ranging in size from 30-60 kb with the average size at 40 kb. The coverage of this library is at least 3 times equivalent to the rice genome.

Southern blot analysis: Southern blot analysis was carried out according to standard procedures (Sambrook et al. 1989). Approximately 2-5 μg of rice genomic DNA was digested with appropriate restriction enzymes and separated in 0.8% Agarose gel. Southern blots were hybridized with DNA probes labeled with $^{32}P$-dCTP (GE Healthcare, Little Chalfont, Buckinghamshire, UK).

Northern blot analysis: Northern blot analysis was carried out according to standard procedures (Sambrook et al. 1989). Total RNA was isolated from leaves using the RNeasy Plant Mini Kit (Qiagen, Hilden, Germany). About 5 μg messenger RNA (mRNA) used for each lane in northern blot analysis. RNA loading was assessed by hybridizing RNA blots to rice ubiquitin gene 1 (Ubi) probe. DNA probes for northern blot analysis were labeled with $^{32}$P-dCTP (GE Healthcare, Little Chalfont, Buckinghamshire, UK).

Real-time PCR analysis: Approximately 1 μg of DNase I-treated total RNA was converted into single-stranded cDNA using an iScript cDNA Synthesis Kit (Bio-Rad, USA). The quantitative reaction was performed on an IQ5 Multicolor Real-Time PCR Detection System (Bio-Rad, USA) using the SsoFast EvaGreen supermix (Bio-Rad, USA). The reaction mixture (15 μL) contained 2× SsoFast EvaGreen supermix, 0.9 μM each of the forward and reverse primers, and 1 μL of template cDNA. PCR amplification was performed under the following conditions: 95° C. for 30 sec, followed by 40 cycles of 95° C. for 5 sec, 60° C. for 10 sec. A melting-curve protocol immediately followed the amplification with heating for 10 sec, starting at 65° C. with 0.5° C. increments. Rice Ubiquitin 1 gene was used as an internal control. All primers used in this study are listed in Table 1.

TABLE 1

DNA Oligos

| Name | DNA sequence (5'-3') (SEQ ID NO:) | Purpose |
|---|---|---|
| 5'-CDS | TTTTTTTTTTTTTTTTTTTTTTTT(G/A/C)(A/C/T/G) (1) | 5'RACE |
| Xa10RT-F2 | TAAGAAGGAGTAGCCAAGCTCA (2) | 5'RACE |
| RGP6-F | CCTCGTCGTCTTCACCAATGCA (3) | 5'RACE |
| Xa10RT-F3 | CCGGTTTCTCTTTATTAACCGT (4) | 5'RACE |
| NUP | AAGCAGTGGTATCAACGCAGAGTTTTTT(G/A/C) (5) | 5'RACE |
| Oligo-dT-anchor | GACCACGCGTATCGATGTCGACTTTTTTTTTTT (7) | 3'RACE |
| GS4R1 | GACGTGCTCATCATCTACCTC (8) | 3'RACE |
| ANCHOR | GACCACGCGTATCGATGTCGAC (9) | 3'RACE |
| SP1 F | TGCCGTCCTCCTACTGATG (10) | Xa10 DNA probe |
| SP1 R | CCTCGTCGTCTTCACCAATG (11) | Xa10 DNA probe |
| RBQ3 | CCAGTAAGTCCTCAGCCATG (12) | Real-time PCR for Ubi 1 |
| RBQ4 | TTTCAGACACCATCAAACCAG (13) | Real-time PCR for Ubi 1 |
| 10RT F2 | GGCATCATCTTCTCCGGCG (14) | Real-time PCR for Xa10 |
| 10RT R2 | GCAGCTATACGGGCATAAG (15) | Real-time PCR for Xa10 |
| Box 1 | TACATCAATTACTTATT (16) | AvrXa10 box candidate |
| Box 2 | TACACACGTTCACTCCT (17) | AvrXa10 box candidate |
| Box 3 | TACAGCCAGAAAGCACT (18) | AvrXa10 box candidate |
| Box 4 | TATACATCAATTACTTA (19) | AvrXa10 box candidate |
| Box 5 | TATACACGTTCACTC (20) | AvrXa10 box candidate |
| Box 6 | TATACAGCCAGAAAGCA (21) | AvrXa10 box candidate |
| Box 7 | TATATACATCAATTACT (22) | AvrXa10 box candidate |
| Box 8 | TATATACACGTTCAC (23) | AvrXa10 box |
| Box 9 | TATATACAGCCAGAAAG (24) | AvrXa10 box candidate |
| Box 10 | TATATATACATCAATTA (25) | AvrXa10 box candidate |
| Box 11 | TATATATACACGTTC (26) | AvrXa10 box candidate |
| Box 12 | TATATATACAGCCAGAA (27) | AvrXa10 box candidate |
| 8D15 | TATATACACGTTC (28) | AvrXa10 box 3'deletion |
| 1D8 | ATATACACACGTTC (29) | AvrXa10 box 5' and 3'deletion |
| 8D14 | TATATACACACGTT (30) | AvrXa10 box 3'deletion |
| 8D13 | TATATACACACGT (31) | AvrXa10 box 3'deletion |
| 8D12 | TATATACACACG (32) | AvrXa10 box 3'deletion |
| 8D11 | TATATACACAC (33) | AvrXa10 box 3'deletion |

TABLE 1-continued

DNA Oligos

| Name | DNA sequence (5'-3') (SEQ ID NO:) | Purpose |
|---|---|---|
| AvrXa27 box | TAGAAGAAGAGACCAATA (44) | UPT$_{AvrXa27}$ box (Romer et al., 2009b) |
| AvrXa10 box probe | ACTCCTCTTATATATACACACGTTCACTCCTCT (34) | EMSA |
| AvrXa27 box probe | GTGCTATAAATAGAAGAAGAGACCAATAGAGAGC (45) | EMSA |
| Box 8 0dT probe | ACTCCTCTTAATATATACACACGTTCACTCCTCT (46) | EMSA |
| Box 8 1dA probe | ACTCCTCTTATTATACACACGTTCACTCCTCT (47) | EMSA |
| Box 8 2dT probe | ACTCCTCTTATAATACACACGTTCACTCCTCT (48) | EMSA |
| Box 8 3dA probe | ACTCCTCTTATATTACACACGTTCACTCCTCT (49) | EMSA |
| Box 8 4dT probe | ACTCCTCTTATATAACACACGTTCACTCCTCT (50) | EMSA |
| Box 8 5dA probe | ACTCCTCTTATATATCACACGTTCACTCCTCT (51) | EMSA |
| Box 8 6dC probe | ACTCCTCTTATATATAACACGTTCACTCCTCT (52) | EMSA |
| Box 8 7dA probe | ACTCCTCTTATATATACCACGTTCACTCCTCT (53) | EMSA |
| Box 8 8dC probe | ACTCCTCTTATATATACAACGTTCACTCCTCT (58) | EMSA |
| Box 8 9dA probe | ACTCCTCTTATATATACACCGTTCACTCCTCT (59) | EMSA |
| Box 8 10dC probe | ACTCCTCTTATATATACACAGTTCACTCCTCT (60) | EMSA |
| Box 8 11dG probe | ACTCCTCTTATATATACACACTTCACTCCTCT (61) | EMSA |
| Box 8 12dT probe | ACTCCTCTTATATATACACACGTCACTCCTCT (62) | EMSA |
| Box 8 13dT probe | ACTCCTCTTATATATACACACGTCACTCCTCT (63) | EMSA |
| Box 8 14dC probe | ACTCCTCTTATATATACACACGTTACTCCTCT (64) | EMSA |
| Box 8 15dA probe | ACTCCTCTTATATATACACACGTTCCTCCTCT (65) | EMSA |
| Box 8 16dC probe | ACTCCTCTTATATATACACACGTTCATCCTCT (66) | EMSA |
| Box 8M1 | TATATACATCAGTTCAC (67) | AvrXa10 box mutant |
| Box 7M | TATATACACACATTACT (68) | AvrXa10 box mutant |
| Box 7M1 | TATATACACCAATTACT (69) | Box 7 mutant |
| Box 7M2 | TATATACATAAATTACT (70) | Box 7 mutant |
| Box 7M3 | TATATACATCCATTACT (71) | Box 7 mutant |
| Box 7M4 | TATATACACAAATTACT (72) | Box 7 mutant |
| Box 7M5 | TATATACACCCATTACT (73) | Box 7 mutant |
| Box 7M6 | TATATACATACATTACT (74) | Box 7 mutant |
| Box 8M1 probe | ACTCCTCTTATATATACATCAGTTCACTCCTCT (75) | EMSA |
| Box 7 probe | TTCTCTTATATATACATCAATTACTTATTGATG (76) | EMSA |
| Box 7M probe | TTCTCTTATATATACACATTACTTATTGATG (77) | EMSA |
| pAbAi F2 | CCAAGAAGATGTAATGCACCC (6) | Yeast colony PCR |
| pAbAi R2 | CATTACGACCGAGATTCCCG (78) | Yeast colony PCR |
| Box 8 13dT | TATATACACACGTCAC (82) | Box 8 deletion |
| Box 8 14dC | TATATACACACGTTAC (83) | Box 8 deletion |
| Box 8 15dA | TATATACACACGTTCC (84) | Box 8 deletion |

TABLE 1-continued

DNA Oligos

| Name | DNA sequence (5'-3') (SEQ ID NO:) | Purpose |
|---|---|---|
| Box 8 16dC | TATATACACACGTTCA (85) | Box 8 deletion |
| Box 8 0dT | ATATACACACGTTCAC (40) | Box 8 deletion |
| Box 8 1dA | TTATACACACGTTCAC (86) | Box 8 deletion |
| Box 8 2dT | TAATACACACGTTCAC (87) | Box 8 deletion |
| Box 8 3dA | TATTACACACGTTCAC (88) | Box 8 deletion |
| Box 8 4dT | TATAACACACGTTCAC (89) | Box 8 deletion |
| Box 8 5dA | TATATCACACGTTCAC (90) | Box 8 deletion |
| Box 8 6dC | TATATAACACGTTCAC (91) | Box 8 deletion |
| Box 8 7dA | TATATACCACGTTCAC (92) | Box 8 deletion |
| Box 8 8dC | TATATACAACGTTCAC (93) | Box 8 deletion |
| Box 8 9dA | TATATACACCGTTCAC (94) | Box 8 deletion |
| Box 8 10dC | TATATACACAGTTCAC (95) | Box 8 deletion |
| Box 8 11dG | TATATACACACTTCAC (96) | Box 8 deletion |
| Box 8 12dT | TATATACACACGTCAC (97) | Box 8 deletion |

Rapid amplification of cDNA ends (RACE): Xa10 cDNA was isolated using a SMART RACE™ cDNA Amplification Kit (Clontech). Both 5' RACE and 3' RACE were conducted according to the manufacturer's instructions. The PCR products were cloned into pGEM T-easy vector (Promega) and sequenced. The primers used for first-strand cDNA synthesis for 5' and 3' RACE were 5'-CDS and Oligo-dT-anchor, respectively (Table 1). The specific primers for 5' RACE were Xa10RT-F2, RGP6-F and Xa10RT-F3 (Table 1). The anchor primer for 5' RACE was NUP (Table 1). The specific primers for 3' RACE was GS4R1 (Table 1). The anchor primer for 3' RACE was ANCHOR (Table 1).

GUS reporter constructs: GUS reporter constructs were based on pCAMBIA vector pC1305.1 (Wu et al., 2008) and pANDA vector pANDA35HK (Miki and Shimamoto, 2004) and minimal Bs4 promoter (Boch et al., 2009). Briefly, the 35S promoter in pC1305.1 was removed by digested with HindIII and NcoI and the vector fragment was filled in and self-ligated to produce pC1305.1 (−35S). The 2151-bp XhoI-XbaI fragment in pC1305.1 (−35S), which consists of the coding sequence of hygromycin resistance gene and another 35S promoter, was replaced with 1787-bp XhoI-SpeI fragment of attR element from pANDA35HK to generate pCGWGUSint. The minimal Bs4 promoter was amplified by PCR and inserted into pENTR/DTOPO (Invitrogen, Carlsbad, Calif., USA) with target DNA boxes at the 5' end (Boch et al., 2009). Promoter derivatives were cloned into pCGWGUSint containing a promoterless GUSPlus gene from pC1305.1.

Agrobacterium infiltration and qualitative β-glucuronidase (GUS) assay: Agrobacterium tumefaciens C58C1 (GV3101) strains harboring TAL effector constructs or GUS reporter constructs were grown at 28° C. in LB supplemented with appropriate antibiotics and 10 mM 2-(N-morpholino) ethanesulfonic acid (MES). The two strains were collected, resuspended and mixed 1:1 in infiltration medium (10 mM $MgCl_2$, 5 mM MES, 150 μM acetosyringone, pH 5.3). Bacterial solutions with an OD600 of 0.8 were inoculated into the abaxial surface of Nicotiana benthamiana leaves using a 1 ml needleless syringe as described previously (Kay et al., 2007). Inoculated plants were grown in a growth room at 25° C. with 16 h light. For qualitative GUS assays, leaf discs were sampled two days post infiltration (dpi), incubated in 5-bromo-4-chloro-3-indolyl-β-D-glucuronide (X-Gluc) staining solution, destained in ethanol, and dried. For quantitative assay, two leaf discs (1-cm diameter) from two different plants at 2 dpi were combined and ground in liquid nitrogen. Proteins were extracted with 300 ul GUS extraction buffer (50 mM sodium phosphate (pH7.0), 10 mM EDTA, 10 mM Beta-mercaptoethanol, 0.1% Triton-X100, 0.1% SDS). Supernatant was collected by centrifugation at 4° C. For the fluorometric assay, 10 μl sample was mixed with 90 μl assay buffer (GUS extraction buffer supplied with 10 mM 4-methyl-umbelliferyl-β-D-glucuronide (MUG)). The reaction samples were incubated at 37° C. for 5 min. The reaction was stopped by mixing 10 μl of reaction sample with 90 μl 0.2 M sodium carbonate ($Na_2CO_3$, pH 9.5). Measurements were done in a plate reader at 360 nm (excitation) and 465 nm (emission) with 4-methyl-umbelliferon (MU) dilutions as standard. The protein amounts were quantified by Bradford assay (BioRad, Hercules, Calif., U.S.A.). Experiments were performed at least twice.

Yeast one-hybrid studies: For protein-DNA interaction studies, the Matchmaker Gold Yeast One-Hybrid Library Screening System (Takara Bio Asia Pacific/Clontech) was used and the experiments were carried out according to the manufacturer's protocol. One to four copies of bait DNA sequence were cloned into pAbAi vector in tandem to yield bait constructs. The AvrXa10 gene was cloned into pGADT7-Rec to create prey constructs, in which AvrXa10 is fused to SV40 NLS-GAL4 AD as prey. The GAL4-AD fusion of murine p53 protein and a bait containing its target sequence (p53DBS) served as controls. The bait constructs were digested with BstBI and transformed into yeast strain Y1HGold. The transformants were verified by using a colony PCR. The prey constructs were then transformed into the generated Y1HGold strains that harbored the cognate bait DNA sequences in their genomes. Transformants grown on selective SD medium at 30° C. were resuspended in 0.9% NaCl with an OD600 of 0.002 or approximately 2000 cells per 100 µl. Serial dilutions in 0.9% NaCl were dropped on SD medium supplemented with Leucine or 200 ng/ml Aureobasidin A (AbA). Identical transformants were inspected for presence of the bait plasmid by colony PCR and for expression of GAL4-AD-fusion proteins by immunoblot.

Yeast colony PCR: Single yeast colonies were resuspended in 20 lyticase buffer (1.2 M sorbitol, 0.1 M sodium phosphate pH7.4, 2.5 mg/ml lyticase (Sigma-Aldrich, INC., Saint Louis USA)), incubated 30 min at 37° C. and 10 min at 95° C. 5 µl of a 1:5 dilution were used for PCR with oligonucleotides pAbA1-F2 and pAbA1-R2 (Table 1).

Western blot analysis was carried out according to the method described by Kay et al., (2009). Single yeast colonies were resuspended in histidine-containing SD liquid medium to an $OD_{600}$=0.15 and grown at 30° C. and 150 rpm to $OD_{600}$=0.4 to 0.6. Cells of 3 ml culture were resuspended in 30 µl cracking buffer (8 M urea, 5% (w/v) SDS, 40 mM Tris-HCl pH 6.8, 0.1 mM EDTA, 0.4 mg/ml bromophenol blue, 0.1% β-ME). Samples were incubated together with glass beads (425-600 µm; Sigma #G-8772) at 20° C. and 14000 rpm for 30 s, and set on ice for 30 s. This step was repeated three times. Samples were centrifuged at 14000 rpm and 4° C. for 10 min. The supernatant was denatured at 70° C. for 5 min. 25 µl protein extract was separated on 8% SDS polyacrylamide gels and subjected to immunoblot analysis with Anti-GAL4 AD (Sigma-Aldrich) and Anti-rabbit IgG (Sigma-Aldrich) antibodies. Reactions were visualized by enhanced chemiluminescence as recommended (Amersham).

Electromobility shift assay (EMSA): EMSA was carried out according to the method described by Kay et al (2007) with slight modification. Polyhistidine-tagged (6xHis) fusion proteins were purified from E. coli M15 as using a QIAexpressionist™ kit (Qiagen, Chats-worth, CA). Protein concentration was determined by Bradford assay (BioRad). Complementary pairs of nonlabeled or 3'-biotin-labeled oligonucleotides ($1^{st}$ BASE, Singapore) were annealed to obtain double-stranded DNA. EMSA was performed with the Light Shift® Chemiluminescent EMSA Kit (Pierce, Rockford, Ill., USA) according to the manufacturer's protocol. The binding reactions contained 12 mM Tris-HCl (pH 7.5), 60 mM KCl, 1 mM DTT, 2.5% Glycerol, 5 mM $MgCl_2$, 50 ng/µl poly(dI•dC), 0.05% NP-40, 0.2 mM EDTA, 20 fmol biotin-labeled DNA, 0-10 pmol unlabeled DNA, 60-6000 fmol 6xHis fusion protein. The binding reactions were kept on ice for 10 min before biotin-labeled DNA was added. The binding reactions were incubated at room temperature for 20 minutes. Gel electrophoresis was performed on a 6% native polyacrylamide gel. After blotting on a positively charged nylon membrane (Amersham) the DNA was Cross-linked at 120 mJ/$cm^2$ by UV-light cross-linker instrument equipped with 254 nm bulbs.

Example 2

Xa10 Ecodes a Novel Transmembrane Protein

Figure 2:
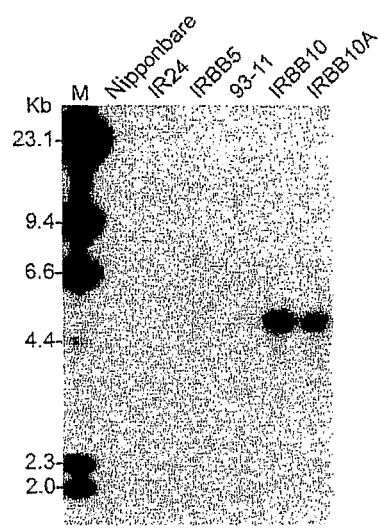
Figure 3:
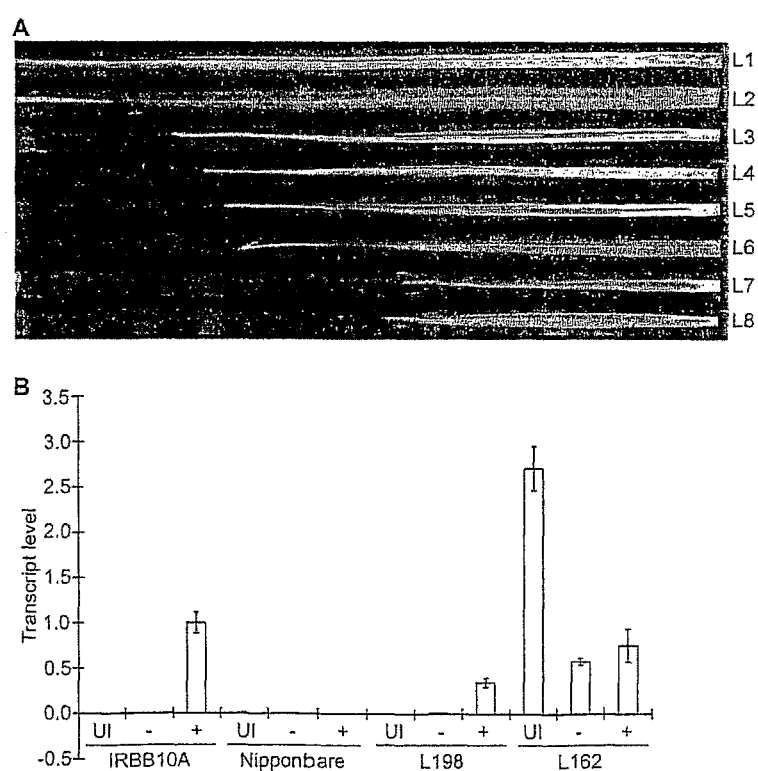

The Xa10 gene was isolated from Xa10 line IRBB10A by map-based cloning and genetic transformation. Xa10 flanking markers M491 and M419 (Gu et al. 2008), and Xa10 co-segregating marker S723 were used to screen a home-made Xa10 BAC library. BAC clone 44M10 was picked up by both M491 and S723 (FIG. 1A). The BAC insert in 44M10 was sequenced and its subclones were used for transformation of susceptible variety Nipponbare. Six of the nine 44M10 subclones produced independent transgenic plants that were resistant to Xa10-incompatible Xoo strain PXO99(pHM1AvrXa10) (Table 2; FIG. 1A). These resistant transgenic lines conferred race-specific resistance to Xa10-incompatible Xoo strains but not to Xa10-compatible strains (Tables 3 and 4, FIGS. 1A and 1B). A. 521-bp Xa10 cDNA clone (SEQ ID NO:36) was isolated by reverse transcription polymerase chain reaction (RT-PCR) and rapid amplification of 5' complementary DNA ends (5' RACE). Comparison of the Xa10 cDNA with its genomic sequence (SEQ ID NO:35) identified an intron of 249 bp at its 3' untranslated region (3'UTR) (FIG. 1C). The donor and acceptor at the splice sites of the intron are GA and CG, which does not follow the general GT-AG rule for intron splicing in higher plants (FIG. 1C). This comparison also identified the promoter region (SEQ ID NO:38) of the Xa10 gene. Southern blot analysis using a probe from Xa10 coding region indicated that the Xa10 gene is only present in Xa10 plants but not in susceptible rice lines (FIG. 2). The ectopic expression of the Xa10 coding sequence under the control of the rice PR1 promoter, which is not activated specifically by AvrXa10, provided non-specific resistance to both Xa10-compatible and Xa10-incompatible Xoo strains (Table 4; FIG. 3A). These results indicated that it is the Xa10 gene product that provides resistance to Xoo.

TABLE 2

Summary of Disease Evaluation of Xa10
Transgenic Lines to Xoo Strain PXO99(pHM1avrXa10)

| Subclone[1] | Total lines | Resistant lines |
|---|---|---|
| S18901 | 109 | 38 |
| A14799 | 88 | 50 |
| ES11947 | 35 | 22 |
| EA9295 | 65 | 45 |
| SA4686 | 106 | 7 |
| PX3834 | 35 | 3 |
| SX10761 | 70 | 0 |
| EN6879 | 95 | 0 |
| B6804 | 98 | 0 |

[1]Subclones at the Xa10 locus used for Agrobacterium-mediated rice transformation. S18901, 18901-bp SpeI fragment; A14799, 14799-bp AvrII fragment; ES11947, 11947-bp EcoRI-SpeI fragment; EA9295, 9295-bp EcoRV- AvrII fragment; SA4686, 4686-bp SacI-AvrII fragment; PX3834, 3834-bp PmlI-XbaI fragment; SX10761, 10761-bp SpeI-XhoI fragment; EN6879, 6879-bp EcoRV-NruI fragment; B6804, 6804-bp BamHI fragment.

TABLE 3

Disease Evaluation of Xa10 Transgenic Lines to Bacterial Blight[1]

| Line | Xa10 subclone | Copy number[2] | Lesion length (cm) and disease score[3] | |
|---|---|---|---|---|
| | | | PXO99 (pHM1AvrXa10) | PXO99 |
| IR24 | wild-type | N.A. | 17.3 ± 4.4 (S) | 22.0 ± 3.9 (S) |
| IRBB10A | wild-type | N.A. | 0.1 ± 0.1 (R) | 26.0 ± 3.6 (S) |
| Nipponbare | wild-type | N.A | 10.7 ± 4.8 (S) | 10.9 ± 3.1 (S) |
| L673 | A14799 | 1 | 0.1 ± 0.0 (R) | 6.1 ± 2.4 (MS) |
| L58 | ES11947 | 1 | 0.5 ± 0.5 (R) | 11.1 ± 2.9 (S) |
| L74 | EA9295 | 1 | 0.1 ± 0.0 (R) | 6.6 ± 2.7 (MS) |
| L142 | SA4686 | 2 | 0.1 ± 0.0 (R) | 6.3 ± 2.5 (MS) |
| L186 | SA4686 | 1 | 0.1 ± 0.1 (R) | N.D. |
| L198 | SA4686 | 1 | 0.1 ± 0.0 (R) | 7.8 ± 2.9 (MS) |
| L211 | SA4686 | 1 | 0.1 ± 0.1 (R) | 7.2 ± 3.5 (MS) |
| L289 | SA4686 | N.D. | 0.1 ± 0.1 (R) | N.D. |

TABLE 3-continued

Disease Evaluation of Xa10 Transgenic Lines to Bacterial Blight[1]

| Line | Xa10 subclone | Copy number[2] | Lesion length (cm) and disease score[3] | |
|---|---|---|---|---|
| | | | PXO99 (pHM1AvrXa10) | PXO99 |
| L306 | SA4686 | 2 | 0.1 ± 0.1 (R) | N.D. |
| L635 | SA4686 | 1 | 0.1 ± 0.0 (R) | 7.1 ± 2.8 (MS) |
| L203 | PX3834 | 1 | 0.1 ± 0.0 (R) | 6.4 ± 3.0 (MS) |
| L297 | PX3834 | 2 | 0.1 ± 0.0 (R) | 7.9 ± 2.6 (MS) |
| L313 | PX3834 | 1 | 0.1 ± 0.1 (R) | 9.1 ± 3.2 (MS) |

[1]Six-week-old Xa10 transgenic plants and wild-type plants were inoculated with *Xanthomonas oryzae* pv. *oryzae* strain PXO99(pHM1avrXa10). Lesion length and disease phenotype of the inoculated plants were scored at two weeks after inoculation.
[2]Copy number of transgene in Nipponbare. N.A., not applicable. N.D., not detected.
[3]The lesion length (L.L.) and the standard deviation of the mean were the average of 16 infected leaves. For score: R, resistant, 0 cm ≤ L.L. ≤ 3.0 cm; MR, moderately resistant, 3.0 cm < L.L. ≤ 6.0 cm; MS, moderately susceptible, 6.0 cm < L.L. ≤ 9.0 cm; S, susceptible, L.L. > 9.0 cm.

TABLE 4

Disease Evaluation of Wild-Type Plants and Homozygous Transgenic Lines L198 and L162 to Different *Xanthomonas oryzae* pv. *oryzae* Strains[1]

| Bacterial strain | Origin | Lesion length (cm) and resistance score[2] | | | |
|---|---|---|---|---|---|
| | | IRBB10A | Nipponbare | L198 | L162 |
| PXO99 | Philippines | 29.6 ± 3.4 (S) | 14.9 ± 3.1 (S) | 13.6 ± 2.2 (S) | 1.4 ± 1.4 (R) |
| PXO99 (pHM1avrXa10) | Yang et al. (2000) | 0.1 ± 0.1(R) | 11.8 ± 2.6(S) | 0.1 ± 0.1 (R) | 2.2 ± 0.3 (R) |
| PXO86 (R2) | Philippines | 0.4 ± 0.3 (R) | 7.4 ± 1.8 (MS) | 0.2 ± 0.1 (R) | 4.5 ± 2.1 (MR) |
| PXO79 (R3) | Philippines | 25.2 ± 2.9 (S) | 10.5 ± 1.8 (S) | 6.3 ± 2.7 (MS) | 0.9 ± 0.7 (R) |
| PXO113 (R4) | Philippines | 26.8 ± 3.5 (S) | 14.3 ± 1.5 (S) | 12.9 ± 5.0 (S) | 1.1 ± 1.4 (R) |
| PXO112 (R5) | Philippines | 0.2 ± 0.1 (R) | 9.9 ± 2.1 (S) | 0.2 ± 0.2 (R) | 2.5 ± 1.3 (R) |
| IXO56 | Indonesia | 30.4 ± 5.9 (S) | 14.7 ± 4.0 (S) | 10.6 ± 3.1 (S) | 1.9 ± 2.0 (R) |
| K202 | Korea | 31.0 ± 4.9 (S) | 12.5 ± 1.8 (S) | 9.0 ± 3.7 (S) | 2.2 ± 2.4 (R) |
| T7174 | Japan | 26.5 ± 3.4 (S) | 15.1 ± 2.0 (S) | 10.7 ± 3.4 (S) | 1.1 ± 0.9 (R) |
| Zhe173 | China | 29.3 ± 3.4 (S) | 13.1 ± 1.6 (S) | 7.6 ± 2.4 (MS) | 1.8 ± 1.3 (R) |

[1]Six-weeks-old plants were inoculated with Xoo. For each strain, at least 16 leaves from four individual plants were inoculated. Transgenic line L198 carries Xa10 subclone SA4686 whereas L162 carries $P_{PR1}$:Xa10:$T_{Nos}$ gene.
[2]The lesion length (L.L.) and the standard deviation of the mean were the average of 16 infected leaves. For score: R, resistant, 0 cm ≤ L.L. ≤ 3.0 cm; MR, moderately resistant, 3.0 cm < L.L. ≤ 6.0 cm; MS, moderately susceptible, 6.0 cm < L.L. ≤ 9.0 cm; S, susceptible, L.L. > 9.0 cm.

Figure 4:
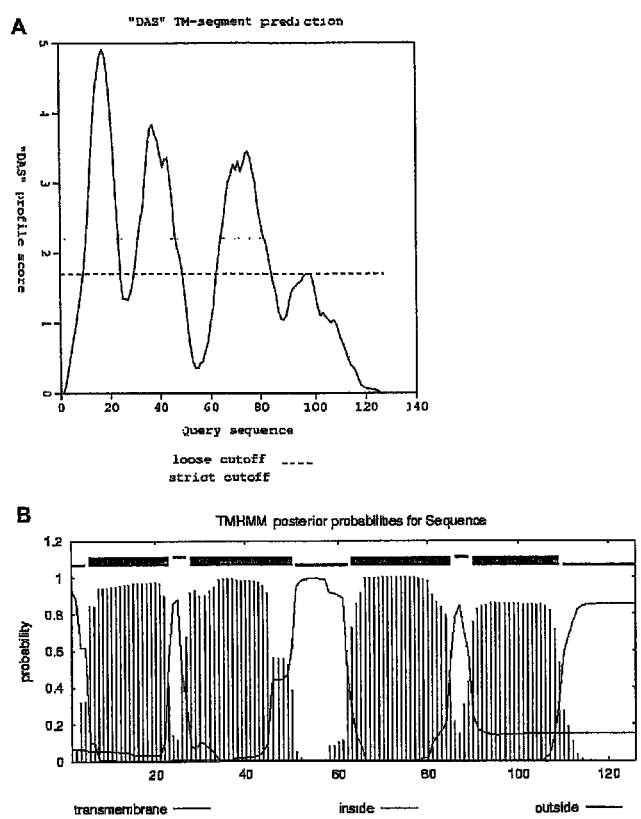
Figure 5:
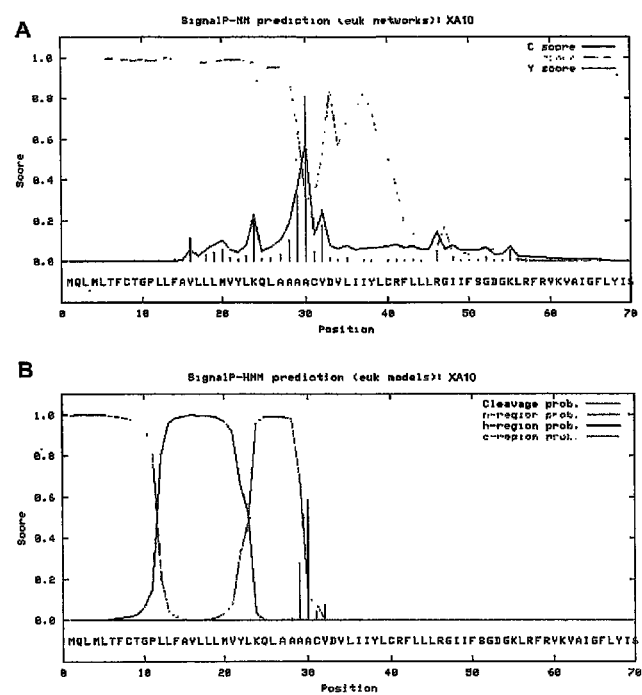

The Xa10 gene encodes a small protein consisting of 126 amino acid residues (XA10; SEQ ID NO:37) (FIG. 1D). XA10 shows 50% identity (54/108) to rice hypothetical protein Os11g37620 (163 aa) and 34% identity (38/109) to another rice hypothetical protein Os11g37570 (134 aa). The two hypothetical proteins might be the paralogs of XA10 in rice genome. The genes encoding the two hypothetical proteins reside on the long arm of rice chromosome 10, but neither of them is allelic to the Xa10 locus. Four transmembrane helices were predicted in XA10 by servers of DAS (hap colon//www dot sbc dot su dot se/~miklos/DAS/) or TMHMM (http colon//www dot cbs dot dtu dot dk/services/TMHMM/), which indicates that XA10 might be a transmembrane protein (FIG. 4). A cleavable signal peptide was also predicted at the N-terminal region of XA10 using SignalP 3.0 server (http colon//www dot cbs dot dtu dot dk/services/SignalP/) (FIG. 5).

Example 3

AvrXa10 Specifically Activates Xa10 Transcription

Figure 6:
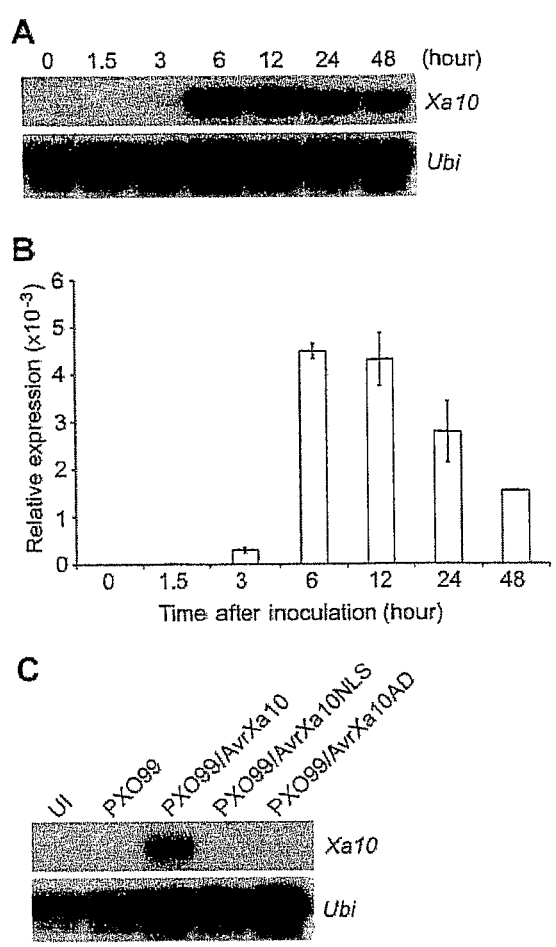

Xa10 was specifically induced in the presence of AvrXa10 (SEQ ID NO:54). No Xa10 transcripts were detected in uninoculated IRBB10A plants or inoculated IRBB10A plants at 1.5 hour after inoculation (HAI) with PXO99 (pHM1avrXa10) (FIGS. 6A and 6B). The Xa10 transcripts were slightly detected at 3 HAI, reached the maximum at 6-12 HAI and remained at high levels at 48 HAI (FIGS. 6A and 6B). Both the NLS motif and the AAD domain are essential for the function of TAL effectors. Indeed, either mutation of the three NLS motifs in AvrXa10 (mutant sequence is SEQ ID NO:56) or deletion of the AAD domain in AvrXa10 (mutant sequence is SEQ ID NO:55) abolished the induction of Xa10 in IRBB10A (FIG. 6C). The specific induction of Xa10 gene by AvrXa10 was also observed in transgenic line L198 that harbored the 4686-bp genomic clone of the Xa10 gene (FIG. 3B). The ectopic expression of the Xa10 coding region driven by rice PR1 promoter in line L162 was highly detected in un-inoculated plants (FIG. 3B). Although it was partially suppressed by bacterial blight inoculation with either Xa10-incompatible or Xa10-compatible strains, the Xa10 transcripts in the inoculated L162 plants were still comparable to that in L198 plants and provided broad-spectrum resistance to both PXO99 (pHM1AvrXa10) and PXO99 (FIG. 3A; Table 4).

Example 4

AvrXa10 Depends on OsTFIIAγ5 for the Activation of Xa10 Transcription

Figure 7:
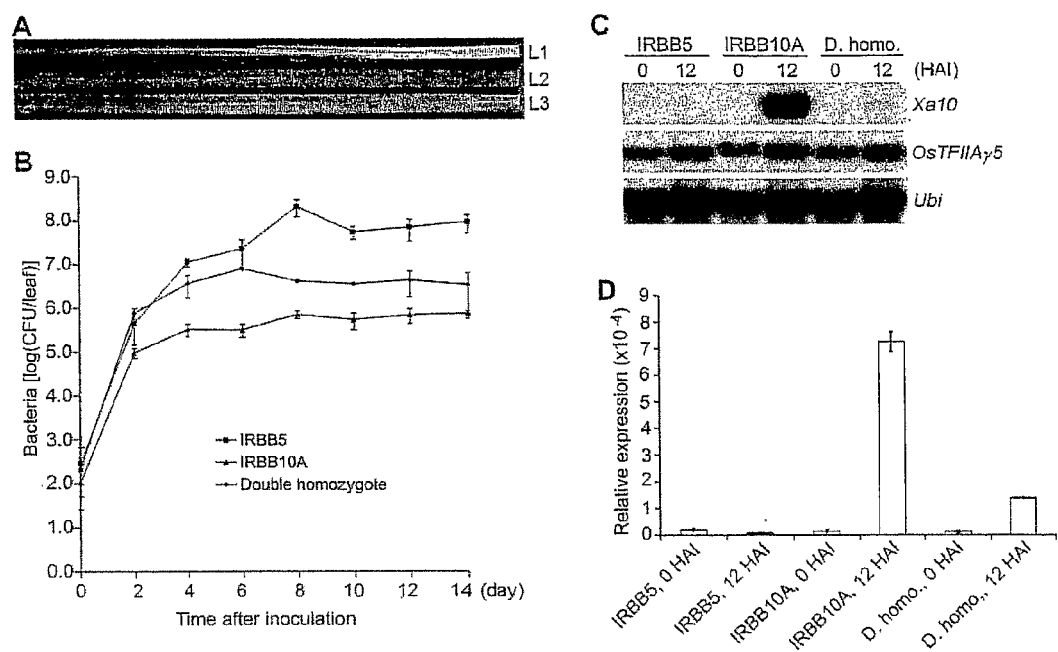

OsTFIIAγ5 is a general transcription factor in rice and its V39E substitution, encoded by the recessive resistance gene xa5 in rice, greatly attenuated the induction of the Xa27 gene in xa5 and Xa27 double homozygote upon inoculation with Xa27 incompatible strains (Gu et al., 2009). To check whether OsTFIIAγ5 is required for induction of the Xa10 gene by AvrXa10, we generated xa5 and Xa10 double homozygous plants from the cross between IRBB5 (xa5/xa5) and IRBB10A (Xa10Xa10). Bacterial blight inoculated with Xoo strain PXO99(pHM1avrXa10) indicated that the double homozygous plants showed partial resistant phenotype at 2 weeks after inoculation (WAI) (FIG. 7A). The average lesion length of the plants (Lesion length=3.1±1.6 cm) was longer than that of IRBB10A plants (Lesion length=0.8±0.4 cm) (FIG. 7A). The bacterial population in the double homozygous plants was 3- to 50-fold lower than that in the susceptible IRBB5 plants, whereas the bacterial population in the IRBB10A plants was 34- to 293-fold lower than that in susceptible IRBB5 plants (FIG. 7B). Compared to strong induction of the Xa10 gene in the inoculated IRBB10A plants, the gene was only weakly induced in the inoculated double homozygous plants (FIG. 7C). Quantitative real-time PCR analysis indicated that Xa10 transcripts in the inoculated double homozygous plants was only 17% of that in the inoculated IRBB10A plants (FIG. 7D). These results demonstrated that rice general transcription factor OsTFIIAγ5 is required for the activation of Xa10 transcription by AvrXa0. The identification of the suppression of xa5 on Xa10-mediated resistance to Xoo provides a guideline for breeding resistance to BB using xa5 and Xa10.

Example 5

Identification of AvrXa10 Binding Site in the Xa10 Promoter

Figure 8:
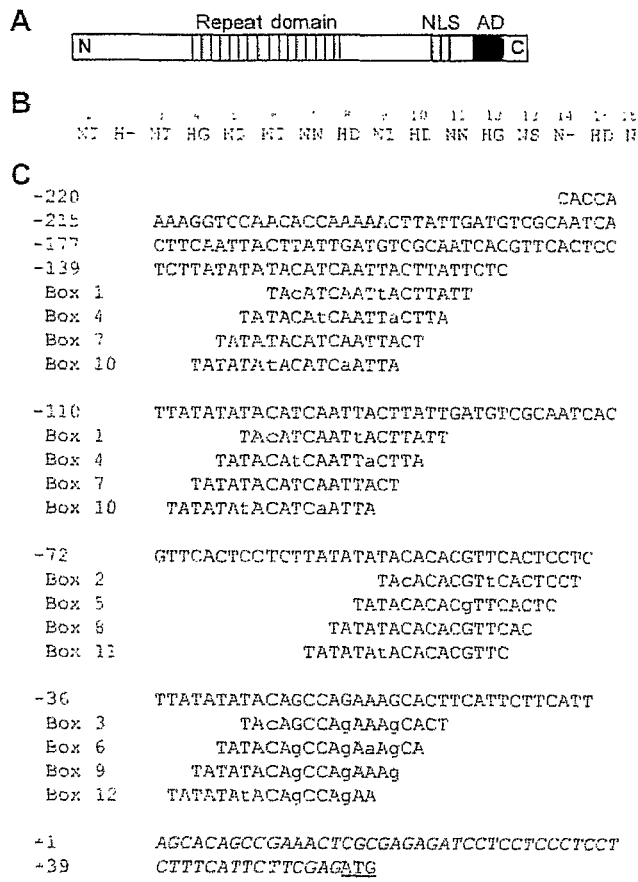
FIGS. 8A-8C show AvrXa10 box candidates in the promoter of Xa10 gene.
Figure 9:
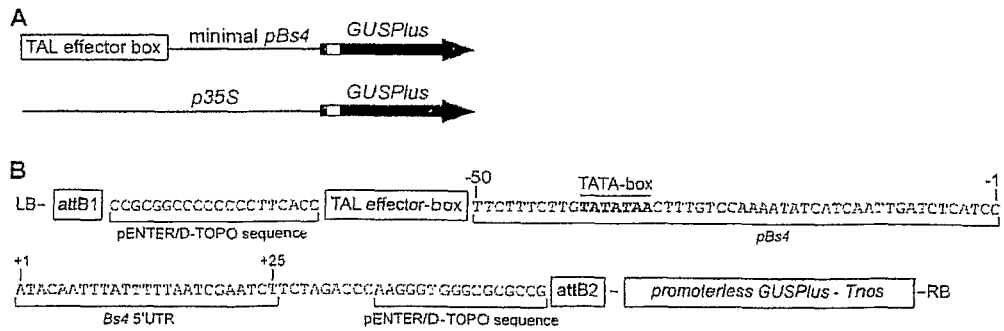
FIGS. 9A and 9B shows GUS reporter constructs.
Figure 10:
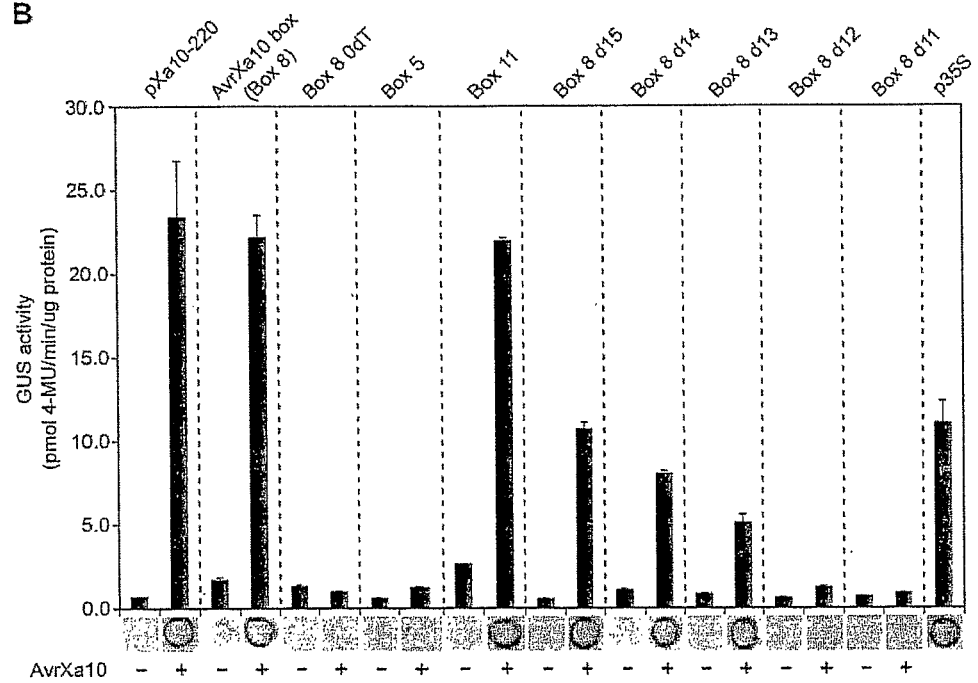
FIGS. 10A and 10B show identification and characterization of AvrXa10 box.

AvrXa10 target DNA sequence (AvrXa10 box) was identified by candidate approach. Based on the model for DNA-target specificity of TAL effectors, in which two hypervariable amino acid residues at positions 12 and 13 in each repeat of TAL effector recognize one base pair in the target DNA (Boch et al., 2009), twelve AvrXa10 box candidates were predicted in the 220-bp Xa10 promoter (FIG. 8). Overlapped boxes 1, 4, 7 and 10 were overlapped and duplicated one time in the 220-bp Xa10 promoter, whereas overlapped boxes 2, 5, 8 and 11 and boxes 3, 6, 9 and 12 formed other two box clusters, respectively (FIG. 8). Xa10 promoters and AvrXa10 box candidates were cloned in front of the minimal Bs4 promoter into an intron-containing GUS (GUSPlus) reporter vector (FIG. 9). Specific inducibility of the AvrXa10 box by AvrXa10 was investigated by transient expression of GUS reporter constructs codelivered via *A. tumefaciens* into *N. benthamiana* leaf cells with 35S-driven avrXa10 gene. Initial study indicated that a 220-bp Xa10 promoter (−1 to −220) (SEQ ID NO:39) was AvrXa10-inducible and should harbor the AvrXa10 box (FIG. 10). Further studies demonstrated that Box 8 and Box 11 were AvrXa10-inducible (FIG. 10). Both candidates harbor the core sequence of the AvrXa10 box that comprises of 13 base pairs at positions 0 to 12 in Box 8 (FIG. 10). Box 8 was thereafter designated as the AvrXa10 box for the following studies.

Example 6

Specific Recognition of AvrXa10 Box by AvrXa10

Figure 11:
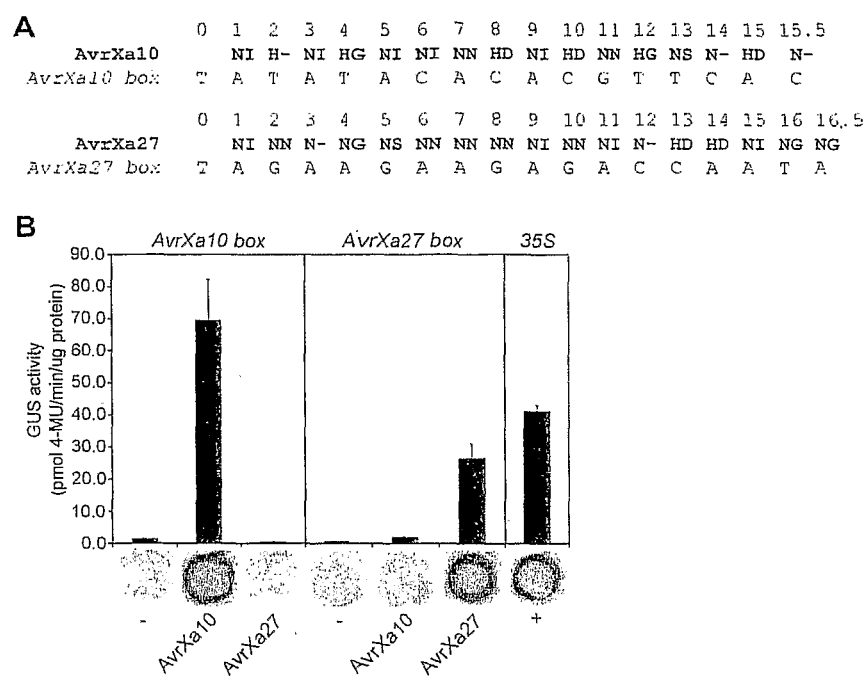
FIGS. 11A and 11B show the recognition specificity of AvrXa10 box and AvrXa27 box by AvrXa10 and AvrXa27, respectively.
Figure 12:
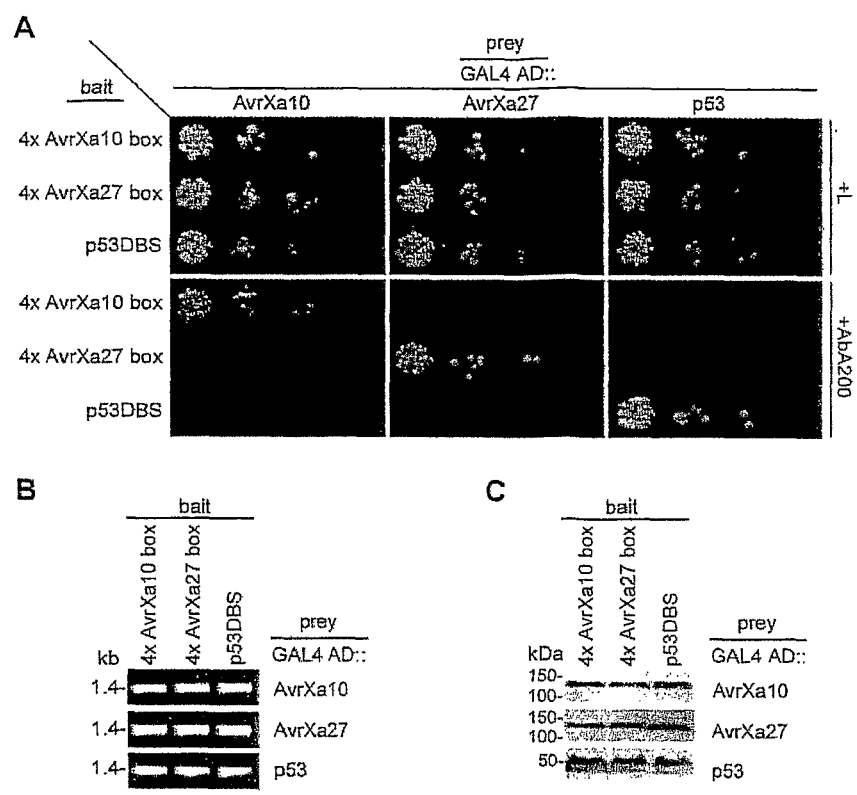
FIGS. 12A-12C show that AvrXa10 and AvrXa27 bind specifically to AvrXa10 box and AvrXa27 box in yeast, respectively.
Figure 13:
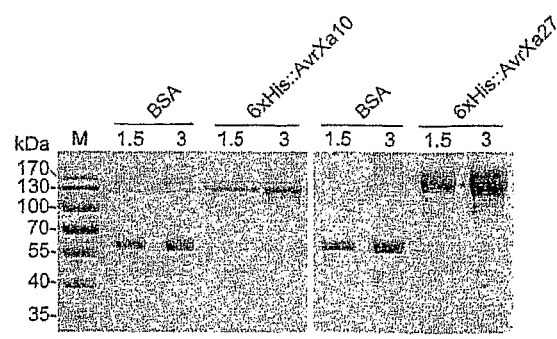
FIG. 13 shows purified 6×His-epitope tagged AvrXa10 and AvrXa27 proteins used in the electromobility shift assay (EMSA) experiments. Protein concentrations were determined by Bradford assay. 1.5 and 3 µg purified 6×His::AvrXa10 (117.5 kDa), 6×His::AvrXa27 (121.0 kDa) and BSA were separated in an 8% SDS polyacrylamide gel and stained with Coomassie brilliant blue. Asterisk marks 6×His::AvrXa10 and 6×His::AvrXa27, respectively.
Figure 14:
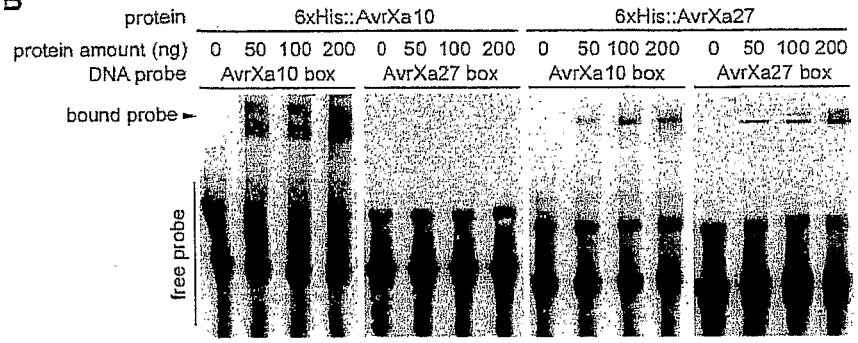
FIGS. 14A-14D show that AvrXa10 binds specifically to AvrXa10 box but not to the AvrXa27 box in an electromobility shift assay (EMSA).
Figure 14:
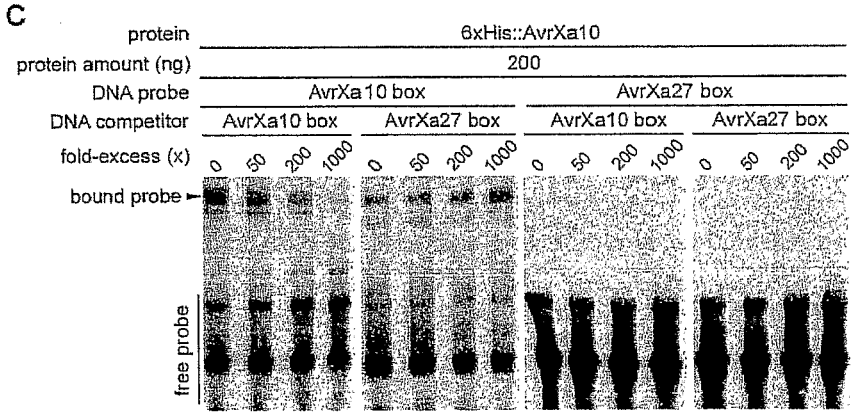
Figure 14:
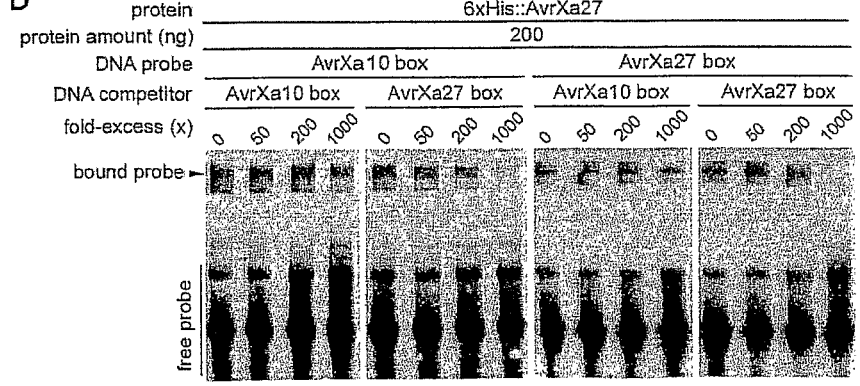

TAL effector AvrXa27 from Xoo strain PXO99 specifically activates expression of the Xa27 gene, another bacterial blight resistance gene in rice (Gu et al., 2005). The nucleotide sequence and the amino acid of the AvrXa27 gene are SEQ ID NO:79 (GenBank Accession No. AY986494) and SEQ ID NO:80 (GenBank Accession No. AAY54168), respectively. AvrXa27 could not activate the susceptible allele of the Xa27 gene (xa27), which shares identical product to that of Xa27 and only shows polymorphism at the promoter region (Gu et al., 2005). AvrXa27 target DNA (UPT$_{AvrXa27}$ box or AvrXa27 box) was identified recently (Romer et al., 2009b). Since no susceptible allele of the Xa10 gene has been identified so far, we then compared the DNA-target specificity of AvrXa10 with that of AvrXa27. Transient expression assay in *N. benthamiana* leaf cells indicated that the AvrXa10 box was specifically recognized by AvrXa10 but not by AvrXa27, and vice versa (FIG. 11). The recognition of the AvrXa10 box by AvrXa10 or the AvrXa27 box by AvrXa27 also occurred in yeast as demonstrated by yeast one-hybrid assay (FIG. 12). The physical interaction between 6×His::AvrXa10 (FIG. 13) and AvrXa10 box or 6×His::AvrXa27 (FIG. 13) and AvrXa27 box was then tested via electromobility shift assay (EMSA) (FIG. 14). AvrXa10 binds with high affinity to AvrXa10 box probe but not to the AvrXa27 box probe (FIG. 14B). Importantly, binding of AvrXa10 to the AvrXa10 box probe could be readily out-competed by non-labeled AvrXa10 box probes, whereas even 1000-fold excess of nonlabeled AvrXa27 box probe could not out-compete the binding (FIG. 14C). Intricately, AvrXa27 binds to both AvrXa10 box probe and AvrXa27 box probe (FIG. 14B). The binding of AvrXa27 to AvrXa10 box probe or AvrXa27 box probe could be out-competed by 1000-fold excess of nonlabeled AvrXa27 box probe but not by the same amount of cold AvrXa10 box probe (FIG. 14D). These data demonstrate that AvrXa10 has a specific high affinity to the Xa10 promoter, whereas AvrXa27 binds with less specificity to DNA sequence, at least in EMSA. Further more, it might be an artifact for AvrXa27 to bind to AvrXa10 box probe in EMSA as AvrXa27 does not physically interact with AvrXa10 box in yeast demonstrated in yeast-one-hybrid assay (FIG. 12).

Example 7

Identification of Essential Nucleotides in AvrXa10 Box for AvrXa10 Binding and Transcription Activation To further investigate the contribution of each individual nucleotide of the AvrXa10 box to AvrXa10 binding, we made 17 AvrXa10 box deletion mutants with each having one nucleotide deletion (FIG. 15A). The first four nucleotides in the AvrXa10 box (positions 0 to 3) are essential for the binding of AvrXa10 to the AvrXa10 box or Xa10 promoter. Deletion at either one of the four nucleotides in the AvrXa10 box abolished AvrXa10 box activity and impaired or significantly affected the binding of AvrXa10 to the mutant probes in EMSA (FIGS. 15B and 15C). Deletion of either one of the nucleotides at positions 4 to 11 also abolished the AvrXa10 box activity but did not significantly affect the binding of AvrXa10 to the mutant probes in EMSA (FIGS. 15B and 15C). Previous deletion from the 3' of the AvrXa10 box indicated that nucleotide "T" at position 12 is required for AvrXa10 box activity (FIG. 10). Therefore, deletion of either one of the two nucleotides "T" at position 12 and 13 did not affect AvrXa10 box activity and the binding of AvrXa10 to the two mutant probes (FIGS. 15B and 15C). Finally, as anticipated, deletion of either one of the last three nucleotides in AvrXa10 box (positions 12 to 17) did not significantly affect AvrXa10 box activity of the mutants and the binding of AvrXa10 to the mutant probes (FIGS. 15B and 15C).

Figure 15:
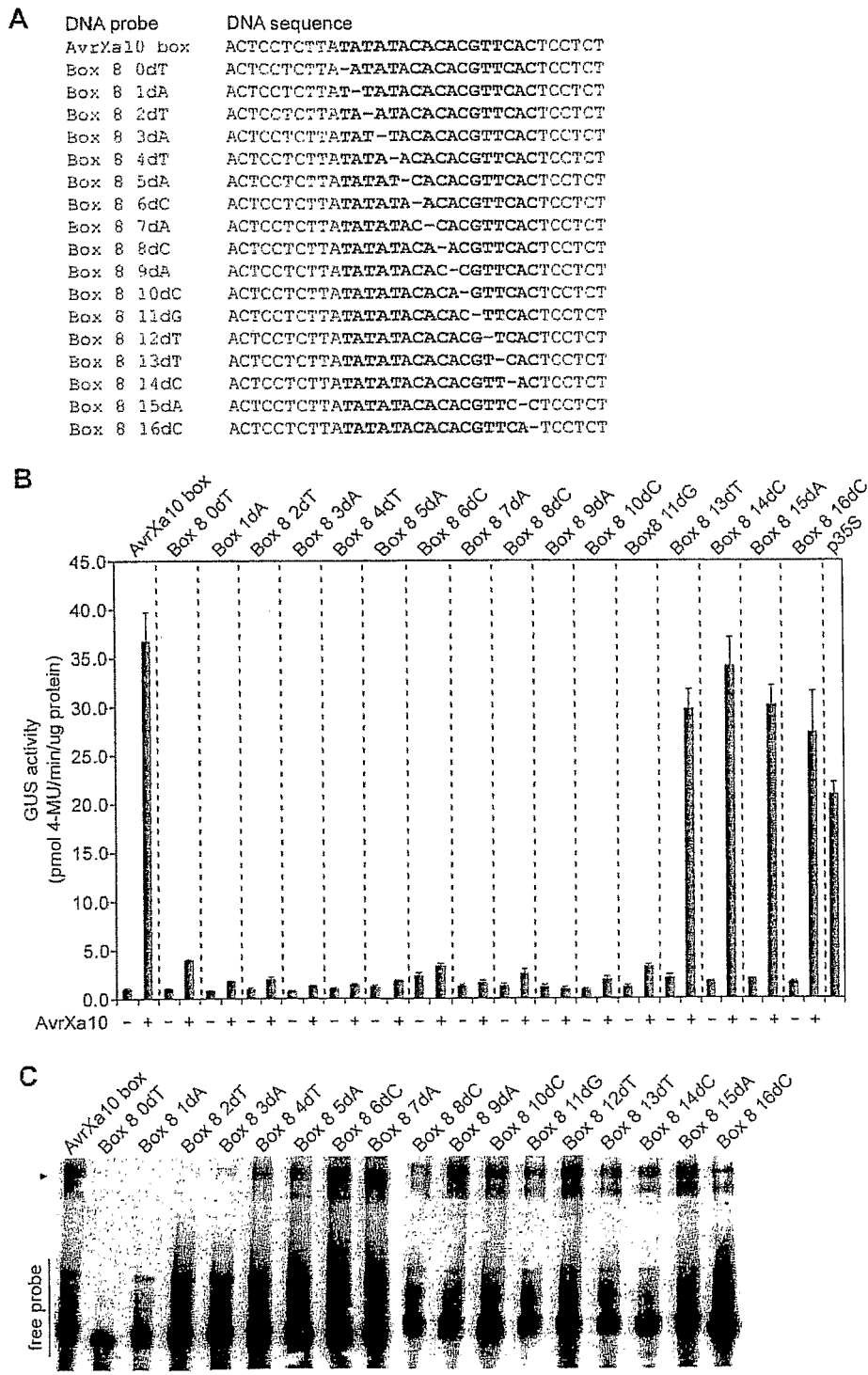
FIGS. 15A-15C show the characterization of deletion mutants of AvrXa10 box in electromobility shift assay (EMSA).
Figure 16:
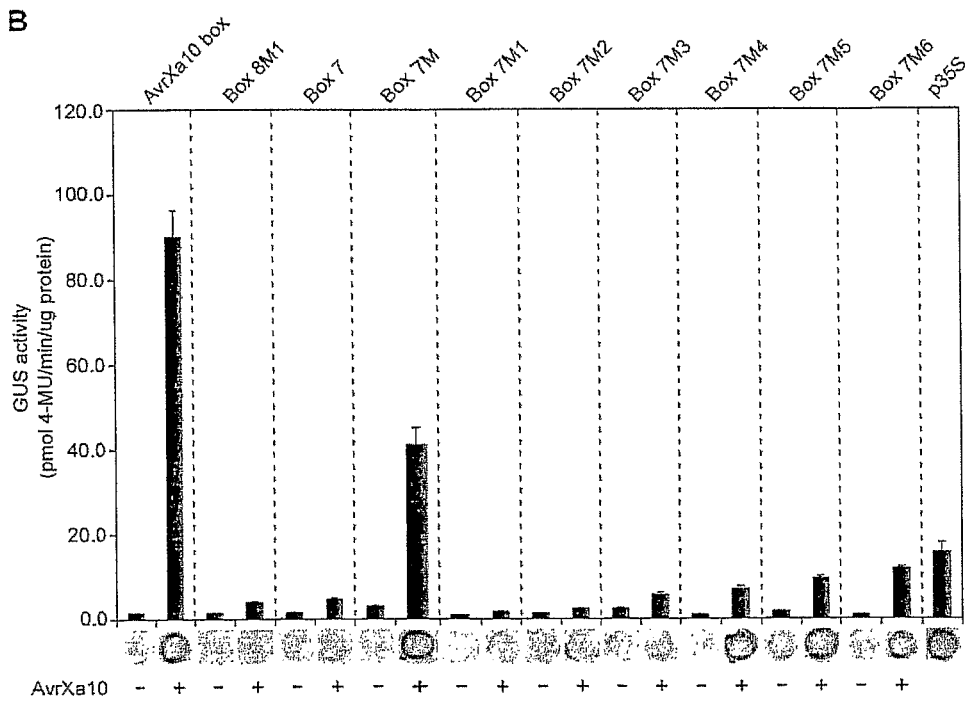
FIGS. 16A and 16B show the recognition specificity of AvrXa10 box, Box 7 and their mutants by AvrXa10.
Figure 17:
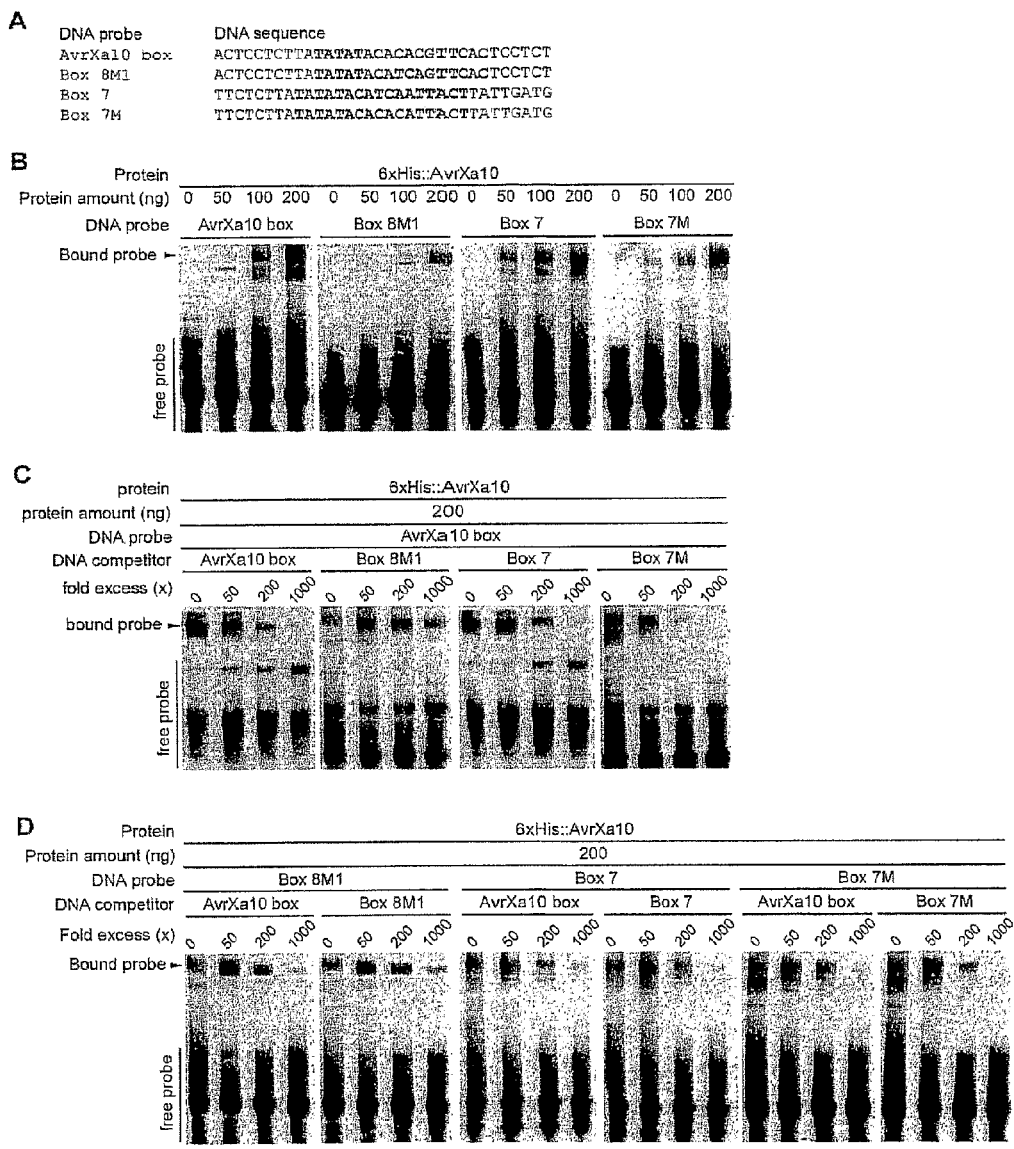
FIGS. 17A-17D show AvrXa10 bind to AvrXa10 box, Box 7 and their mutants in electromobility shift assay (EMSA).
Figure 18:
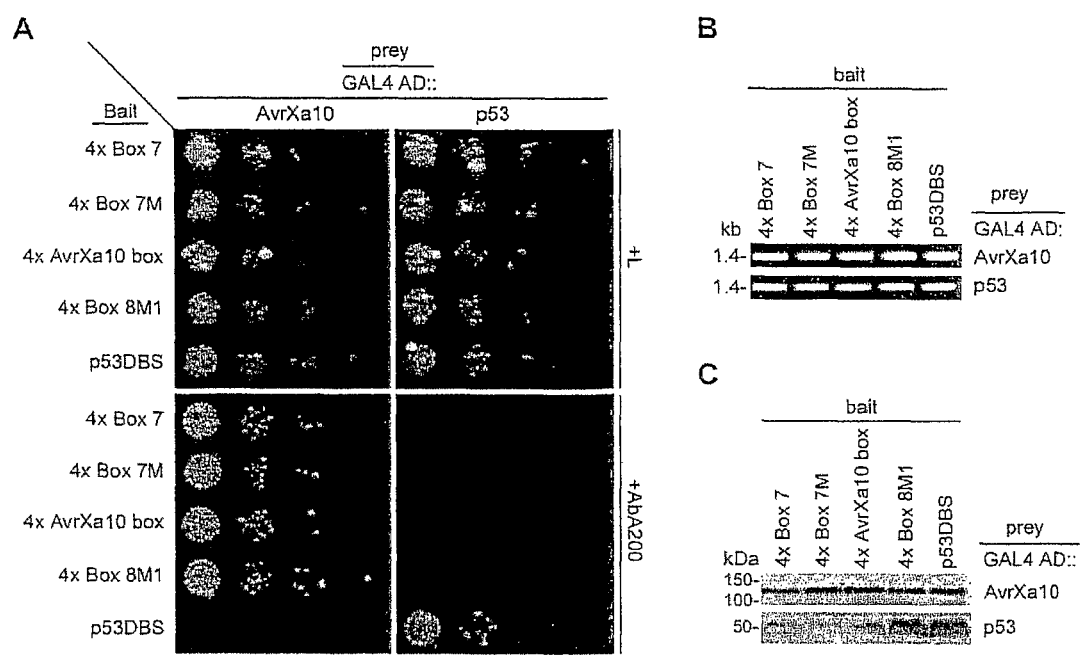
FIGS. 18A-18C show that AvrXa10 bind to Box 7, AvrXa10 box and their mutants in yeast.

The above deletion studies indicated that the core sequence of the AvrXa10 box comprises of 13 base pairs (TATATACACACGT; SEQ ID NO:81) at positions 0-12 (FIG. 15). Within the 13 base pairs, Box 7 and AvrXa10 box show polymorphism at positions 9-12 (FIG. 16A). Previous study also indicated that both "A" and "G" are functional at position 11 in predicted target DNA sequences for AvrXa10 (Boch et al., 2009; Dongsheng Tian and Zhongchao Yin, unpublished data). Therefore, nucleotides at positions 9-11 of AvrXa10 box (CAC) and Box 7 (TCA) may determine their specificities in activation of transcription. To confirm this hypothesis, we generated mutants for AvrXa10 box and Box 7 (FIG. 16A). Mutant Box 8M1 contained "TCA" at positions 9 to 11 in AvrXa10 box background, whereas mutant Box 7M harbored "CAC" at the same positions in Box 7 background (FIG. 16A). Transient expression assay for GUS activity in *N. benthamiana* leaf cells indicated Box 8M1 completely abolish AvrXa10 box activity, whereas Box 7M showed AvrXa10 box activity in induction of GUS reporter gene (FIG. 16B). Mutants with change of either one nucleotide of the "TCA" in Box 7 (Box 7M1, Box 7M2 and Box 7M3) to the corresponding nucleotide in the AvrXa10 box did not significantly increase their ability in induction of GUS reporter gene (FIG. 16B). However, mutants with change of either two nucleotides of the "TCA" in Box 7 (Box 7M4, Box 7M5 and Box 7M6) to the corresponding nucleotides in the AvrXa10 box partially increased their ability in induction of GUS reporter gene (FIG. 16B). Although neither Box 8M1 nor Box 7 has AvrXa10 box activity, EMSA demonstrated that AvrXa10 binds with similar high affinity to the probes of Box 8M1 and Box 7, as that to the probes of AvrXa10 box and Box 7M1 (FIG. 17). The physical interaction between AvrXa10 and AvrXa10 box, Box 8M1, Box 7, or Box 7M1 was also observed in yeast as demonstrated by yeast-one-hybrid assay (FIG. 18).

These results indicated that AvrXa10 box may have two functional centers: the first four nucleotides (TATA) as AvrXa10 binding center and the three nucleotides at positions 9 to 11 (CAC) as the AvrXa10 transcription activation center. Both centers are essentially required for a functional AvrXa10 box. The binding of AvrXa10 to AvrXa10 box-like DNA elements without the transcription activation center is not sufficient to lead to activation of gene transcription. Other nucleotides in AvrXa10 box may provide a scaffold with minor contribution to AvrXa10 binding and/or activation of transcription.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. For example, if the range 10-15 is disclosed, then 11, 12, 13, and 14 are also disclosed. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

It will be appreciated that the methods and compositions of the instant invention can be incorporated in the form of a variety of embodiments, only a few of which are disclosed herein. Embodiments of this invention are described herein, including the best mode known to the inventors for carrying out the invention. Variations of those embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

BIBLIOGRAPHY

Boch J, Scholze H, Schornack S, Landgraf A, Hahn S, Kay S, Lahaye T, Nickstadt A, Bonas U. (2009). Breaking the code of DNA binding specificity of TAL-type III effectors. Science. 326:1509-1512.

Christensen, A. H. and Quail, P. H, (1989). Sequence analysis and transcriptional regulation by heat shock of polyubiquitin transcripts from maize. *Plant Mol Biol* 12:619-632.

Christensen, A. H. et al. (1992). Maize polyubiquitin genes: structure, thermal perturbation of expression and transcript splicing, and promoter activity following transfer to protoplasts by electroporation. *Plant Mol Biol* 18:675-689.

Chu Z H, Yuan M, Yao J L, Ge X J, Yuan B, Xu C G, Li X H, Fu B Y, Li Z K, Bennetzen J L, Zhang Q F, Wang S P (2006). Promoter mutations of an essential gene for pollen development result in disease resistance in rice. Genes Dev 20:1-5.

Gu K, Tian D, Yang F, Wu L, Sreekala C, Wang D, Wang G L, Yin Z (2004). High-resolution genetic mapping of Xa27(t), a new bacterial blight resistance gene in rice, *Oryza sativa* L. Theor Appl Genet 108:800-807.

Gu K, Yang B, Tian D, Wu L, Wang D, Sreekala C, Yang F, Chu Z, Wang G L, White F F, Yin Z (2005). R gene expression induced by a type-III effector triggers disease resistance in rice. Nature 435:1122-1125.

Gu K, Singh J S, Li Y, Yin Z (2008). High-resolution genetic mapping of bacterial blight resistance gene Xa10. Theor Appl Genet 116: 155-163.

Gu K, Tian D, Qiu C, Yin Z (2009). Transcription activator-like type III effector AvrXa27 depends on OsTFI-IAgamma5 for the activation of Xa27 transcription in rice that triggers disease resistance to *Xanthomonas oryzae* pv. *oryzae*. Mol Plant Pathol. 10:829-835.

He S Y, Nomura K, Whittam T S (2004). Type III protein secretion mechanism in mammalian and plant pathogens. *Biochem. Biophys. Acta.* 1694, 181-206.

Heuer H, Yin Y-N, Xue Q-Y, Smalla K, Guo J-H (2007). Repeat domain diversity of avrBs3/pthA-like genes in *Ralstonia solanacearum* strains and association with host preferences in the field. *Appl Environ Microbiol* 73:4379-4384.

Hopkins C M, White F F, Choi S H, Guo A and Leach J E (1992). Identification of a family of avirulence genes from *Xanthomonas oryzae* pv. *oryzae*. Mol Plant-Microbe Inter 5: 451-459.

Iyer A S, McCouch S R (2004). The rice bacterial blight resistance gene xa5 encodes a novel form of disease resistance. Mol Plant-Microbe Inter 17:1348-1354.

Kauffman H E, Reddy A P K, Hsieh S P Y, Merca S D (1973). An improved technique for evaluating resistance to rice varieties of *Xanthomonas oryzae*. Plant Dis Rep 57:537-541.

Kay S, Hahn S, Marois E, Hause G, Bonas U. (2007). A bacterial effector acts as a plant transcription factor and induces a cell size regulator. Science. 318:648-651.

Kay S, Hann S, Marois E, Wieduwild R, Bonas U (2009). Detailed analysis of the DNA recognition motifs of the *Xanthomonas* type III effectors AvrBs3 and AvrBs3Deltarep16. Plant J. 59:859-871.

Last, D. I. et al. (1991). pEmu: an improved promoter for gene expression in cereal cells. *Theor Appl Genet* 81:581-588.

McElroy, D. et al. (1990). Isolation of an efficient actin promoter for use in rice transformation. *Plant Cell* 2:163-171.

Mew T W (1987). Current status and future prospects of research on bacterial blight of rice. Annu Rev Phytopathol 25: 359-382.

Mew T W, Vera Cruz C M and Reyes R C (1982). Interaction of *Xanthomonas campestris* pv. *oryzae* and a resistant rice cultivar. Phytopathology 72:786-789.

Miki D and Shimamoto K (2004). Simple RNAi Vectors for Stable and Transient Suppression of Gene Function in Rice. Plant and Cell Physiology. 45:490-495.

Nino-Liu D O, Ronald P C and Bogdanove A J (2006). *Xanthomonas oryzae* pathovars: model pathogens of a model crop. Mol. Plant Pathol. 7:303-324.

Odell, J. T. et al. (1985). Identification of DNA sequences required for activity of the cauliflower mosaic virus 35S promoter. *Nature* 313:810-812.

Ogawa T, Yamamoto T, Khush G S, Mew T W, Kaku H (1988). Near-isogenic lines as international differentials for resistance to bacterial blight of rice. Rice Genet Newsl 5:106-107.

Romer P, Hahn S, Jordan T, Strauss T, Bonas U, Lahaye T (2007). Plant pathogen recognition mediated by promoter activation of the pepper Bs3 resistance gene. Science. 318: 645-648.

Romer P, Strauss T, Hahn S, Scholze H, Morbitzer R, Grau J, Bonas U, Lahaye T (2009a). Recognition of AvrBs3-like proteins is mediated by specific binding to promoters of matching pepper Bs3 alleles. Plant Physiol. 150:1697-1712.

Romer P, Recht S, Lahaye T (2009b). A single plant resistance gene promoter engineered to recognize multiple TAL effectors from disparate pathogens. Proc Natl Acad Sci USA. 106:20526-20531.

Sambrook, J, Fritsch E F, Maniatis T (1989). Molecular cloning: a laboratory manual, 2nd ed., Cold Spring Harbor Laboratory Press, Cold Spring Harbor.

Schornack S, Meyer A, Romer P, Jordan T, Lahaye T (2006). Gene-for-gene mediated recognition of nuclear-targeted AvrBs3-like bacterial effector proteins. *J Plant Physiol* 163:256-272.

Song W Y, Wang G L, Chen L L, Kim H S, Pi L Y, Holsten T, Gardner J, Wang B, Zhai W X, Zhu L H, Fauquet C, Ronald P (1995). A receptor kinase-like protein encoded by the rice disease resistance gene, Xa21. Science 270:1804-1806.

Strong S J, Ohta Y, Litman G W, Amemiya C T (1997). Marked improvement of PAC and BAC cloning is achieved using electroelution of pulse-field gel-separated partial digests of genomic DNA. Nucleic acids Res 25: 3959-3961.

Sugio A, Yang B, Zhu T, White FF (2007). Two type III effector genes of *Xanthomonas oryzae* pv. *oryzae* control the induction of the host genes OsTFIIAgamma1 and OsTFX1 during bacterial blight of rice. Proc Natl Acad Sci USA 104(25):10720-10725.

Sun X L, Cao Y L, Yang Z F, Xu C G, Li X H, Wang S P, Zhang Q F (2004). Xa26, a gene conferring resistance to *Xanthomonas oryzae* pv. *Oryzae* in rice, encoding an LRR receptor kinase-like protein. Plant J 37:517-527.

Velten, J. et al. (1984). Isolation of a dual plant promoter fragment from the Ti plasmid of *Agrobacterium tumefaciens*. *EMBO J* 3:2723-2730.

Wu L, Goh M L, Sreekala C, Yin Z. (2008). XA27 depends on an amino-terminal signal-anchor-like sequence to localize to the apoplast for resistance to *Xanthomonas oryzae* pv *oryzae*. Plant Physiol. 148:1497-1509.

Yang B, Sugio A, White F F (2006). Os8N3 is a host disease-susceptibility gene for bacterial blight of rice. Proc Natl Acad Sci USA. 103:10503-10508.

Yin Z, Wang G L (2000). Evidence of multiple complex patterns of T-DNA integration into the rice genome. Theor Appl Genet 100, 461-470.

Yoshimura S, Yamanouchi U, Katayose Y, Toki S, Wang Z X, Kono I, Kurata N, Yano M, Iwata N, Sasaki T (1998). Expression of Xa1, a bacterial blight-resistance gene in rice, is induced by bacterial inoculation. Proc Natl Acad Sci USA 95:1663-1668.

Yoshimura A, Mew T W, Khush G S, Moura T (1983). Inheritance of resistance to bacterial blight in rice cultivar Cas 209. Phytopathology 73:1409-1412.

Yoshimura 5, Yoshimura A, Iwata N, McCouch S R, Abenes M L, Baraoidan M R, Mew T W, Nelson R J (1995). Tagging and combining bacterial blight resistance genes in rice using RAPD and RFLP markers. Molecular Breeding 1:375-387.

What is claimed is:

1. A nucleic acid construct comprising a heterologous chimeric plant operable promoter operatively linked to a nucleic acid encoding the transcription activator-like (TAL) effector-dependent Xa10 polypeptide having the amino acid sequence set forth in SEQ ID NO:37, wherein the promoter further comprises SEQ ID NO:23.

2. The nucleic acid construct of claim 1, wherein the nucleic acid encoding the Xa10 polypeptide has the nucleotide sequence set forth in SEQ ID NO:35 or the nucleotide sequence set forth in nucleotides 2423-3234 of SEQ ID NO:35 or the nucleotide sequence set forth in nucleotides 54-437 of SEQ ID NO:36.

3. The nucleic acid construct of claim 1, further operatively linked to a nucleic acid encoding a heterologous polypeptide.

4. A vector comprising the nucleic acid construct of claim 1.

5. The nucleic acid construct of claim 1, wherein the plant operable promoter is selected from the group consisting of a tissue-specific promoter, a constitutive promoter and an inducible promoter.

6. A plant cell comprising the nucleic acid construct of claim 1 or a vector comprising said nucleic acid construct.

7. A transgenic plant that is resistant to *Xanthomonas* comprising the cell of claim 6.

8. The transgenic plant of claim 7, wherein the plant is rice.

9. The transgenic plant of claim 7, wherein the plant is selected from the group consisting of barley, oats, wheat, corn, cabbage, broccoli, potato, tomato, pepper, chili, soybean and rapeseed.

10. A method of enhancing resistance to *Xanthomonas* in a plant having resistance to *Xanthomonas* comprising transfecting the nucleic acid construct of claim 1 or a vector comprising said nucleic acid construct into a plant cell or plant cells from the plant having resistance to *Xanthomonas* and growing a transfected plant from the transfected plant cell or transfected plant cells, wherein the nucleic acid is expressed in the transfected plant and wherein the enhanced resistance of the transfected plant is compared to a plant not having the nucleic acid construct or the vector.

11. A method of conferring resistance to *Xanthomonas* disease to a plant susceptible to *Xanthomonas* comprising transfecting the nucleic acid construct of claim 1 or a vector comprising said nucleic acid construct into a plant cell or plant cells from the plant susceptible to *Xanthomonas* and growing a transfected plant from the transfected plant cell or transfected plant cells, wherein the nucleic acid is expressed in the transfected plant and wherein the conferred resistance of the transfected plant is compared to a plant not having the nucleic acid construct or the vector.

12. The method of claim 10, wherein the plant is rice.

13. The method of claim 10, wherein the plant is selected from the group consisting of barley, oats, wheat, corn, cabbage, broccoli, potato, tomato, pepper, chili, soybean and rapeseed.

14. The nucleic acid construct of claim 2, further operatively linked to a nucleic acid encoding a heterologous polypeptide.

15. A vector comprising the nucleic acid construct of claim 2.

16. The nucleic acid construct of claim 15, wherein the plant operable promoter is selected from the group consisting of a tissue-specific promoter, a constitutive promoter and an inducible promoter.

17. A plant cell comprising the nucleic acid construct of claim 2 or a vector comprising said nucleic acid construct.

18. A transgenic plant that is resistant to *Xanthomonas* comprising the cell of claim 17.

19. The transgenic plant of claim 18, wherein the plant is rice.

20. The transgenic plant of claim 18, wherein the plant is selected from the group consisting of barley, oats, wheat, corn, cabbage, broccoli, potato, tomato, pepper, chili, soybean and rapeseed.

21. The method of claim 11, wherein the plant is rice.

22. The method of claim 11, wherein the plant is selected from the group consisting of barley, oats, wheat, corn, cabbage, broccoli, potato, tomato, pepper, chili, soybean and rapeseed.

23. A method of enhancing resistance to *Xanthomonas* in a plant having resistance to *Xanthomonas* comprising transfecting the nucleic acid construct of claim 2 or a vector comprising said nucleic acid construct into a plant cell or plant cells from the plant having resistance to *Xanthomonas* and growing a transfected plant from the transfected plant cell or transfected plant cells, wherein the nucleic acid is expressed in the transfected plant and wherein the enhanced resistance of the transfected plant is compared to a plant not having the nucleic acid construct or the vector.

24. The method of claim 23, wherein the plant is rice.

25. The method of claim 23, wherein the plant is selected from the group consisting of barley, oats, wheat, corn, cabbage, broccoli, potato, tomato, pepper, chili, soybean and rapeseed.

26. A method of conferring resistance to *Xanthomonas* disease to a plant susceptible to *Xanthomonas* comprising transfecting the nucleic acid construct of claim 2 or a vector comprising said nucleic acid construct into a plant cell or plant cells from the plant susceptible to *Xanthomonas* and growing a transfected plant from the transfected plant cell or transfected plant cells, wherein the nucleic acid is expressed in the transfected plant and wherein the conferred resistance of the transfected plant is compared to a plant not having the nucleic acid construct or the vector.

27. The method of claim 26, wherein the plant is rice.

28. The method of claim 26, wherein the plant is selected from the group consisting of barley, oats, wheat, corn, cabbage, broccoli, potato, tomato, pepper, chili, soybean and rapeseed.

29. The method of claim 10, wherein the resistance is characterized by a lesion length of less than or equal to 6.0 cm in infected leaves.

30. The method of claim 11, wherein the susceptibility is characterized by a lesion length of greater than 6.0 cm in infected leaves.

31. The method of claim 23, wherein the resistance is characterized by a lesion length of less than or equal to 6.0 cm in infected leaves.

32. The method of claim 26, wherein the susceptibility is characterized by a lesion length of greater than 6.0 cm in infected leaves.

* * * * *

SEQUENCE LISTING

<160> NUMBER OF SEQ ID NOS: 97

<210> SEQ ID NO 1
<211> LENGTH: 27
<212> TYPE: DNA
<213> ORGANISM: Oryza sativa
<220> FEATURE:
<221> NAME/KEY: misc_feature
<222> LOCATION: (26)..(26)
<223> OTHER INFORMATION: n may be g, a or c
<220> FEATURE:
<221> NAME/KEY: misc_feature
<222> LOCATION: (27)..(27)
<223> OTHER INFORMATION: n may be a, c, t or g

<400> SEQUENCE: 1
tttttttttt tttttttttt tttttnn                                           27

```
<210> SEQ ID NO 2
<211> LENGTH: 22
<212> TYPE: DNA
<213> ORGANISM: Oryza sativa

<400> SEQUENCE: 2
taagaaggag tagccaagct ca                                              22

<210> SEQ ID NO 3
<211> LENGTH: 22
<212> TYPE: DNA
<213> ORGANISM: Oryza sativa

<400> SEQUENCE: 3
cctcgtcgtc ttcaccaatg ca                                              22

<210> SEQ ID NO 4
<211> LENGTH: 22
<212> TYPE: DNA
<213> ORGANISM: Oryza sativa

<400> SEQUENCE: 4
ccggtttctc tttattaacc gt                                              22

<210> SEQ ID NO 5
<211> LENGTH: 28
<212> TYPE: DNA
<213> ORGANISM: Oryza sativa
<220> FEATURE:
<221> NAME/KEY: misc_feature
<222> LOCATION: (28)..(28)
<223> OTHER INFORMATION: n may be g, a or c

<400> SEQUENCE: 5
aagcagtggt atcaacgcag agttttn                                         28

<210> SEQ ID NO 6
<211> LENGTH: 20
<212> TYPE: DNA
<213> ORGANISM: Saccharomyces cerevisiae

<400> SEQUENCE: 6
ccaagaagat gtaagcaccc                                                 20

<210> SEQ ID NO 7
<211> LENGTH: 33
<212> TYPE: DNA
<213> ORGANISM: Oryza sativa

<400> SEQUENCE: 7
gaccacgcgt atcgatgtcg acttttttt ttt                                   33

<210> SEQ ID NO 8
<211> LENGTH: 21
<212> TYPE: DNA
<213> ORGANISM: Oryza sativa

<400> SEQUENCE: 8
gacgtgctca tcatctacct c                                               21

<210> SEQ ID NO 9
<211> LENGTH: 22
<212> TYPE: DNA
<213> ORGANISM: Oryza sativa
```

<400> SEQUENCE: 9
gaccacgcgt atcgatgtcg ac                                    22

<210> SEQ ID NO 10
<211> LENGTH: 19
<212> TYPE: DNA
<213> ORGANISM: Oryza sativa

<400> SEQUENCE: 10
tgccgtcctc ctactgatg                                        19

<210> SEQ ID NO 11
<211> LENGTH: 20
<212> TYPE: DNA
<213> ORGANISM: Oryza sativa

<400> SEQUENCE: 11
cctcgtcgtc ttcaccaatg                                       20

<210> SEQ ID NO 12
<211> LENGTH: 20
<212> TYPE: DNA
<213> ORGANISM: Oryza sativa

<400> SEQUENCE: 12
ccagtaagtc ctcagccatg                                       20

<210> SEQ ID NO 13
<211> LENGTH: 21
<212> TYPE: DNA
<213> ORGANISM: Oryza sativa

<400> SEQUENCE: 13
tttcagacac catcaaacca g                                     21

<210> SEQ ID NO 14
<211> LENGTH: 19
<212> TYPE: DNA
<213> ORGANISM: Oryza sativa

<400> SEQUENCE: 14
ggcatcatct tctccggcg                                        19

<210> SEQ ID NO 15
<211> LENGTH: 19
<212> TYPE: DNA
<213> ORGANISM: Oryza sativa

<400> SEQUENCE: 15
gcagctatac gggcataag                                        19

<210> SEQ ID NO 16
<211> LENGTH: 17
<212> TYPE: DNA
<213> ORGANISM: Oryza sativa

<400> SEQUENCE: 16
tacatcaatt acttatt                                          17

<210> SEQ ID NO 17
<211> LENGTH: 17
<212> TYPE: DNA
<213> ORGANISM: Oryza sativa

```
<400> SEQUENCE: 17
tacacacgtt cactcct                                                    17

<210> SEQ ID NO 18
<211> LENGTH: 17
<212> TYPE: DNA
<213> ORGANISM: Oryza sativa

<400> SEQUENCE: 18
tacagccaga aagcact                                                    17

<210> SEQ ID NO 19
<211> LENGTH: 17
<212> TYPE: DNA
<213> ORGANISM: Oryza sativa

<400> SEQUENCE: 19
tatacatcaa ttactta                                                    17

<210> SEQ ID NO 20
<211> LENGTH: 17
<212> TYPE: DNA
<213> ORGANISM: Oryza sativa

<400> SEQUENCE: 20
tatacacacg ttcactc                                                    17

<210> SEQ ID NO 21
<211> LENGTH: 17
<212> TYPE: DNA
<213> ORGANISM: Oryza sativa

<400> SEQUENCE: 21
tatacagcca gaaagca                                                    17

<210> SEQ ID NO 22
<211> LENGTH: 17
<212> TYPE: DNA
<213> ORGANISM: Oryza sativa

<400> SEQUENCE: 22
tatatacatc aattact                                                    17

<210> SEQ ID NO 23
<211> LENGTH: 17
<212> TYPE: DNA
<213> ORGANISM: Oryza sativa

<400> SEQUENCE: 23
tatatacaca cgttcac                                                    17

<210> SEQ ID NO 24
<211> LENGTH: 17
<212> TYPE: DNA
<213> ORGANISM: Oryza sativa

<400> SEQUENCE: 24
tatatacagc cagaaag                                                    17

<210> SEQ ID NO 25
<211> LENGTH: 17
<212> TYPE: DNA
```

```
<213> ORGANISM: Oryza sativa

<400> SEQUENCE: 25
tatatataca tcaatta                                          17

<210> SEQ ID NO 26
<211> LENGTH: 17
<212> TYPE: DNA
<213> ORGANISM: Oryza sativa

<400> SEQUENCE: 26
tatatataca cacgttc                                          17

<210> SEQ ID NO 27
<211> LENGTH: 17
<212> TYPE: DNA
<213> ORGANISM: Oryza sativa

<400> SEQUENCE: 27
tatatataca gccagaa                                          17

<210> SEQ ID NO 28
<211> LENGTH: 15
<212> TYPE: DNA
<213> ORGANISM: Oryza sativa

<400> SEQUENCE: 28
tatatacaca cgttc                                            15

<210> SEQ ID NO 29
<211> LENGTH: 14
<212> TYPE: DNA
<213> ORGANISM: Oryza sativa

<400> SEQUENCE: 29
atatacacac gttc                                             14

<210> SEQ ID NO 30
<211> LENGTH: 14
<212> TYPE: DNA
<213> ORGANISM: Oryza sativa

<400> SEQUENCE: 30
tatatacaca cgtt                                             14

<210> SEQ ID NO 31
<211> LENGTH: 13
<212> TYPE: DNA
<213> ORGANISM: Oryza sativa

<400> SEQUENCE: 31
tatatacaca cgt                                              13

<210> SEQ ID NO 32
<211> LENGTH: 12
<212> TYPE: DNA
<213> ORGANISM: Oryza sativa

<400> SEQUENCE: 32
tatatacaca cg                                               12

<210> SEQ ID NO 33
<211> LENGTH: 11
```

```
<212> TYPE: DNA
<213> ORGANISM: Oryza sativa

<400> SEQUENCE: 33
tatatacaca c                                                          11

<210> SEQ ID NO 34
<211> LENGTH: 33
<212> TYPE: DNA
<213> ORGANISM: Oryza sativa

<400> SEQUENCE: 34
actcctctta tatatacaca cgttcactcc tct                                  33

<210> SEQ ID NO 35
<211> LENGTH: 4686
<212> TYPE: DNA
<213> ORGANISM: Oryza sativa
<220> FEATURE:
<221> NAME/KEY: promoter
<222> LOCATION: (1)..(2422)
<220> FEATURE:
<221> NAME/KEY: 5'UTR
<222> LOCATION: (2423)..(2475)
<220> FEATURE:
<221> NAME/KEY: misc_feature
<222> LOCATION: (2476)..(2856)
<223> OTHER INFORMATION: coding sequence
<220> FEATURE:
<221> NAME/KEY: 3'UTR
<222> LOCATION: (2857)..(2872)
<220> FEATURE:
<221> NAME/KEY: Intron
<222> LOCATION: (2873)..(3121)
<220> FEATURE:
<221> NAME/KEY: 3'UTR
<222> LOCATION: (3122)..(3234)

<400> SEQUENCE: 35
aaaaaacaag gttattggcc taggtttatt ggctgagcaa tgcccaattc cacaaagaca      60
tgctggcgtg ctgctgcttg ggcagttggg ctatgttgat ctacattata tattaaaggt    120
aaaaggataa acctttgctc attgataaca ctcaacatga ttagatctaa aagtaaagat    180
gaagccatga acacgttttt taacagagta atccaatcc ttcaaaacac aaaagaaaaa    240
aaaaagagca atgatgaaac acggtattgt tagagtttgt cttgatggac cactagacta    300
gactcgatgg agcaaaccac aatcatcgga taggccctac aacagaagaa ctctcatcca    360
ctctttacct caccgaatct cctcacgaaa ttgaaaggtg ggaattgaga acaaacgtt     420 gaaacatatc ttgatctgag gcacccagcg tctctcaaaa aaaactacag attacatcaa    480
caaagaatct ttttcttctt ccttcctctc tctacctctt cttgagccta attctttctt    540
accaacaaaa actacgtttt gaccatgatt acccactact actacatgat tgtgccgcaa    600
ccgcaaccac caccaccgag cagcaaagca gcagatcggc gacagttaga tcaggcgggg    660
gcctgaactt ggcaagagag gagaagaaag caaagagagg ggaggagatg agacctcgaa    720
tcggatgttc ttgaagacga cctcctcgac gttgctgccg atggtgggtg cggcggtgac    780
ggcctcgccg aggtggagct tgtagagcgt ggtggtcttg ccggcgttgt cgagccccac    840
gacgacgatc ttgtactcct tcgccgggaa catcaagaac cacaccctcg acatccacgc    900
ccccatcttc ttcctctctg tctcctcctc aagcaaccaa gaaaacaccg aatctgaatc    960
tcgcgccgcg gcggctggcg gctggcggtg gatggatctc cgcgggagga agtggactgc    1020
gagtttgggg gatcggatcg gcgatggggg tggaggagga agaacaagag gaggtcggat    1080
```

```
ttggaggagg aaaggtgaga agggaattgg ggtgtggata ttcgtgcgaa gctttcctct    1140
ctcatggcca gccgaggggg atttgggctg ggcctcctgt gggctttggg ctgtggaagt    1200
agagacatgg cgagtgagcc ggaataagtc tactaatctt ccctcgtttt tacgtagagt    1260
ttaatcgaca tccctaaacc gcaataccag gaatcttcac ctttcatctt tgcaaaaccg    1320
tttgacttag gtccgatagc agtatggata ggtgttttcg ctgatgtggc attctagtta    1380
gaaaaaaaaa acatgagggg gtccacatgt aactgagccc atgtattaat tgggcccaca    1440
tgtcagggct ttcttcttcc tctcctctat tcccatttct ctccccaatc tccacctatc    1500
cccttttccc cagtttataa ttgatcatat ttatcattta aactactcaa tatcgacatt    1560
aatttgattg aaaagaaat tagaaaaaat aaaatagaaa aatagaaaaa acggtacggt    1620
cgaaaatagt acctcttaaa cggaaacggc gtccggtcga ttgagaattt ccgtgaccgt    1680
tttcagctgc cataggcttg ggccaagcga caacactttg ggccaagcta aaaacgtctt    1740
gggcttttct gggtcgaaag tcgagctaaa ctcatatgga tccaagtggc tcacggtgta    1800
aatattagta ggattaatcc cacatagata gcttacgaag gttgagagca atatataaat    1860
ccttgcgtcc taacgacagt atatggggaa aaaaattttg tggggggtgtt cgttatatat    1920 gcatgaatat atatacatat atatcttatt atctccccgg gaagcccaat ctctctcccc    1980
gggaagccca atctctctca ggaatttcaa gaacttcaat tgatgaattt atatttataa    2040
ctaagtcaat tggtgatcct attaccggaa cccaaggtcg gttataagtc aattggtgat    2100
cctattaccg gaaggttaag tcaattggtg atcctattac cggaaggtcc aaggtaaaga    2160
ataaccagtt acacaaggtc caaggtaaag aataaccagt tacaccaaaa ggtccaacac    2220
caaaaactta ttgatgtcgc aatcacttca attacttatt gatgtcgcaa tcacgttcac    2280
tcctcttata tatacatcaa ttacttattc tcttatatat acatcaatta cttattgatg    2340
tcgcaatcac gttcactcct cttatatata cacgttca ctcctcttat atatacagcc    2400
agaaagcact tcattcttca ttagcacagc cgaaactcgc gagagatcct cctccctcct    2460
ctttcattct tcgagatgca gctgatgctc acattctgca cgggccccct cctgtttgcc    2520
gtcctcctac tgatggtata cctcaagcaa ctcgccgccg cggcctgcgt cgacgtgctc    2580
atcatctacc tctgccgctt cctcctcctc cgcggcatca tcttctccgg cgacggcaag    2640
ctacgattcc gcgtcaaggt agcgatcggg ttcctctaca tctccctctc ggccatactc    2700
ttctacctct ctgccgctgt catggcgttg ccgccgtggg gtgcggtggc catgtgggga    2760
atggcgctcg tcgccactga gcttggctac tccttcttat gcccgtatag ctgccgctgc    2820
attggtgaag acgacgagga gatttccccc gtctgaggcc catatatatc acgatggata    2880
aacatattac atactccctc cgtttcaaaa tgtttgacac cattgacttt tcagcacatg    2940
tttgaccgtt cgtttcattc aaaaaaaatt gtgaaatatg taaaactata tgtgtacatg    3000
gaaatatatt taacaatgaa tcaaatgata tgaaaagaat aaataattac ttaaattttt    3060
tgaataagac gaatggtgaa acacgtacta aaaagtcaat ggtgtcaaac attttgaaac    3120
ggagggagta ttaattggtt tgttagtttg tgttcattca tatatagctg ttgtattttt    3180
acggttaata aagagaaacc ggcgagcgcc tagcagccgg ctagtttagt caaatttgca    3240
ctatatgtat gttgatactt gattcatcat tcatatcgat cagggtgtcc tagctagctc    3300
gtgtttatat ttacgcttga tgtatgttga tacttgattt catcatccaa atttgcacta    3360
gcttacgtgt tgttccagtt tgttgggggc catcgtcaaa tcacccttaa tttcttgtac    3420
```

-continued

| | |
|---|---|
| cattttggca cgtactacac atgtatccct ccatccttgt agtttgatta tcacttaagt | 3480 |
| aaaggacgtt gacaccaagt acaacgaaac ctctatggtt cgaaaattaa tttgcatcga | 3540 |
| tcaaagatgt gttttgtcgc ttcatgtcat acggattgta tcatgcttgc tttaaatatt | 3600 |
| gcatggagtt acacaaacga aaataatttt tagctgtagt tgtatgcatc actttaattt | 3660 |
| agcgaggaat aatatggatc tgaccacgta ctacgcgatt ctgctcatcg tcgaggtcgt | 3720 |
| cttcgccttc ttcttcctac cgtacagctg cggcagcgac gtcgtggacg agaatatccc | 3780 |
| acatgtctga ccaggggaac gacatcctct gacgagagac gtgttcgctg acacgtgggc | 3840 |
| tccactcccc ttaaactcac atgtcagaaa ttcacgtcac agagcatata ctccatcagt | 3900 |
| cctattatat aagggtttta gatggatgag aagtactacg aatatagata aaaaatgtct | 3960 |
| cgtcgtttat ctaaaatctt ttatattttg ggacagagga aatatatgat caacttagat | 4020 |
| catttcaaaa ccaaaacaaa aactaaaaag cacggtgaac tttgtgtgct accagaccaa | 4080 |
| aatttccttt ggtttgtgtt agttaattac ctaagtgtga tttcttcatg tcaattagtt | 4140 |
| agttgatcca tttggtctta aactaatttc cacgttcgca aataaagcag cagcttgctg | 4200 |
| gctagctagg ccttcatgtt gctcatgtat gcgcacttgt gcagtatgat caatcaggtc | 4260 |
| aatttaatta tcttattaat tatgatgtat atatactccc tccgtcccaa aaagtgaat | 4320 |
| ataaaactga atgtgacata tgcatatcca gattcattgt cacatccagt attatgttgg | 4380 |
| tttttatag aacagaggga gtatgtcact tcaaattgtt ttcaaatctt taatttattt | 4440 |
| cttcttattt ctcgagatct acaacggaag taacaaataa aacctctaaa aatgatcgta | 4500 |
| attctgaaat ttaaaatcgt attatgtcca agatctcgat atactagcca gtactcgatc | 4560 |
| cttatttcat accgtatgaa atccaaggat cagcccagcc cagaccatac agcccacccc | 4620 |
| ggcccgcgta cggaaaccaa cggtctagaa tcgctcgacc gaaaaacgcc aggtgtcaac | 4680 |
| cgcacg | 4686 |

<210> SEQ ID NO 36
<211> LENGTH: 570
<212> TYPE: DNA
<213> ORGANISM: Oryza sativa
<220> FEATURE:
<221> NAME/KEY: CDS
<222> LOCATION: (54)..(431)

<400> SEQUENCE: 36

| | |
|---|---|
| agcacagccg aaactcgcga gagatcctcc tccctcctct ttcattcttc gag atg<br>　　　　　　　　　　　　　　　　　　　　　　　　　　　　　　　　　　Met<br>　　　　　　　　　　　　　　　　　　　　　　　　　　　　　　　　　　1 | 56 |
| cag ctg atg ctc aca ttc tgc acg ggc ccc ctc ctg ttt gcc gtc ctc<br>Gln Leu Met Leu Thr Phe Cys Thr Gly Pro Leu Leu Phe Ala Val Leu<br>　　　　　5　　　　　　　　　　　10　　　　　　　　　　　15 | 104 |
| cta ctg atg gta tac ctc aag caa ctc gcc gcc gcg gcc tgc gtc gac<br>Leu Leu Met Val Tyr Leu Lys Gln Leu Ala Ala Ala Ala Cys Val Asp<br>　　20　　　　　　　　　　　25　　　　　　　　　　　30 | 152 |
| gtg ctc atc atc tac ctc tgc cgc ttc ctc ctc ctc cgc ggc atc atc<br>Val Leu Ile Ile Tyr Leu Cys Arg Phe Leu Leu Leu Arg Gly Ile Ile<br>　35　　　　　　　　　　　40　　　　　　　　　　　45 | 200 |
| ttc tcc ggc gac ggc aag cta cga ttc cgc gtc aag gta gcg atc ggg<br>Phe Ser Gly Asp Gly Lys Leu Arg Phe Arg Val Lys Val Ala Ile Gly<br>50　　　　　　　　　　　55　　　　　　　　　　　60　　　　　　　　　　　65 | 248 |
| ttc ctc tac atc tcc ctc tcg gcc ata ctc ttc tac ctc tct gcc gct<br>Phe Leu Tyr Ile Ser Leu Ser Ala Ile Leu Phe Tyr Leu Ser Ala Ala<br>　　　　　　　　　　　70　　　　　　　　　　　75　　　　　　　　　　　80 | 296 |

```
gtc atg gcg ttg ccg ccg tgg ggt gcg gtg gcc atg tgg gga atg gcg    344
Val Met Ala Leu Pro Pro Trp Gly Ala Val Ala Met Trp Gly Met Ala
        85                  90                  95 ctc gtc gcc act gag ctt ggc tac tcc ttc tta tgc ccg tat agc tgc    392
Leu Val Ala Thr Glu Leu Gly Tyr Ser Phe Leu Cys Pro Tyr Ser Cys
            100                 105                 110 cgc tgc att ggt gaa gac gac gag gag att tcc ccc gtc tgaggcccat    441
Arg Cys Ile Gly Glu Asp Asp Glu Glu Ile Ser Pro Val
115                 120                 125 atatatcacg agggagtatt aattggtttg ttagtttgtg ttcattcata tatagctgtt    501
gtatttttac ggttaataaa gagaaaccgg cgagcgccta gcagccggct agtttagtca    561
aaaaaaaaaa    570

<210> SEQ ID NO 37
<211> LENGTH: 126
<212> TYPE: PRT
<213> ORGANISM: Oryza sativa

<400> SEQUENCE: 37

Met Gln Leu Met Leu Thr Phe Cys Thr Gly Pro Leu Leu Phe Ala Val
1               5                   10                  15

Leu Leu Leu Met Val Tyr Leu Lys Gln Leu Ala Ala Ala Ala Cys Val
            20                  25                  30

Asp Val Leu Ile Ile Tyr Leu Cys Arg Phe Leu Leu Leu Arg Gly Ile
        35                  40                  45

Ile Phe Ser Gly Asp Gly Lys Leu Arg Phe Arg Val Lys Val Ala Ile
    50                  55                  60

Gly Phe Leu Tyr Ile Ser Leu Ser Ala Ile Leu Phe Tyr Leu Ser Ala
65                  70                  75                  80

Ala Val Met Ala Leu Pro Pro Trp Gly Ala Val Ala Met Trp Gly Met
                85                  90                  95

Ala Leu Val Ala Thr Glu Leu Gly Tyr Ser Phe Leu Cys Pro Tyr Ser
            100                 105                 110

Cys Arg Cys Ile Gly Glu Asp Asp Glu Glu Ile Ser Pro Val
        115                 120                 125

<210> SEQ ID NO 38
<211> LENGTH: 2475
<212> TYPE: DNA
<213> ORGANISM: Oryza sativa
<220> FEATURE:
<221> NAME/KEY: promoter
<222> LOCATION: (1)..(2422)
<220> FEATURE:
<221> NAME/KEY: misc_feature
<222> LOCATION: (2423)..(2423)
<223> OTHER INFORMATION: transcription start site

<400> SEQUENCE: 38
aaaaaacaag gttattggcc taggtttatt ggctgagcaa tgcccaattc cacaaagaca     60
tgctggcgtg ctgctgcttg ggcagttggg ctatgttgat ctacattata tattaaaggt    120
aaaaggataa acctttgctc attgataaca ctcaacatga ttagatctaa agtaaagat    180 gaagccatga acacgttttt taacagagta aatccaatcc ttcaaaacac aaaagaaaaa    240
aaaaagagca atgatgaaac acggtattgt tagagtttgt cttgatggac cactagacta    300
gactcgatgg agcaaaccac aatcatcgga taggccctac aacagaagaa ctctcatcca    360
ctctttacct caccgaatct cctcacgaaa ttgaaaggtg ggaattgaga aacaaacgtt    420
```

```
gaaacatatc ttgatctgag gcacccagcg tctctcaaaa aaaactacag attacatcaa    480
caaagaatct tttcttcttc ccttcctctc tctacctctt cttgagccta attctttctt    540
accaacaaaa actacgtttt gaccatgatt acccactact actacatgat tgtgccgcaa    600
ccgcaaccac caccaccgag cagcaaagca gcagatcggc gacagttaga tcaggcgggg    660
gcctgaactt ggcaagagag gagaagaaag caaagagagg ggaggagatg agacctcgaa    720
tcggatgttc ttgaagacga cctcctcgac gttgctgccg atggtgggtg cggcggtgac    780
ggcctcgccg aggtggagct tgtagagcgt ggtggtcttg ccggcgttgt cgagccccac    840
gacgacgatc ttgtactcct tcgccgggaa catcaagaac cacaccctcg acatccacgc    900
ccccatcttc ttcctctctg tctcctcctc aagcaaccaa gaaaacaccg aatctgaatc    960
tcgcgccgcg gcggctggcg gctggcggtg gatggatctc gcggggagga agtggactgc   1020
gagtttgggg gatcggatcg gcgatggggg tggaggagga agaacaagag gaggtcggat   1080
ttggaggagg aaaggtgaga agggaattgg ggtgtggata ttcgtgcgaa gctttcctct   1140
ctcatggcca gccgaggggg atttgggctg gcctcctgt gggctttggg ctgtggaagt    1200
agagacatgg cgagtgagcc ggaataagtc tactaatctt ccctcgtttt tacgtagagt   1260
ttaatcgaca tccctaaacc gcaataccag gaatcttcac ctttcatctt tgcaaaaccg   1320
tttgacttag gtccgatagc agtatggata ggtgttttcg ctgatgtggc attctagtta   1380
gaaaaaaaaa acatgagggg gtccacatgt aactgagccc atgtattaat tgggcccaca   1440
tgtcagggct ttcttcttcc tctcctctat tcccatttct ctccccaatc tccacctatc   1500
cccttttccc cagtttataa ttgatcatat ttatcattta aactactcaa tatcgacatt   1560
aatttgattg aaaagaaat tagaaaaaat aaaatagaaa aatagaaaaa acggtacggt    1620
cgaaaatagt acctcttaaa cggaaacggc gtccggtcga ttgagaattt ccgtgaccgt   1680
tttcagctgc cataggcttg gccaagcga caacactttg ggccaagcta aaaacgtctt    1740
gggcttttct gggtcgaaag tcgagctaaa ctcatatgga tccaagtggc tcacggtgta   1800
aatattagta ggattaatcc cacatagata gcttacgaag gttgagagca atatataaat   1860
ccttgcgtcc taacgacagt atatggggaa aaaaattttg tgggggtgtt cgttatatat   1920
gcatgaatat atatacatat atatcttatt atctccccgg gaagcccaat ctctctcccc   1980
gggaagccca atctctctca ggaatttcaa gaacttcaat tgatgaattt atatttataa   2040
ctaagtcaat tggtgatcct attaccggaa cccaaggtcg gttataagtc aattggtgat   2100
cctattaccg gaaggttaag tcaattggtg atcctattac cggaaggtcc aaggtaaaga   2160
ataaccagtt acacaaggtc caaggtaaag aataaccagt tacaccaaaa ggtccaacac   2220
caaaaactta ttgatgtcgc aatcacttca attacttatt gatgtcgcaa tcacgttcac   2280
tcctcttata tatacatcaa ttacttattc tcttatatat acatcaatta cttattgatg   2340
tcgcaatcac gttcactcct cttatatata cacacgttca ctcctcttat atatacagcc   2400
agaaagcact tcattcttca ttagcacagc cgaaactcgc gagagatcct cctccctcct   2460
ctttcattct tcgag                                                     2475
```

<210> SEQ ID NO 39
<211> LENGTH: 220
<212> TYPE: DNA
<213> ORGANISM: Oryza sativa
<220> FEATURE:
<221> NAME/KEY: promoter
<222> LOCATION: (1)..(220)

<400> SEQUENCE: 39

```
caccaaaagg tccaacacca aaaacttatt gatgtcgcaa tcacttcaat tacttattga      60
tgtcgcaatc acgttcactc ctcttatata tacatcaatt acttattctc ttatatatac     120
atcaattact tattgatgtc gcaatcacgt tcactcctct tatatataca cacgttcact     180
cctcttatat atacagccag aaagcacttc attcttcatt                           220
```

<210> SEQ ID NO 40
<211> LENGTH: 16
<212> TYPE: DNA
<213> ORGANISM: Oryza sativa

<400> SEQUENCE: 40

```
atatacacac gttcac                                                      16
```

<210> SEQ ID NO 41
<211> LENGTH: 276
<212> TYPE: DNA
<213> ORGANISM: Oryza sativa

<400> SEQUENCE: 41

```
caccaaaagg tccaacacca aaaacttatt gatgtcgcaa tcacttcaat tacttattga      60
tgtcgcaatc acgttcactc ctcttatata tacatcaatt acttattctc ttatatatac     120
atcaattact tattgatgtc gcaatcacgt tcactcctct tatatataca cacgttcact     180
cctcttatat atacagccag aaagcacttc attcttcatt agcacagccg aaactcgcga     240
gagatcctcc tccctcctct ttcattcttc gagatg                               276
```

<210> SEQ ID NO 42
<211> LENGTH: 20
<212> TYPE: DNA
<213> ORGANISM: Artificial Sequence
<220> FEATURE:
<223> OTHER INFORMATION: Sequence from pENTER/D-TOPO

<400> SEQUENCE: 42

```
ccgcggccgc cccttcaccc                                                  20
```

<210> SEQ ID NO 43
<211> LENGTH: 100
<212> TYPE: DNA
<213> ORGANISM: Artificial Sequence
<220> FEATURE:
<223> OTHER INFORMATION: Sequence from tomato Bs4 promoter and 5' UTR
      and pENTER/D-TOPO

<400> SEQUENCE: 43

```
ttctttcttg tatataactt tgtccaaaat atcatcaatt gatctcatcc atacaattta      60
tttttaatcg aatcttctag acccaagggt gggcgcgccg                           100
```

<210> SEQ ID NO 44
<211> LENGTH: 18
<212> TYPE: DNA
<213> ORGANISM: Xanthomonas oryzae

<400> SEQUENCE: 44

```
tagaagaaga gaccaata                                                    18
```

<210> SEQ ID NO 45
<211> LENGTH: 34
<212> TYPE: DNA

<213> ORGANISM: Oryza sativa

<400> SEQUENCE: 45
gtgctataaa tagaagaaga gaccaataga gagc        34

<210> SEQ ID NO 46
<211> LENGTH: 32
<212> TYPE: DNA
<213> ORGANISM: Oryza sativa

<400> SEQUENCE: 46
actcctctta atatacacac gttcactcct ct          32

<210> SEQ ID NO 47
<211> LENGTH: 32
<212> TYPE: DNA
<213> ORGANISM: Oryza sativa

<400> SEQUENCE: 47
actcctctta ttatacacac gttcactcct ct          32

<210> SEQ ID NO 48
<211> LENGTH: 32
<212> TYPE: DNA
<213> ORGANISM: Oryza sativa

<400> SEQUENCE: 48
actcctctta taatacacac gttcactcct ct          32

<210> SEQ ID NO 49
<211> LENGTH: 32
<212> TYPE: DNA
<213> ORGANISM: Oryza sativa

<400> SEQUENCE: 49
actcctctta tattacacac gttcactcct ct          32

<210> SEQ ID NO 50
<211> LENGTH: 32
<212> TYPE: DNA
<213> ORGANISM: Oryza sativa

<400> SEQUENCE: 50
actcctctta tataacacac gttcactcct ct          32

<210> SEQ ID NO 51
<211> LENGTH: 32
<212> TYPE: DNA
<213> ORGANISM: Oryza sativa

<400> SEQUENCE: 51
actcctctta tatatcacac gttcactcct ct          32

<210> SEQ ID NO 52
<211> LENGTH: 32
<212> TYPE: DNA
<213> ORGANISM: Oryza sativa

<400> SEQUENCE: 52
actcctctta tatataacac gttcactcct ct          32

<210> SEQ ID NO 53
<211> LENGTH: 32

<212> TYPE: DNA
<213> ORGANISM: Oryza sativa

<400> SEQUENCE: 53
actcctctta tataccac gttcactcct ct                                      32

<210> SEQ ID NO 54
<211> LENGTH: 1100
<212> TYPE: PRT
<213> ORGANISM: Xanthomonas oryzae

<400> SEQUENCE: 54

```

```
                340              345              350
His Gly Leu Thr Pro Asp His Val Ala Ile Ala Ser Asn Ile Gly
                355              360              365
Gly Lys Gln Ala Leu Ala Thr Val Gln Arg Leu Leu Pro Val Leu Cys
            370              375              380
Gln Asp His Gly Leu Thr Pro Asp Gln Val Val Ala Ile Ala Ser His
385              390              395              400
Gly Gly Gly Lys Gln Ala Leu Glu Thr Val Gln Arg Leu Leu Pro Val
                405              410              415
Leu Cys Gln Asp His Gly Leu Thr Pro Asp Gln Val Val Ala Ile Ala
            420              425              430
Ser Asn Ile Gly Gly Lys Gln Ala Leu Glu Thr Val Gln Arg Leu Leu
        435              440              445
Pro Val Leu Cys Gln Asp His Gly Leu Thr Pro Asp Gln Val Val Ala
    450              455              460
Ile Ala Ser Asn Ile Gly Gly Lys Gln Ala Leu Glu Thr Val Gln Arg
465              470              475              480
Leu Leu Pro Val Leu Cys Gln Asp His Gly Leu Thr Pro Asp Gln Val
                485              490              495
Val Ala Ile Ala Ser Asn Gly Gly Lys Gln Ala Leu Glu Thr Val
            500              505              510
Gln Arg Leu Leu Pro Val Leu Cys Gln Thr His Gly Leu Thr Pro Asp
    515              520              525
Gln Val Val Ala Ile Ala Asn His Asp Gly Gly Lys Gln Ala Leu Glu
    530              535              540
Thr Val Gln Arg Leu Leu Pro Val Leu Cys Gln Asp His Gly Leu Thr
545              550              555              560
Pro Asp Gln Val Val Ala Ile Ala Ser Asn Ile Gly Gly Lys Gln Ala
                565              570              575
Leu Ala Thr Val Gln Arg Leu Leu Pro Val Leu Cys Gln Ala His Gly
            580              585              590
Leu Thr Pro Asp Gln Val Val Ala Ile Ala Ser His Asp Gly Gly Lys
        595              600              605
Gln Ala Leu Glu Thr Val Gln Arg Leu Leu Pro Val Leu Cys Gln Asp
    610              615              620
His Gly Leu Thr Pro Asp Gln Val Val Ala Ile Ala Ser Asn Asn Gly
625              630              635              640
Gly Lys Gln Ala Leu Glu Thr Val Gln Arg Leu Leu Pro Val Leu Cys
                645              650              655
Gln Asp His Gly Leu Thr Pro Ala Gln Val Val Ala Ile Ala Asn His
            660              665              670
Gly Gly Gly Lys Gln Ala Leu Glu Thr Val Gln Arg Leu Leu Pro Val
        675              680              685
Leu Cys Gln Asp His Gly Leu Thr Pro Val Gln Val Val Ala Ile Ala
    690              695              700
Ser Asn Ser Gly Gly Lys Gln Ala Leu Glu Thr Val Gln Arg Leu Leu
705              710              715              720
Pro Val Leu Cys Gln Asp His Gly Leu Thr Pro Val Gln Val Val Ala
                725              730              735
Ile Ala Ser Asn Gly Gly Lys Gln Ala Leu Ala Thr Val Gln Arg Leu
            740              745              750
Leu Pro Val Leu Cys Gln Asp His Gly Leu Thr Pro Val Gln Val Val
        755              760              765
```

Ala Ile Ala Ser His Asp Gly Gly Lys Gln Ala Leu Glu Thr Val Gln
770             775                 780

Arg Leu Leu Pro Val Leu Cys Gln Asp His Gly Leu Thr Pro Asp Gln
785                 790                 795                 800

Val Val Ala Ile Ala Ser Asn Gly Gly Lys Gln Ala Leu Glu Ser Ile
            805                 810                 815

Val Ala Gln Leu Ser Arg Pro Asp Pro Ala Leu Ala Ala Leu Thr Asn
            820                 825                 830

Asp His Leu Val Ala Leu Ala Cys Leu Gly Gly Arg Pro Ala Leu Asp
        835                 840                 845

Ala Val Lys Lys Gly Leu Pro His Ala Pro Glu Leu Ile Arg Arg Ile
850                 855                 860

Asn Arg Arg Ile Pro Glu Arg Thr Ser His Arg Val Ala Asp Leu Ala
865                 870                 875                 880

His Val Val Arg Val Leu Gly Phe Phe Gln Ser His Ser His Pro Ala
                885                 890                 895

Gln Ala Phe Asp Asp Ala Met Thr Gln Phe Gly Met Ser Arg His Gly
            900                 905                 910

Leu Ala Gln Leu Phe Arg Arg Val Gly Val Thr Glu Leu Glu Ala Arg
        915                 920                 925

Tyr Gly Thr Leu Pro Pro Ala Ser Gln Arg Trp Asp Arg Ile Leu Gln
930                 935                 940

Ala Ser Gly Met Lys Arg Val Lys Pro Ser Pro Thr Ser Ala Gln Thr
945                 950                 955                 960

Pro Asp Gln Ala Ser Leu His Ala Phe Ala Asp Ser Leu Glu Arg Asp
                965                 970                 975

Leu Asp Ala Pro Ser Pro Met His Glu Gly Asp Gln Thr Arg Ala Ser
            980                 985                 990

Ser Arg Lys Arg Ser Arg Ser Asp Arg Ala Val Thr Gly Pro Ser Thr
            995                 1000                1005

Gln Gln Ser Phe Glu Val Arg Val Pro Glu Gln Gln Asp Ala Leu
    1010                1015                1020

His Leu Pro Leu Ser Trp Arg Val Lys Arg Pro Arg Thr Arg Ile
    1025                1030                1035

Gly Gly Gly Leu Pro Asp Pro Gly Thr Pro Ile Ala Ala Asp Leu
    1040                1045                1050

Ala Ala Ser Ser Thr Val Met Trp Glu Gln Asp Ala Ala Pro Phe
    1055                1060                1065

Ala Gly Ala Ala Asp Asp Phe Pro Ala Phe Asn Glu Glu Leu
    1070                1075                1080

Ala Trp Leu Met Glu Leu Leu Pro Gln Ser Gly Ser Val Gly Gly
    1085                1090                1095

Thr Ile
    1100

<210> SEQ ID NO 55
<211> LENGTH: 1062
<212> TYPE: PRT
<213> ORGANISM: Xanthomonas oryzae

<400> SEQUENCE: 55

Met Asp Pro Ile Arg Ser Arg Thr Pro Ser Pro Ala Arg Glu Leu Leu
1               5                   10                  15

Pro Gly Pro Gln Pro Asp Arg Val Gln Pro Thr Ala Asp Arg Gly Gly

```
                    20                  25                  30
        Ala Pro Pro Ala Gly Pro Leu Asp Gly Leu Pro Ala Arg Arg Thr
                    35                  40                  45
        Met Ser Arg Thr Arg Leu Pro Ser Pro Pro Ala Pro Ser Pro Ala Phe
                50                      55                  60
        Ser Ala Gly Ser Phe Ser Asp Leu Leu Arg Gln Phe Asp Pro Ser Leu
         65                  70                  75                  80
        Leu Asp Thr Ser Leu Leu Asp Ser Met Pro Ala Val Gly Thr Pro His
                        85                  90                  95
        Thr Ala Ala Ala Pro Ala Glu Cys Asp Glu Val Gln Ser Gly Leu Arg
                    100                 105                 110
        Ala Ala Asp Asp Pro Pro Thr Val Arg Val Ala Val Thr Ala Ala
                        115                 120                 125
        Arg Pro Pro Arg Ala Lys Pro Ala Pro Arg Arg Ala Ala Gln Pro
                    130                 135                 140
        Ser Asp Ala Ser Pro Ala Ala Gln Val Asp Leu Arg Thr Leu Gly Tyr
        145                 150                 155                 160
        Ser Gln Gln Gln Glu Lys Ile Lys Pro Lys Val Arg Ser Thr Val
                        165                 170                 175
        Ala Gln His His Glu Ala Leu Val Gly His Gly Phe Thr His Ala His
                        180                 185                 190
        Ile Val Ala Leu Ser Gln His Pro Ala Ala Leu Gly Thr Val Ala Val
                    195                 200                 205
        Thr Tyr Gln Asp Ile Ile Arg Ala Leu Pro Glu Ala Thr His Glu Asp
                    210                 215                 220
        Ile Val Gly Val Gly Lys Gln Trp Ser Gly Ala Arg Ala Leu Glu Ala
        225                 230                 235                 240
        Leu Leu Thr Glu Ala Gly Glu Leu Arg Gly Pro Pro Leu Gln Leu Asp
                        245                 250                 255
        Thr Gly Gln Leu Leu Lys Ile Ala Lys Arg Gly Gly Val Thr Ala Val
                        260                 265                 270
        Glu Ala Val His Ala Trp Arg Asn Ala Leu Thr Gly Ala Pro Leu Asn
                    275                 280                 285
        Leu Thr Pro Asp Gln Val Val Ala Ile Ala Ser Asn Ile Gly Gly Asn
                    290                 295                 300
        Gln Ala Leu Glu Thr Val Gln Arg Leu Leu Pro Val Leu Cys Gln Ala
        305                 310                 315                 320
        His Gly Leu Thr Pro Asp Gln Val Val Ala Ile Ala Ser His Gly Gly
                        325                 330                 335
        Lys Gln Ala Leu Glu Thr Val Gln Arg Leu Leu Pro Val Leu Cys Gln
                    340                 345                 350
        Ala His Gly Leu Thr Pro Asp His Val Val Ala Ile Ala Ser Asn Ile
                    355                 360                 365
        Gly Gly Lys Gln Ala Leu Ala Thr Val Gln Arg Leu Leu Pro Val Leu
                    370                 375                 380
        Cys Gln Asp His Gly Leu Thr Pro Asp Gln Val Val Ala Ile Ala Ser
        385                 390                 395                 400
        His Gly Gly Gly Lys Gln Ala Leu Glu Thr Val Gln Arg Leu Leu Pro
                        405                 410                 415
        Val Leu Cys Gln Asp His Gly Leu Thr Pro Asp Gln Val Val Ala Ile
                    420                 425                 430
        Ala Ser Asn Ile Gly Gly Lys Gln Ala Leu Glu Thr Val Gln Arg Leu
                    435                 440                 445
```

-continued

```
Leu Pro Val Leu Cys Gln Asp His Gly Leu Thr Pro Asp Gln Val Val
    450                 455                 460
Ala Ile Ala Ser Asn Ile Gly Gly Lys Gln Ala Leu Glu Thr Val Gln
465                 470                 475                 480
Arg Leu Leu Pro Val Leu Cys Gln Asp His Gly Leu Thr Pro Asp Gln
                485                 490                 495
Val Val Ala Ile Ala Ser Asn Asn Gly Gly Lys Gln Ala Leu Glu Thr
            500                 505                 510
Val Gln Arg Leu Leu Pro Val Leu Cys Gln Thr His Gly Leu Thr Pro
        515                 520                 525
Asp Gln Val Val Ala Ile Ala Asn His Asp Gly Gly Lys Gln Ala Leu
    530                 535                 540
Glu Thr Val Gln Arg Leu Leu Pro Val Leu Cys Gln Asp His Gly Leu
545                 550                 555                 560
Thr Pro Asp Gln Val Val Ala Ile Ala Ser Asn Ile Gly Gly Lys Gln
                565                 570                 575
Ala Leu Ala Thr Val Gln Arg Leu Leu Pro Val Leu Cys Gln Ala His
            580                 585                 590
Gly Leu Thr Pro Asp Gln Val Val Ala Ile Ala Ser His Asp Gly Gly
        595                 600                 605
Lys Gln Ala Leu Glu Thr Val Gln Arg Leu Leu Pro Val Leu Cys Gln
    610                 615                 620
Asp His Gly Leu Thr Pro Asp Gln Val Val Ala Ile Ala Ser Asn Asn
625                 630                 635                 640
Gly Gly Lys Gln Ala Leu Glu Thr Val Gln Arg Leu Leu Pro Val Leu
                645                 650                 655
Cys Gln Asp His Gly Leu Thr Pro Ala Gln Val Val Ala Ile Ala Asn
            660                 665                 670
His Gly Gly Gly Lys Gln Ala Leu Glu Thr Val Gln Arg Leu Leu Pro
        675                 680                 685
Val Leu Cys Gln Asp His Gly Leu Thr Pro Val Gln Val Val Ala Ile
    690                 695                 700
Ala Ser Asn Ser Gly Gly Lys Gln Ala Leu Glu Thr Val Gln Arg Leu
705                 710                 715                 720
Leu Pro Val Leu Cys Gln Asp His Gly Leu Thr Pro Val Gln Val Val
                725                 730                 735
Ala Ile Ala Ser Asn Gly Gly Lys Gln Ala Leu Ala Thr Val Gln Arg
            740                 745                 750
Leu Leu Pro Val Leu Cys Gln Ala His Gly Leu Thr Pro Val Gln Val
        755                 760                 765
Val Ala Ile Ala Ser His Asp Gly Gly Lys Gln Ala Leu Glu Thr Val
    770                 775                 780
Gln Arg Leu Leu Pro Val Leu Cys Gln Asp His Gly Leu Thr Pro Asp
785                 790                 795                 800
Gln Val Val Ala Ile Ala Ser Asn Gly Gly Lys Gln Ala Leu Glu Ser
                805                 810                 815
Ile Val Ala Gln Leu Ser Arg Pro Asp Pro Ala Leu Ala Ala Leu Thr
            820                 825                 830
Asn Asp His Leu Val Ala Leu Ala Cys Leu Gly Gly Arg Pro Ala Leu
        835                 840                 845
Asp Ala Val Lys Lys Gly Leu Pro His Ala Pro Glu Leu Ile Arg Arg
    850                 855                 860
```

Ile Asn Arg Arg Ile Pro Glu Arg Thr Ser His Arg Val Ala Asp Leu
865                 870                 875                 880

Ala His Val Val Arg Val Leu Gly Phe Phe Gln Ser His Ser His Pro
            885                 890                 895

Ala Gln Ala Phe Asp Asp Ala Met Thr Gln Phe Gly Met Ser Arg His
        900                 905                 910

Gly Leu Ala Gln Leu Phe Arg Arg Val Gly Val Thr Glu Leu Glu Ala
            915                 920                 925

Arg Tyr Gly Thr Leu Pro Pro Ala Ser Gln Arg Trp Asp Arg Ile Leu
    930                 935                 940

Gln Ala Ser Gly Met Lys Arg Ala Lys Pro Ser Pro Thr Ser Ala Gln
945                 950                 955                 960

Thr Pro Asp Gln Ala Ser Leu His Ala Tyr Tyr Lys Asp Asp Asp Asp
            965                 970                 975

Lys Lys Gly Arg Pro Ser Pro Met His Glu Gly Asp Gln Thr Arg Ala
            980                 985                 990

Ser Ser Arg Lys Arg Ser Arg Ser Asp Arg Ala Val Thr Gly Pro Ser
        995                 1000                1005

Thr Gln Gln Ser Phe Glu Val Arg Val Pro Glu Gln  Gln Asp Ala
    1010                1015                1020

Leu His Leu Pro Leu Ser Trp Arg Val Lys Arg Pro  Arg Thr Arg
    1025                1030                1035

Ile Gly Gly Gly Leu Pro Asp Pro Gly Thr Pro Ile  Ala Ala Asp
    1040                1045                1050

Leu Ala Ala Ser Ser Thr Glu  Ile Trp
    1055                1060

<210> SEQ ID NO 56
<211> LENGTH: 1101
<212> TYPE: PRT
<213> ORGANISM: Xanthomonas oryzae

<400> SEQUENCE: 56

Met Asp Pro Ile Arg Ser Arg Thr Pro Ser Pro Ala Arg Glu Leu Leu
1               5                   10                  15

Pro Gly Pro Gln P

```
Ala Gln His His Glu Ala Leu Val Gly His Gly Phe Thr His Ala His
            180                 185                 190
Ile Val Ala Leu Ser Gln His Pro Ala Ala Leu Gly Thr Val Ala Val
            195                 200                 205
Thr Tyr Gln Asp Ile Ile Arg Ala Leu Pro Glu Ala Thr His Glu Asp
        210                 215                 220
Ile Val Gly Val Gly Lys Gln Trp Ser Gly Ala Arg Ala Leu Glu Ala
225                 230                 235                 240
Leu Leu Thr Glu Ala Gly Glu Leu Arg Gly Pro Pro Leu Gln Leu Asp
                245                 250                 255
Thr Gly Gln Leu Leu Lys Ile Ala Lys Arg Gly Gly Val Thr Ala Val
            260                 265                 270
Glu Ala Val His Ala Trp Arg Asn Ala Leu Thr Gly Ala Pro Leu Asn
        275                 280                 285
Leu Thr Pro Asp Gln Val Val Ala Ile Ala Ser Asn Ile Gly Gly Asn
    290                 295                 300
Gln Ala Leu Glu Thr Val Gln Arg Leu Leu Pro Val Leu Cys Gln Ala
305                 310                 315                 320
His Gly Leu Thr Pro Asp Gln Val Val Ala Ile Ala Ser His Gly Gly
                325                 330                 335
Lys Gln Ala Leu Glu Thr Val Gln Arg Leu Leu Pro Val Leu Cys Gln
            340                 345                 350
Ala His Gly Leu Thr Pro Asp His Val Val Ala Ile Ala Ser Asn Ile
        355                 360                 365
Gly Gly Lys Gln Ala Leu Ala Thr Val Gln Arg Leu Leu Pro Val Leu
    370                 375                 380
Cys Gln Asp His Gly Leu Thr Pro Asp Gln Val Val Ala Ile Ala Ser
385                 390                 395                 400
His Gly Gly Gly Lys Gln Ala Leu Glu Thr Val Gln Arg Leu Leu Pro
                405                 410                 415
Val Leu Cys Gln Asp His Gly Leu Thr Pro Asp Gln Val Val Ala Ile
            420                 425                 430
Ala Ser Asn Ile Gly Gly Lys Gln Ala Leu Glu Thr Val Gln Arg Leu
        435                 440                 445
Leu Pro Val Leu Cys Gln Asp His Gly Leu Thr Pro Asp Gln Val Val
    450                 455                 460
Ala Ile Ala Ser Asn Ile Gly Gly Lys Gln Ala Leu Glu Thr Val Gln
465                 470                 475                 480
Arg Leu Leu Pro Val Leu Cys Gln Asp His Gly Leu Thr Pro Asp Gln
                485                 490                 495
Val Val Ala Ile Ala Ser Asn Asn Gly Gly Lys Gln Ala Leu Glu Thr
            500                 505                 510
Val Gln Arg Leu Leu Pro Val Leu Cys Gln Thr His Gly Leu Thr Pro
        515                 520                 525
Asp Gln Val Val Ala Ile Ala Asn His Asp Gly Gly Lys Gln Ala Leu
    530                 535                 540
Glu Thr Val Gln Arg Leu Leu Pro Val Leu Cys Gln Asp His Gly Leu
545                 550                 555                 560
Thr Pro Asp Gln Val Val Ala Ile Ala Ser Asn Ile Gly Gly Lys Gln
                565                 570                 575
Ala Leu Ala Thr Val Gln Arg Leu Leu Pro Val Leu Cys Gln Ala His
            580                 585                 590
```

```
Gly Leu Thr Pro Asp Gln Val Val Ala Ile Ala Ser His Asp Gly
            595                 600                 605

Lys Gln Ala Leu Glu Thr Val Gln Arg Leu Leu Pro Val Leu Cys Gln
610                 615                 620

Asp His Gly Leu Thr Pro Asp Gln Val Val Ala Ile Ala Ser Asn Asn
625                 630                 635                 640

Gly Gly Lys Gln Ala Leu Glu Thr Val Gln Arg Leu Leu Pro Val Leu
                645                 650                 655

Cys Gln Asp His Gly Leu Thr Pro Ala Gln Val Val Ala Ile Ala Asn
                660                 665                 670

His Gly Gly Lys Gln Ala Leu Glu Thr Val Gln Arg Leu Leu Pro
    675                 680                 685

Val Leu Cys Gln Asp His Gly Leu Thr Pro Val Gln Val Val Ala Ile
    690                 695                 700

Ala Ser Asn Ser Gly Gly Lys Gln Ala Leu Glu Thr Val Gln Arg Leu
705                 710                 715                 720

Leu Pro Val Leu Cys Gln Asp His Gly Leu Thr Pro Val Gln Val Val
                725                 730                 735

Ala Ile Ala Ser Asn Gly Gly Lys Gln Ala Leu Ala Thr Val Gln Arg
                740                 745                 750

Leu Leu Pro Val Leu Cys Gln Ala His Gly Leu Thr Pro Val Gln Val
            755                 760                 765

Val Ala Ile Ala Ser His Asp Gly Gly Lys Gln Ala Leu Glu Thr Val
            770                 775                 780

Gln Arg Leu Leu Pro Val Leu Cys Gln Asp His Gly Leu Thr Pro Asp
785                 790                 795                 800

Gln Val Val Ala Ile Ala Ser Asn Gly Gly Lys Gln Ala Leu Glu Ser
                805                 810                 815

Ile Val Ala Gln Leu Ser Arg Pro Asp Pro Ala Leu Ala Ala Leu Thr
                820                 825                 830

Asn Asp His Leu Val Ala Leu Ala Cys Leu Gly Gly Arg Pro Ala Leu
                835                 840                 845

Asp Ala Val Lys Lys Gly Leu Pro His Ala Pro Glu Leu Ile Arg Arg
850                 855                 860

Ile Asn Arg Arg Ile Pro Glu Arg Thr Ser His Arg Val Ala Asp Leu
865                 870                 875                 880

Ala His Val Val Arg Val Leu Gly Phe Phe Gln Ser His Ser His Pro
                885                 890                 895

Ala Gln Ala Phe Asp Asp Ala Met Thr Gln Phe Gly Met Ser Arg His
                900                 905                 910

Gly Leu Ala Gln Leu Phe Arg Arg Val Gly Val Thr Glu Leu Glu Ala
            915                 920                 925

Arg Tyr Gly Thr Leu Pro Pro Ala Ser Gln Arg Trp Asp Arg Ile Leu
    930                 935                 940

Gln Ala Ser Gly Met Ala Ala Val Asp Leu Ser Pro Thr Ser Ala Gln
945                 950                 955                 960

Thr Pro Asp Gln Ala Ser Leu His Ala Phe Ala Asp Ser Leu Glu Arg
                965                 970                 975

Asp Leu Asp Ala Pro Ser Pro Met His Glu Gly Asp Gln Thr Arg Ala
            980                 985                 990

Ser Ser Ala Ala Ala Ser Gly Ser  Asp Arg Ala Val  Thr Gly Pro Ser
    995                 1000                1005

Thr Gln  Gln Ser Phe Glu Val  Arg Val Pro Glu Gln  Gln Asp Ala
```

| | 1010 | | | | 1015 | | | | | 1020 | | |
|---|---|---|---|---|---|---|---|---|---|---|---|---|
Leu His Leu Pro Leu Ser Trp Asn Ser Ala Gly Pro Arg Thr Arg
　　1025　　　　　　　　1030　　　　　　　　　　　1035

Ile Gly Gly Gly Leu Pro Asp Pro Gly Thr Pro Ile Ala Ala Asp
　　1040　　　　　　　　1045　　　　　　　　　　　1050

Leu Ala Ala Ser Ser Thr Val Met Trp Glu Gln Asp Ala Ala Pro
　　1055　　　　　　　　1060　　　　　　　　　　　1065

Phe Ala Gly Ala Ala Asp Asp Phe Pro Ala Phe Asn Glu Glu Glu
　　1070　　　　　　　　1075　　　　　　　　　　　1080

Leu Ala Trp Leu Met Glu Leu Leu Pro Gln Ser Gly Ser Val Gly
　　1085　　　　　　　　1090　　　　　　　　　　　1095

Gly Thr Ile
　　1100

<210> SEQ ID NO 57
<211> LENGTH: 3309
<212> TYPE: DNA
<213> ORGANISM: Xanthomonas oryzae

<400> SEQUENCE: 57

```

```
tgccagaccc atggcctgac cccggaccag gtcgtggcca tcgccaacca cgatggcggc    1620
aagcaggcgc tggagacggt gcagcggctg ttgccggtgc tgtgccagga ccatggcctg    1680
accccggacc aggtcgtggc catcgccagc aatattggcg gcaagcaggc gctggcgacg    1740
gtgcagcggc tgttgccggt gctgtgccag gcccatggcc tgaccccgga ccaggtcgtg    1800
gccatcgcca gccacgatgg cggcaagcag gcgctggaga cggtgcagcg gctgttgccg    1860
gtgctgtgcc aggaccatgg actgaccccg gaccaggtgg tggccatcgc cagcaataac    1920
ggcggcaagc aggcgctgga cggtgcagc ggctgttgc cggtgctgtg ccaggaccat    1980
ggcctgaccc cggcccaggt ggtggccatc gccaaccatg cggcggcaa gcaggcgctg    2040 gagacggtgc agcggctgtt gccggtgctg tgccaggacc atggcctgac cccggtccag    2100
gtggtggcca tcgccagcaa tagcggcggc aagcaggcgc tggagacggt gcagcggctg    2160
ttgccggtgc tgtgccagga ccatggcctg accccggtcc aggtggtggc catcgccagc    2220
aatggcggcg gcaagcaggc gctggcgacg gtgcagcggc tgttgccggt gctgtgccag    2280
gaccatggcc tgaccccggt ccaggtggtg gccatcgcca gccacgatgg cggcaagcag    2340
gcgctggaga cggtgcagcg gctgttgccg gtgctgtgcc aggaccatgg cctgacccca    2400
gaccaggtgg tggccatcgc cagcaatggc ggcaagcagg cgctggagag cattgttgcc    2460
cagttatctc gccctgatcc ggcgttggcc gcgttgacca cgaccacct cgtcgccttg    2520 gcctgcctcg gcggacgtcc tgccctggat gcagtgaaaa agggattgcc gcacgcaccg    2580
gaattgatca aagaatcaa tcgccgtatt cccgaacgca cgtccatcg cgttgccgac    2640 ctcgcgcacg tggtgcgcgt gcttggtttt ttccagagcc actcccaccc agcgcaagca    2700
ttcgatgacg ccatgacgca gttcgggatg agcaggcacg ggttggcaca gctctttcgc    2760
agagtgggcg tcaccgaact cgaagcccgc tacggaacgc tcccccccagc ctcgcagcgt    2820 tgggaccgta tcctccaggc atcagggatg aaaagggtca aaccgtcccc tacttcagct    2880
caaacgccgg atcaggcgtc tttgcatgca ttcgccgatt cgctggagcg tgaccttgat    2940
gcgcccagcc caatgcacga gggagatcag acgcgggcaa gcagccgtaa acggtcccga    3000
tcggatcgtg ctgtcaccgg cccctccaca cagcaatctt tcgaggtgcg cgttcccgaa    3060
cagcaagatg cgctgcattt gccccctcagc tggagggtaa aacgcccgcg taccaggatc    3120
gggggcggcc tccggatcc tggtacgccc atcgctgccg acctggcagc gtccagcacc    3180
gtgatgtggg aacaagatgc ggccccccttc gcaggggcag cggatgattt cccggcattc    3240
aacgaagagg agctcgcatg gttgatggag ctattgcctc agtcaggctc agtcggaggg    3300
acgatctga                                                            3309
```

<210> SEQ ID NO 58
<211> LENGTH: 32
<212> TYPE: DNA
<213> ORGANISM: Oryza sativa

<400> SEQUENCE: 58
actcctctta tatatacaac gttcactcct ct                                    32

<210> SEQ ID NO 59
<211> LENGTH: 32
<212> TYPE: DNA
<213> ORGANISM: Oryza sativa

<400> SEQUENCE: 59

```
actcctctta tatatacacc gttcactcct ct                                   32
```

<210> SEQ ID NO 60
<211> LENGTH: 32
<212> TYPE: DNA
<213> ORGANISM: Oryza sativa

<400> SEQUENCE: 60

```
actcctctta tatatacaca gttcactcct ct                                   32
```

<210> SEQ ID NO 61
<211> LENGTH: 32
<212> TYPE: DNA
<213> ORGANISM: Oryza sativa

<400> SEQUENCE: 61

```
actcctctta tatatacaca cttcactcct ct                                   32
```

<210> SEQ ID NO 62
<211> LENGTH: 32
<212> TYPE: DNA
<213> ORGANISM: Oryza sativa

<400> SEQUENCE: 62

```
actcctctta tatatacaca cgtcactcct ct                                   32
```

<210> SEQ ID NO 63
<211> LENGTH: 32
<212> TYPE: DNA
<213> ORGANISM: Oryza sativa

<400> SEQUENCE: 63

```
actcctctta tatatacaca cgtcactcct ct                                   32
```

<210> SEQ ID NO 64
<211> LENGTH: 32
<212> TYPE: DNA
<213> ORGANISM: Oryza sativa

<400> SEQUENCE: 64

```
actcctctta tatatacaca cgttactcct ct                                   32
```

<210> SEQ ID NO 65
<211> LENGTH: 32
<212> TYPE: DNA
<213> ORGANISM: Oryza sativa

<400> SEQUENCE: 65

```
actcctctta tatatacaca cgttcctcct ct                                   32
```

<210> SEQ ID NO 66
<211> LENGTH: 32
<212> TYPE: DNA
<213> ORGANISM: Oryza sativa

<400> SEQUENCE: 66

```
actcctctta tatatacaca cgttcatcct ct                                   32
```

<210> SEQ ID NO 67
<211> LENGTH: 17
<212> TYPE: DNA
<213> ORGANISM: Oryza sativa

<400> SEQUENCE: 67

-continued tatatacatc agttcac                                              17

<210> SEQ ID NO 68
<211> LENGTH: 17
<212> TYPE: DNA
<213> ORGANISM: Oryza sativa

<400> SEQUENCE: 68
tatatacaca cattact                                              17

<210> SEQ ID NO 69
<211> LENGTH: 17
<212> TYPE: DNA
<213> ORGANISM: Oryza sativa

<400> SEQUENCE: 69
tatatacacc aattact                                              17

<210> SEQ ID NO 70
<211> LENGTH: 17
<212> TYPE: DNA
<213> ORGANISM: Oryza sativa

<400> SEQUENCE: 70
tatatacata aattact                                              17

<210> SEQ ID NO 71
<211> LENGTH: 17
<212> TYPE: DNA
<213> ORGANISM: Oryza sativa

<400> SEQUENCE: 71
tatatacatc cattact                                              17

<210> SEQ ID NO 72
<211> LENGTH: 17
<212> TYPE: DNA
<213> ORGANISM: Oryza sativa

<400> SEQUENCE: 72
tatatacaca aattact                                              17

<210> SEQ ID NO 73
<211> LENGTH: 17
<212> TYPE: DNA
<213> ORGANISM: Oryza sativa

<400> SEQUENCE: 73
tatatacacc cattact                                              17

<210> SEQ ID NO 74
<211> LENGTH: 17
<212> TYPE: DNA
<213> ORGANISM: Oryza sativa

<400> SEQUENCE: 74
tatatacata cattact                                              17

<210> SEQ ID NO 75
<211> LENGTH: 33
<212> TYPE: DNA
<213> ORGANISM: Oryza sativa

<400> SEQUENCE: 75
actcctctta tatatacatc agttcactcc tct                                    33

<210> SEQ ID NO 76
<211> LENGTH: 33
<212> TYPE: DNA
<213> ORGANISM: Oryza sativa

<400> SEQUENCE: 76
ttctcttata tatacatcaa ttacttattg atg                                    33

<210> SEQ ID NO 77
<211> LENGTH: 33
<212> TYPE: DNA
<213> ORGANISM: Oryza sativa

<400> SEQUENCE: 77
ttctcttata tatacacaca ttacttattg atg                                    33

<210> SEQ ID NO 78
<211> LENGTH: 20
<212> TYPE: DNA
<213> ORGANISM: Saccharomyces cerevisiae

<400> SEQUENCE: 78
cattacgacc gagattcccg                                                   20

<210> SEQ ID NO 79
<211> LENGTH: 3411
<212> TYPE: DNA
<213> ORGANISM: Xanthomonas oryzae

<400> SEQUENCE: 79
atggatccca ttcgttcgcg cacgccaagt cctgcccgcg agcttctgcc cggaccccaa 60
ccggataggg ttcagccgac tgcagatcgg ggggggctc cgcctgctgg cggccccctg 120
gatggcttgc ccgctcggcg gacgatgtcc cggacccggc tgccatctcc ccctgcgccc 180
tcgcctgcgt tctcggcggg cagcttcaac gatctgctcc gtcagttcga tccgtcgctt 240
cttgatacat cgcttcttga ttcgatgcct gccgtcggca cgccgcatac agcggctgcc 300
ccagcagagt gggatgaggt gcaatcgggt ctgcgtgcag ccgatgaccc gccacccacc 360
gtgcgtgtcg ctgtcactgc cgcgcggccg ccgcgcgcca agccggcccc gcgacggcgt 420
gcggcgcaac cctccgacgc ttcgccggcc gcgcaggtgg atctacgcac gctcggctac 480
agtcagcagc agcaagagaa gatcaaatcg aaggtgcgtt cgacagtggc gcagcaccac 540
gaggcactgg tgggccatgg gtttacacac gcgcacatcg ttgcgctcag ccaacacccg 600
gcagcgttag ggaccgtcgc tgtcaagtat cagcacataa tcacggcgtt gccagaggcg 660
acacacgaag acatcgttgg cgtcggcaaa cagtggtccg gcgcacgcgc cctggaggcc 720
ttgctcacga aggcgggga gttgagaggt ccgccgttac agttggacac aggccaactt 780
ctcaagattg caaaacgtgg cggcgtgacc gcagtggagg cagtgcatgc atcgcgcaat 840
gcactgacgg gtgcccccct gaacctgacc ccggaccaag tggtggccat cgccagcaat 900
attggcggca accaggcgct ggagacggtg cagcggctgt tgccggtgct gtgccaggac 960
catggcctga ccccggacca agtggtggcc atcgccaaca ataacggcgg caagcaggcg 1020
ctggagacgg tgcagcggct gttgccggtg ctgtgccagg cccatggcct gaccccggac 1080
caagtggtgg ccatcgccag caatggcggc aagcaggcgc tggagacggt gcagcggctg 1140

```
ttgccggtgc tgtgccaggc ccatggcctg accccgaacc aggtcgtggc catcgccagc    1200
aatggcggcg gcaagcaggc gctggagacg gtgcagcggc tgttgccggt gctgtgccag    1260
gcccatggcc tgacccagga ccaggtggtg gccatcgcca gcaatagtgg cggcaagcag    1320
gcgctggaga cggtgcagcg gctgttgccg gtgctgtgcc aggcccatgg cctgaccccg    1380
gcccaagtgg tggccatcgc cagcaataac ggcggcaagc aggcgctgga cggtgcag     1440 cggctgtttc cggtgctgtg ccaggaccat ggcctgaccc cggaccaggt ggtgaccatc    1500
gccaacaata acggcggcaa gcaggcgctg agacggtgc agcggctgtt gccggtgctg    1560
tgccaggccc atggcttgat cccggaccag gtggtggcca tcgccaacaa taacggcggc    1620
aagcaggcgc tggagacggt gcagcggctg ttgccggtgc tgtgccaggc ccatggcctg    1680
accccgcccc aagtggtggc catcgccagc aatattggcg gcaagcaggc gctggagacg    1740
gtgcagcggc tgttgccggt gctgtgccgg gcccatggcc tgaccccggc caagtggtg    1800 gccatcgcca caataacgg cggcaagcag gcgctggaga cggtgcagcg gctgttgccg    1860
gtgctgtgcc aggcccatgg cctgaccccg gatcaagtgg tggccatcgc cagcaatatt    1920
ggcggcaagc aggcgctgga cggtgcag cgcctgttgc cggtgctgtg ccaggaccat    1980
ggcctgaccc cggaccaggt cgtggccatc gccagcaatg gcggcaagca ggcgctggag    2040
acggtgcagc ggctgttgcc ggtgctgtgc caggaccatg gcctgacccc ggcccaggtg    2100
gtggccatcg ccagccacga tggcggcaag caggcgctgg agacggtgca gcggctgttg    2160
ccggtgctgt gccaggacca tggcctgacc ctggaccagg tcgtggccat cgccagccac    2220
gatggcggca agcaggcgct ggagacggtg cagcggctgt tgccggtgct gtgccaggac    2280
catggcctga ccctgaccca ggtggtggcc atcgccagca atattggcgg caagcaggcg    2340
ctggagacgg tgcagcggct gttgccggtg ctgtgccagg accatggcct gaccccggac    2400
caggtcgtgg ccatcgccag caatggcggc ggcaagcagg cgctggagac ggtgcaacgg    2460
ctgttgccgg tgctgtgcca ggaccatggc ctgaccccgg accaggtcgt ggccatcgcc    2520
agcaatggcg gcggcaagca ggcgctggag agcattgttg cccagttatc tcgccctgat    2580
ccggcgttgg ccgcgttgac caacgaccac ctcgtcgcct tggcctgcct cggcggacgt    2640
cctgccctgg atgcagtgaa aaagggattg ccgcacgcgc cggaattgat cagaagaatc    2700
aatcgccgta ttcccgaacg cacgtcccat cgcgttgccg acctcgcgca cgtggtgcgc    2760
gtgcttggtt ttttccagag ccactcccac ccagcgcaag cattcgatga cgccatgacg    2820
cagttcggga tgagcaggca cggggttggta cagctctttc gcagagtggg cgtcaccgaa    2880
ttcgaagccc gctgcggaac gctcccccca gcctcgcagc gttgggaccg tatcctccag    2940
gcatcaggga tgaaaaggg caaaccgtcc cctacttcag ctcaaacgcc ggatcaggcg    3000
tctttgcatg cattcgccga ttcgctggag cgtgaccttg atgcgcccag cccaatgcac    3060
gagggagatc agacgcgggc aagcagccgt aaacggtccc gatcggatcg tgctgtcacc    3120
ggcccctcca cacagcaatc tttcgaggtg cgcgttccgg aacagcgcga tgcgctgcat    3180
ttgcccctca gctggagggt aaaacgcccg cgtaccagga tcggggcgg cctcccggat    3240 cctggtacgc ccatcgctgc cgacctgca gcgtccagca ccgtgatgtg gaacaagat    3300 gcggcccct tcgcaggggc agcggatgat ttcccggcat tcaacgaaga ggagctcgca    3360
tggttgatgg agctattgcc tcagtcaggc tcagtcggag ggacgatctg a            3411
```

<210> SEQ ID NO 80

<211> LENGTH: 1136
<212> TYPE: PRT
<213> ORGANISM: Xanthomonas oryzae

<400> SEQUENCE: 80

Met Asp Pro Ile Arg Ser Arg Thr Pro Ser Pro Ala Arg Glu Leu Leu
1               5                   10                  15

Pro Gly Pro Gln Pro Asp Arg Val Gln Pro Thr Ala Asp Arg Gly Gly
            20                  25                  30

Ala Pro Pro Ala Gly Gly Pro Leu Asp Gly Leu Pro Ala Arg Arg Thr
        35                  40                  45

Met Ser Arg Thr Arg Leu Pro Ser Pro Ala Pro Ser Pro Ala Phe
50                  55                  60

Ser Ala Gly Ser Phe Asn Asp Leu Leu Arg Gln Phe Asp Pro Ser Leu
65                  70                  75                  80

Leu Asp Thr Ser Leu Leu Asp Ser Met Pro Ala Val Gly Thr Pro His
                85                  90                  95

Thr Ala Ala Ala Pro Ala Glu Trp Asp Glu Val Gln Ser Gly Leu Arg
            100                 105                 110

Ala Ala Asp Asp Pro Pro Thr Val Arg Val Ala Val Thr Ala Ala
        115                 120                 125

Arg Pro Pro Arg Ala Lys Pro Ala Pro Arg Arg Ala Ala Gln Pro
130                 135                 140

Ser Asp Ala Ser Pro Ala Ala Gln Val Asp Leu Arg Thr Leu Gly Tyr
145                 150                 155                 160

Ser Gln Gln Gln Gln Glu Lys Ile Lys Ser Lys Val Arg Ser Thr Val
                165                 170                 175

Ala Gln His His Glu Ala Leu Val Gly His Gly Phe Thr His Ala His
            180                 185                 190

Ile Val Ala Leu Ser Gln His Pro Ala Ala Leu Gly Thr Val Ala Val
        195                 200                 205

Lys Tyr Gln His Ile Ile Thr Ala Leu Pro Glu Ala Thr His Glu Asp
210                 215                 220

Ile Val Gly Val Gly Lys Gln Trp Ser Gly Ala Arg Ala Leu Glu Ala
225                 230                 235                 240

Leu Leu Thr Lys Ala Gly Glu Leu Arg Gly Pro Pro Leu Gln Leu Asp
                245                 250                 255

Thr Gly Gln Leu Leu Lys Ile Ala Lys Arg Gly Gly Val Thr Ala Val
            260                 265                 270

Glu Ala Val His Ala Ser Arg Asn Ala Leu Thr Gly Ala Pro Leu Asn
        275                 280                 285

Leu Thr Pro Asp Gln Val Val Ala Ile Ala Ser Asn Ile Gly Gly Asn
290                 295                 300

Gln Ala Leu Glu Thr Val Gln Arg Leu Leu Pro Val Leu Cys Gln Asp
305                 310                 315                 320

His Gly Leu Thr Pro Asp Gln Val Val Ala Ile Ala Asn Asn Asn Gly
                325                 330                 335

Gly Lys Gln Ala Leu Glu Thr Val Gln Arg Leu Leu Pro Val Leu Cys
            340                 345                 350

Gln Ala His Gly Leu Thr Pro Asp Gln Val Val Ala Ile Ala Ser Asn
        355                 360                 365

Gly Gly Lys Gln Ala Leu Glu Thr Val Gln Arg Leu Leu Pro Val Leu
370                 375                 380

Cys Gln Ala His Gly Leu Thr Pro Asn Gln Val Val Ala Ile Ala Ser

-continued

```
            385                 390                 395                 400
Asn Gly Gly Gly Lys Gln Ala Leu Glu Thr Val Gln Arg Leu Leu Pro
                    405                 410                 415
Val Leu Cys Gln Ala His Gly Leu Thr Gln Asp Gln Val Val Ala Ile
            420                 425                 430
Ala Ser Asn Ser Gly Gly Lys Gln Ala Leu Glu Thr Val Gln Arg Leu
        435                 440                 445
Leu Pro Val Leu Cys Gln Ala His Gly Leu Thr Pro Ala Gln Val Val
    450                 455                 460
Ala Ile Ala Ser Asn Asn Gly Gly Lys Gln Ala Leu Glu Thr Val Gln
465                 470                 475                 480
Arg Leu Phe Pro Val Leu Cys Gln Asp His Gly Leu Thr Pro Asp Gln
                485                 490                 495
Val Val Thr Ile Ala Asn Asn Asn Gly Gly Lys Gln Ala Leu Glu Thr
            500                 505                 510
Val Gln Arg Leu Leu Pro Val Leu Cys Gln Ala His Gly Leu Ile Pro
        515                 520                 525
Asp Gln Val Val Ala Ile Ala Asn Asn Gly Gly Lys Gln Ala Leu
    530                 535                 540
Glu Thr Val Gln Arg Leu Leu Pro Val Leu Cys Gln Ala His Gly Leu
545                 550                 555                 560
Thr Pro Ala Gln Val Val Ala Ile Ala Ser Asn Ile Gly Gly Lys Gln
                565                 570                 575
Ala Leu Glu Thr Val Gln Arg Leu Leu Pro Val Leu Cys Arg Ala His
            580                 585                 590
Gly Leu Thr Pro Ala Gln Val Val Ala Ile Ala Asn Asn Asn Gly Gly
        595                 600                 605
Lys Gln Ala Leu Glu Thr Val Gln Arg Leu Leu Pro Val Leu Cys Gln
    610                 615                 620
Ala His Gly Leu Thr Pro Asp Gln Val Val Ala Ile Ala Ser Asn Ile
625                 630                 635                 640
Gly Gly Lys Gln Ala Leu Glu Thr Val Gln Arg Leu Leu Pro Val Leu
                645                 650                 655
Cys Gln Asp His Gly Leu Thr Pro Asp Gln Val Val Ala Ile Ala Ser
            660                 665                 670
Asn Gly Gly Lys Gln Ala Leu Glu Thr Val Gln Arg Leu Leu Pro Val
        675                 680                 685
Leu Cys Gln Asp His Gly Leu Thr Pro Ala Gln Val Val Ala Ile Ala
    690                 695                 700
Ser His Asp Gly Gly Lys Gln Ala Leu Glu Thr Val Gln Arg Leu Leu
705                 710                 715                 720
Pro Val Leu Cys Gln Asp His Gly Leu Thr Leu Asp Gln Val Val Ala
                725                 730                 735
Ile Ala Ser His Asp Gly Gly Lys Gln Ala Leu Glu Thr Val Gln Arg
            740                 745                 750
Leu Leu Pro Val Leu Cys Gln Asp His Gly Leu Thr Leu Asp Gln Val
        755                 760                 765
Val Ala Ile Ala Ser Asn Ile Gly Gly Lys Gln Ala Leu Glu Thr Val
    770                 775                 780
Gln Arg Leu Leu Pro Val Leu Cys Gln Asp His Gly Leu Thr Pro Asp
785                 790                 795                 800
Gln Val Val Ala Ile Ala Ser Asn Gly Gly Gly Lys Gln Ala Leu Glu
                805                 810                 815
```

-continued

```
Thr Val Gln Arg Leu Leu Pro Val Leu Cys Gln Asp His Gly Leu Thr
            820                 825                 830

Pro Asp Gln Val Val Ala Ile Ala Ser Asn Gly Gly Lys Gln Ala
        835                 840                 845

Leu Glu Ser Ile Val Ala Gln Leu Ser Arg Pro Asp Pro Ala Leu Ala
850                 855                 860

Ala Leu Thr Asn Asp His Leu Val Ala Leu Ala Cys Leu Gly Gly Arg
865                 870                 875                 880

Pro Ala Leu Asp Ala Val Lys Lys Gly Leu Pro His Ala Pro Glu Leu
            885                 890                 895

Ile Arg Arg Ile Asn Arg Arg Ile Pro Glu Arg Thr Ser His Arg Val
                900                 905                 910

Ala Asp Leu Ala His Val Val Arg Val Leu Gly Phe Phe Gln Ser His
            915                 920                 925

Ser His Pro Ala Gln Ala Phe Asp Asp Ala Met Thr Gln Phe Gly Met
        930                 935                 940

Ser Arg His Gly Leu Val Gln Leu Phe Arg Arg Val Gly Val Thr Glu
945                 950                 955                 960

Phe Glu Ala Arg Cys Gly Thr Leu Pro Pro Ala Ser Gln Arg Trp Asp
                965                 970                 975

Arg Ile Leu Gln Ala Ser Gly Met Lys Arg Ala Lys Pro Ser Pro Thr
            980                 985                 990

Ser Ala Gln Thr Pro Asp Gln Ala  Ser Leu His Ala Phe  Ala Asp Ser
        995                 1000                1005

Leu Glu  Arg Asp Leu Asp Ala  Pro Ser Pro Met His  Glu Gly Asp
    1010                1015                1020

Gln Thr  Arg Ala Ser Ser Arg  Lys Arg Ser Arg Ser  Asp Arg Ala
    1025                1030                1035

Val Thr  Gly Pro Ser Thr Gln  Gln Ser Phe Glu Val  Arg Val Pro
    1040                1045                1050

Glu Gln  Arg Asp Ala Leu His  Leu Pro Leu Ser Trp  Arg Val Lys
    1055                1060                1065

Arg Pro  Arg Thr Arg Ile Gly  Gly Gly Leu Pro Asp  Pro Gly Thr
    1070                1075                1080

Pro Ile  Ala Ala Asp Leu Ala  Ala Ser Ser Thr Val  Met Trp Glu
    1085                1090                1095

Gln Asp  Ala Ala Pro Phe Ala  Gly Ala Ala Asp  Phe Pro Ala
    1100                1105                1110

Phe Asn  Glu Glu Glu Leu Ala  Trp Leu Met Glu Leu  Leu Pro Gln
    1115                1120                1125

Ser Gly  Ser Val Gly Gly Thr  Ile
    1130                1135

<210> SEQ ID NO 81
<211> LENGTH: 13
<212> TYPE: DNA
<213> ORGANISM: Oryza sativa

<400> SEQUENCE: 81
tatatacaca cgt                                                          13

<210> SEQ ID NO 82
<211> LENGTH: 16
<212> TYPE: DNA
<213> ORGANISM: Oryza sativa
```

```
<400> SEQUENCE: 82
tatatacaca cgtcac                                                    16

<210> SEQ ID NO 83
<211> LENGTH: 16
<212> TYPE: DNA
<213> ORGANISM: Oryza sativa

<400> SEQUENCE: 83
tatatacaca cgttac                                                    16

<210> SEQ ID NO 84
<211> LENGTH: 16
<212> TYPE: DNA
<213> ORGANISM: Oryza sativa

<400> SEQUENCE: 84
tatatacaca cgttcc                                                    16

<210> SEQ ID NO 85
<211> LENGTH: 16
<212> TYPE: DNA
<213> ORGANISM: Oryza sativa

<400> SEQUENCE: 85
tatatacaca cgttca                                                    16

<210> SEQ ID NO 86
<211> LENGTH: 16
<212> TYPE: DNA
<213> ORGANISM: Oryza sativa

<400> SEQUENCE: 86
ttatacacac gttcac                                                    16

<210> SEQ ID NO 87
<211> LENGTH: 16
<212> TYPE: DNA
<213> ORGANISM: Oryza sativa

<400> SEQUENCE: 87
taatacacac gttcac                                                    16

<210> SEQ ID NO 88
<211> LENGTH: 16
<212> TYPE: DNA
<213> ORGANISM: Oryza sativa

<400> SEQUENCE: 88
tattacacac gttcac                                                    16

<210> SEQ ID NO 89
<211> LENGTH: 16
<212> TYPE: DNA
<213> ORGANISM: Oryza sativa

<400> SEQUENCE: 89
tataacacac gttcac                                                    16

<210> SEQ ID NO 90
<211> LENGTH: 16
<212> TYPE: DNA
```

<213> ORGANISM: Oryza sativa

<400> SEQUENCE: 90
tatatcacac gttcac                                                         16

<210> SEQ ID NO 91
<211> LENGTH: 16
<212> TYPE: DNA
<213> ORGANISM: Oryza sativa

<400> SEQUENCE: 91
tatataacac gttcac                                                         16

<210> SEQ ID NO 92
<211> LENGTH: 16
<212> TYPE: DNA
<213> ORGANISM: Oryza sativa

<400> SEQUENCE: 92
tatataccac gttcac                                                         16

<210> SEQ ID NO 93
<211> LENGTH: 16
<212> TYPE: DNA
<213> ORGANISM: Oryza sativa

<400> SEQUENCE: 93
tatatacaac gttcac                                                         16

<210> SEQ ID NO 94
<211> LENGTH: 16
<212> TYPE: DNA
<213> ORGANISM: Oryza sativa

<400> SEQUENCE: 94
tatatacacc gttcac                                                         16

<210> SEQ ID NO 95
<211> LENGTH: 16
<212> TYPE: DNA
<213> ORGANISM: Oryza sativa

<400> SEQUENCE: 95
tatatacaca gttcac                                                         16

<210> SEQ ID NO 96
<211> LENGTH: 16
<212> TYPE: DNA
<213> ORGANISM: Oryza sativa

<400> SEQUENCE: 96
tatatacaca cttcac                                                         16

<210> SEQ ID NO 97
<211> LENGTH: 16
<212> TYPE: DNA
<213> ORGANISM: Oryza sativa

<400> SEQUENCE: 97
tatatacaca cgtcac                                                         16